United States Patent
Sellmyer et al.

(10) Patent No.: US 10,835,625 B2
(45) Date of Patent: Nov. 17, 2020

(54) RADIOTRACER DERIVATIVES OF TRIMETHOPRIM FOR DIAGNOSTIC IMAGING

(71) Applicant: The Trustees of the University of Pennsylvania, Philadelphia, PA (US)

(72) Inventors: Mark Sellmyer, Philadelphia, PA (US); Robert H. Mach, Wallingford, PA (US); David A. Mankoff, Philadelphia, PA (US); Iljung Lee, Secane, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 16/511,052

(22) Filed: Jul. 15, 2019

(65) Prior Publication Data

US 2019/0381197 A1    Dec. 19, 2019

Related U.S. Application Data

(62) Division of application No. 15/572,632, filed as application No. PCT/US2016/031600 on May 10, 2016, now Pat. No. 10,398,790.

(60) Provisional application No. 62/159,327, filed on May 10, 2015.

(51) Int. Cl.
| | |
|---|---|
| *A61K 51/04* | (2006.01) |
| *A61K 49/00* | (2006.01) |
| *A61K 31/395* | (2006.01) |
| *A61K 31/495* | (2006.01) |
| *C07D 239/49* | (2006.01) |
| *C07D 403/12* | (2006.01) |
| *A61K 47/54* | (2017.01) |
| *A61K 31/505* | (2006.01) |

(52) U.S. Cl.
CPC ........ *A61K 51/0459* (2013.01); *A61K 31/395* (2013.01); *A61K 31/495* (2013.01); *A61K 31/505* (2013.01); *A61K 47/547* (2017.08); *A61K 49/0021* (2013.01); *A61K 49/0052* (2013.01); *A61K 51/0453* (2013.01); *A61K 51/0497* (2013.01); *C07D 239/49* (2013.01); *C07D 403/12* (2013.01); *C07B 2200/05* (2013.01); *Y02A 50/473* (2018.01); *Y02A 50/481* (2018.01)

(58) Field of Classification Search
CPC ........ A61K 51/04; A61K 49/00; A61K 47/54; A61K 31/395
See application file for complete search history.

(56) References Cited

U.S. PATENT DOCUMENTS

| | | |
|---|---|---|
| 2005/0238628 A1 | 10/2005 | Blau |
| 2009/0214439 A1 | 8/2009 | Kumar et al. |
| 2014/0219917 A1 | 8/2014 | Murthy et al. |
| 2014/0314671 A1 | 10/2014 | Namavari et al. |

FOREIGN PATENT DOCUMENTS

WO    2012/175702 A1    12/2012

OTHER PUBLICATIONS

Nathaniel T. Calloway et al. Optimized Fluorescent Trimethoprim Derivatives for in vivo Protein Labeling, ChemBioChem, 8, 767-774. (Year: 2007).*
Akhtar et al., "Antimicrobial peptides as infection imaging agents: better than radiolabeled antibiotics", Int J Rept., vol. 2012, 2012:1-19.
Baccanari et al., "Inhibition of dihydrofolate reductase: effect of reduced nicotinamide adenine dinucleotide phosphate on the selectivity and affinity of diaminobenzylpyrimidines", Biochemistry 21, 5068-5075 (1982).
Banaszynski et al., "Chemical control of protein stability and function in living mice", Nat Med 14, 1123-1127 (2008).
(Continued)

*Primary Examiner* — Michael G. Hartley
*Assistant Examiner* — Jagadishwar R Samala
(74) *Attorney, Agent, or Firm* — BakerHostetler

(57) ABSTRACT

The present invention provides radiolabeled trimethoprim which are useful in imaging tests such as PET scans. The compounds show robust bacterial uptake in vitro and identify infections from inflammation or tumor when administered to a subject. The compounds show rapid and sensitive detection of Ec DHFR containing tumors from control tumors and background tissue. In one aspect, a compound having the structure of formula (I) is provided or a pharmaceutically acceptable salt or prodrug thereof, wherein R is defined herein. Also provided are compositions containing these compounds, positron emission tomography reporter probe comprising these compounds, and methods of imaging a bacterial infection, tracking or monitoring bacteria, distinguishing a bacterial infection from inflammation or tumor, monitoring genetically fused protein expression, and monitoring genetically engineered cells in clinical scenarios such as immunotherapy for cancer treatment.

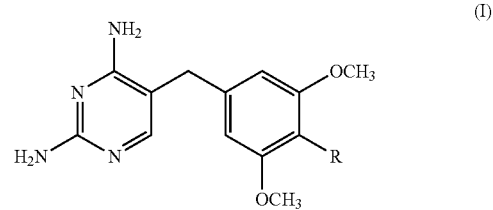

(I)

26 Claims, 25 Drawing Sheets

(56) References Cited

OTHER PUBLICATIONS

Bettegowda et al., "Imaging bacterial infections with radiolabeled 1-(2'-deoxy-2'-fluoro-beta-D-arabinofuranosyl)-5-iodouracil", Proc. Natl. Acad. Sci. U.S.A., vol. 102, 2005, 1145-1150.
Calloway et al., "Optimized Flourescent Trimethoprim Derivatives for in vivo Protein Labeling", ChemBioChem, May 2007, 8, 767-774.
Calloway et al., ChemBioChem, 2007, 8, 767-774.
Chan et al., "Design, Synthesis, and Antifolate Activity of New Analogues of Piritrexim and Other Diaminopyrimidine Dihydrofolate Reductase Inhibitors with a-Carboxyalkoxy or a-Carboxy-1-alkynyl Substitution in the Side Chain", J. Med Chem., 2005, 48, 4420-4431.
Collins et al., "PET imaging for gene & cell therapy", Current gene therapy 12, 20-32 (2012).
Diaz et al., "Imaging of Musculoskeletal Bacterial Infections by [124I]FIAU-PET/CT", PLoS ONE, vol. 2, Public Library of Science, 2007, e1007.
Diniz et al., "Scintigraphic imaging using technetium-99m-labeled ceftizoxime in an experimental model of acute osteomyelitis in rats", Nucl Med Commun., vol. 29, 2008, 830-836.
Dukowicz et al., "Small intestinal bacterial overgrowth: a comprehensive review", Gastroenterol Flepatol (NY), vol. 3 112-122 (2007).
Gallego et al., "Simultaneous Determination of Dexamethasone and Trimethoprim by Liquid Chromatography", J. Pharm. And Biomedical Analysis, 2002, 30, 1255-1261.
Gaynes R, Edwards Jr, "National Nosocomial Infections Surveillance S. Overview of nosocomial infections caused by gram-negative bacilli", Clinical infectious diseases : an official publication of the Infectious Diseases Society of America, 2005, 41, 848-854.
Gemmel et al., "Future Diagnostic Agents", Seminars in Nuclear Medicine, 2009, 39, 11-26.
Gibreel et al., "High-level resistance to trimethoprim in clinical isolates of Campylobacter jejuni by acquisition of foreign genes (dfrl and dfr9) expressing drug-insensitive dihydrofolate reductases", Antimicrob. Agents Chemother, vol. 42, 1998, 3059-3064.
Guo et al, "In vivo bioluminescence imaging to evaluate systemic and topical antibiotics against community-acquired methicillin-resistant Staphylococcus aureus-infected skin wounds in mice", Antimicrob. Agents Chemother., vol. 57 855-863 (2013).
Ingebrigtsen et al., "A study on melanin affinity of 14C-trimethoprim in male Mol:WIST and Mol:PVG rats", Zeitschrift fur Versuchstierkunde 33, 73-77 (1990).
Iwamoto, "A General Chemical Method to Regulate Protein Stability in the Mammalian Central Nervous System", Chem. Biol., Sep. 24, 2010, 17, 981-988.
Jing et al., "A Fluorogenic TMP-tag for High Signal-to-Background Intracellular Live Cell Imaging", Supporting Information, ACS, 2013, S1-S21.
Jing et al., "A Fluorogenic TMP-Tag for Signal-to-Background Intracellular Live Cell Imaging", ACS Chemical Biology, 2013, 8, 1704-1712.
Kalos, et al. T cells with chimeric antigen receptors have potent antitumor effects and can establish memory in patients with advanced leukemia. Sci Transl Med, vol. 3 95ra73 (2011).
Kremers et al., "Pharmacokinetic studies of co-trimoxazole in man after single and repeated doses", J Clin Pharmacol, vol. 14 112-117 (1974).
Langer et al., "In vitro and in vivo evaluation of [18F]ciprofloxacin for the imaging of bacterial infections with PET", Eur. J. Nucl. Med. Mol. Imaging, vol. 32, Springer-Verlag, 2004, 143-150.
Mali et al., "RNA-guided human genome engineering via Cas9", Science, vol. 339 823-826 (2013).

Maseda et al., "Assignment of the substrate-selective subunits of the MexEF-OprN multidrug efflux pump of Pseudomonas aeruginosa", Antimicrob. Agents Chemother. vol. 44. 2000, 658-664.
Modutlwa et al., "Synthesis of deuterium-labelled drugs by hydrogen-deuterium (H-D) exchange using heterogeneous catalysis", Journal of Labelled Compounds and Radiopharmaceuticals, Sep. 1, 2010, vol. 53, No. 11-12, 686-692.
Ning et al., "Maltodextrin-based imaging probes detect bacteria in vivo with high sensitivity and specificity", Nat Mater., vol. 10., 2011, 602-607.
Palestro et al., "Diagnostic imaging tests and microbial infections", Cell Microbiol, vol. 9, 2007, 2323-2333.
Palestro, "Radionuclide Imaging of Infection: In Search of the Grail", Journal of Nuclear Medicine, vol. 50., 2009, 671-673.
Patel et al., "Clinical pharmacokinetics of co-trimoxazole (trimethoprim-sulphamethoxazole)", Clinical pharmacokinetics 5, 405-423 (1980).
PUBCHEM, Substance Record for SID 172648919 Create Date: Mar. 2, 2014. [retrieved on Aug. 31, 2016]. Retrieved from the Internet: <https://pubchem.ncbi.nlm.nih.gov/substance/172648919>. entire document.
Reddy et al., "Luminescent Trimethoprim-Polyaminocarboxylate Lanthanide Complex Conjugates for Selective Protein Labeling and Time-Resolved Bioassays", Bioconjugate Chemistry, Jul. 20, 2011, vol. 22, No. 7, 1402-1409.
Sasser et al., "Bacterial infection probes and imaging strategies in clinical nuclear medicine and preclinical molecular imaging", Curr Top Med Chem, vol. 13, 2013, 479-487.
Siaens et al., "Synthesis and comparison of 99mTc-enrofloxacin and 99mTc-ciprofloxacin", J. Nucl. Med., vol. 45., 2004, 2088-2094.
Smal et al., "Selectively 13C-enriched 2,4-diamino-5-(3,4,5-trimethoxybenzyl)pyrimidine (trimethoprim) and 2,4-diaminopyrimidine", Journal of the Chemical Society, Perkin Transactions 1, Jan. 1, 1986, p. 747.
Tarassov et al., "An in vivo map of the yeast protein interactome", Science, vol. 320 1465-1470, 2008.
Taylor et al., "Recognition of hyaluronan released in sterile injury involves a unique receptor complex dependent on Toll-like receptor 4, CD44, and MD-2", J Biol Chem. vol. 282. 2007. 18265-18275.
Testa et al., "Prodrugs Revisited: The "Ad Hoc" Approach as a Complement to Ligand Design", Medicinal Research Reviews, May 1996, 16(3), 233-241.
Tokunaga et al., "Efficacy of trimethoprim in murine experimental infection with a thymidine kinase-deficient mutant of *Escherichia coli*", Antimicrob. Agents Chemother., vol. 41, 1042-1045 (1997).
Umov et al., "Highly efficient endogenous human gene correction using designed zinc-finger nucleases", Nature 435, 646-651 (2005).
Van Oosten et al., "Real-time in vivo imaging of invasive- and biomaterial associated bacterial infections using fluorescently labelled vancomycin", Nat Comms. vol. 4., 2013.
Vilcheze, C. & Jacobs, W. R. "The Combination of Sulfamethoxazole, Trimethoprim, and Isoniazid or Rifampin Is Bactericidal and Prevents the Emergence of Drug Resistance in Mycobacterium Tuberculosis", Antimicrob. Agents Chemother. 56, 5142-5148 (2012).
Volpato et al., "Mutational 'hot-spots' in mammalian, bacterial and protozoal dihydrofolate reductases associated with antifolate resistance: sequence and structural comparison", Drug resistance updates : reviews and commentaries in antimicrobial and anticancer chemotherapy 12, 28-41 (2009).
Waerzeggers, et al. "Methods to monitor gene therapy with molecular imaging", Methods 48, 146-160 (2009).
Wei et al., "dfrA27, a new integron-associated trimethoprim resistance gene from *Escherichia coli*", Journal of Antimicrobial Chemotherapy, vol. 63, 2008, 405-406.
Wing et al., "Chronic osteomyelitis examined by CT", Radiology, 1985, 154, 171-174.
Youn et al., "Reporter gene imaging", AJR Am J Roentgenol, vol. 201 W206-214 (2013).
Yu et al., "Quantification of target gene expression by imaging reporter gene expression in living animals", Nat. Med., vol. 6 933-937 (2000).

\* cited by examiner

RADIOTRACER DERIVATIVES OF TRIMETHOPRIM FOR DIAGNOSTIC IMAGING

CROSS REFERENCE TO RELATED APPLICATIONS

This application is a divisional of U.S. patent application Ser. No. 15/572,632, filed Nov. 8, 2017, which is the U.S. national stage of International Patent Application No. PCT/US2016/031600, filed May 10, 2016, which claims the benefit of the priority of U.S. Provisional Patent Application No. 62/159,327, filed May 10, 2015, each application of which is incorporated herein by reference.

TECHNICAL FIELD

This invention relates to the field of radiolabeled derivatives of trimethoprim for diagnostic imaging.

BACKGROUND

Imaging nuclear medicine techniques such as WBC or gallium scanning may be used to identify areas of inflammation or infection. However, their use is infrequent due to their inherent technical and protocol challenges as well as poor spatial imaging resolution. Furthermore, these techniques rely on secondary sequelae of bacterial infection and consequent inflammation rather than binding the bacteria directly leading to ambiguity of correct diagnosis of true bacterial infection.

These limitations are particularly evident in cases where a patient has a bacterial infection, but no known methods are available to locate the area of bacterial infection in the patient without misdiagnosing areas of inflammation. For example, it is difficult distinguishing bacterial pneumonia from aspiration chemical pneumonitis. Nor are there any reliable techniques for distinguishing a bacterial infection from another infection that presents with similar symptoms. For example, it is difficult distinguishing bacterial pneumonia from viral infection. Nor are there any reliable techniques for distinguishing a bacterial infection from tumor. For example, it is difficult distinguishing bacterial infection from recurrent or metastatic cancer in the lungs. In all of these cases, excessive amounts of incorrect antibiotics may be administered to the patient contributing the problem of antibiotic resistant organisms. Additionally, inappropriate biopsies may occur in cases of diagnostic ambiguity, thereby resulting in high treatment costs, and the possibility of procedural complications. What is needed in the art is the development of better quantitative imaging tools to monitor bacteria in humans.

There is an unmet clinical need for improved methods to track engineered cells, including immune cells used for cell-based therapy and adoptive immunotherapy. Also needed are better quantitative imaging tools to monitor gene and cell therapies.

SUMMARY OF THE INVENTION

In one aspect, a compound having the structure of formula (I) is provided or a pharmaceutically acceptable salt or prodrug thereof, wherein R is defined herein.

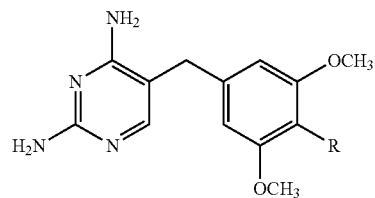

In another aspect, a composition is provided and comprises a compound described herein, or a pharmaceutically acceptable salt or prodrug thereof, and a pharmaceutically acceptable carrier or diluent.

In a further aspect, a method of imaging a bacterial infection in a subject is provided. The method includes (a) administering an effective amount of a compound described herein, or a pharmaceutically acceptable salt or prodrug thereof, to the subject; and (b) tracking the compound. In one embodiment, the method distinguishes infection from inflammation or tumor.

In yet another aspect, a method of tracking or monitoring bacteria in a subject is provided. The method includes (a) administering an effective amount of a compound, or a pharmaceutically acceptable salt or prodrug thereof, to the subject; and (b) tracking the compound.

In a further aspect, a method of monitoring treatment of a bacterial infection in a subject is provided. The method includes (a) administering an antibiotic to the subject; (b) administering an effective amount of a compound, or a pharmaceutically acceptable salt or prodrug thereof, described herein to the subject; and (c) tracking the compound.

In another aspect, a method of monitoring treatment of cancer in a subject is provided and includes (a) administering a chemotherapeutic, radiation, or immunotherapy to the subject; (b) administering an effective amount of a compound described herein, or a pharmaceutically acceptable salt or prodrug thereof, to the subject; and (c) tracking the compound.

In yet a further aspect, a method of monitoring immunotherapy in a subject is provided. The method includes (a) genetically engineering cells from said the to express dihydrofolate reductase (DHFR); (b) tagging the engineered cells with a compound described herein, or a pharmaceutically acceptable salt or prodrug thereof; (c) administering the genetically engineered and tagged cells to the patient; and (d) tracking the genetically engineered cells and tagged by imaging.

In still another aspect, a positron emission tomography reporter probe is provided and comprises a compound described herein, or a pharmaceutically acceptable salt or prodrug thereof.

In a further aspect, a method of preparing the following compound is provided.

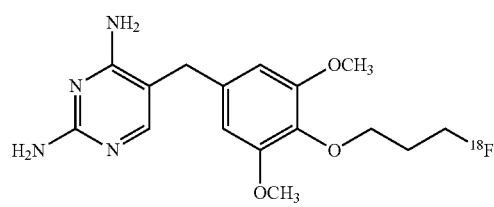

Other aspects and embodiments of the invention will be readily apparent from the following detailed description of the invention.

BRIEF DESCRIPTION OF THE DRAWINGS

The present application is further understood when read in conjunction with the appended drawings. For the purpose of illustrating the subject matter, there are shown in the drawings exemplary embodiments of the subject matter; however, the presently disclosed subject matter is not limited to the specific compositions, methods, devices, and systems disclosed. In addition, the drawings are not necessarily drawn to scale.

DETAILED DESCRIPTION OF THE INVENTION

Trimethoprim (TMP) is a small molecule antibiotic routinely used in the clinic that has high affinity and specificity for the *E. coli* dihydrofolate reductase enzyme (Ec DHFR), a bacterial protein involved in DNA synthesis that is highly genetically conserved across many bacterial species. The Ec DHFR protein is a small, 159 residue, 18 kDa essential enzyme involved in DNA and amino acid synthesis in all living organisms that is often used in biochemical studies and protein engineering tools.

To date, there is no single agent that provides a facile and repeatable imaging tool for long term tracking of engineered cells, an increasingly important mode of therapy for cancer and other diseases. It is additionally apparent that multiple genetic reporter genes capable of imaging and tracking multiple types of cells are needed as the complexity of cell therapy advances.

Figure 1:
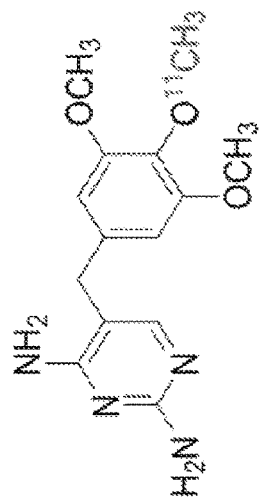
FIG. 1 is a diagram of TMP as a PET radiotracer coupled with Ec DFHR reporter gene in mammalian cells.
Figure 1:
Figure 1:
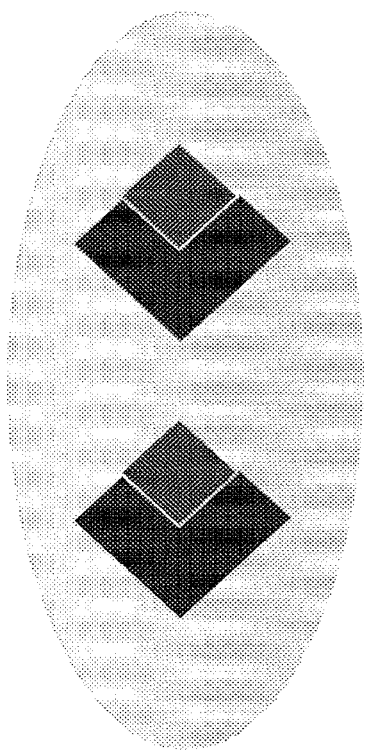
Figure 1:
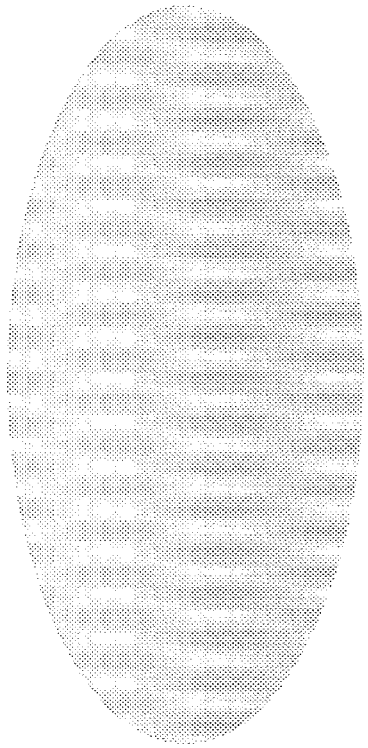

The TMP radiolabeled compounds described have high specificity for DHFR at very low concentrations. FIG. 1 is a diagram of TMP as a PET radiotracer coupled with Ec DFHR reporter gene. The compounds described herein permit efficient diagnosis thereby suggesting significant downstream cost differences. Specifically, the ability of the compounds described herein, due to their efficacy in identifying locations of infection, may lead to the use of fewer and less antibiotics, appropriate care for patients, reduced lengths of hospital stays, and avoidance of unnecessary surgery and biopsy. In one embodiment, if there is increased signal after compound administration from an area of clinical concern when compared to appropriate control tissue, the increased signal correlates which a highly suggestion of bacterial infection.

The compounds discussed herein have a wide range of uses. In one embodiment, the compounds are capable of imaging bacteria, both commensal and infectious. In another embodiment, the compounds may be used as a positron emission tomography (PET) reporter probe for imaging transgenic cells. The binding and retention of TMP by Ec DHFR will allow for clearance of non-bound probe providing high contrast imaging of bacteria or transgenic cells carrying Ec DHFR in whole animals or humans. The ability to longitudinally and non-invasively monitor basic bacterial infections such as pneumonia, osteomyelitis, cystic fibrosis superinfection or transgene expression in engineered cells used for cancer immunotherapy would be a powerful, groundbreaking advance beyond current standard PET imaging technologies and could revolutionize the diagnostic imaging armamentarium for many related clinical settings.

In the present disclosure the singular forms "a", "an" and "the" include the plural reference, and reference to a particular numerical value includes at least that particular value, unless the context clearly indicates otherwise. Thus, for example, a reference to "a material" is a reference to at least one of such materials and equivalents thereof known to those skilled in the art, and so forth.

When a value is expressed as an approximation by use of the descriptor "about" or "substantially" it will be understood that the particular value forms another embodiment. In general, use of the term "about" or "substantially" indicates approximations that can vary depending on the desired properties sought to be obtained by the disclosed subject matter and is to be interpreted in the specific context in which it is used, based on its function. The person skilled in the art will be able to interpret this as a matter of routine. In some cases, the number of significant figures used for a particular value may be one non-limiting method of determining the extent of the word "about" or "substantially". In other cases, the gradations used in a series of values may be used to determine the intended range available to the term "about" or "substantially" for each value. Where present, all ranges are inclusive and combinable. That is, references to values stated in ranges include every value within that range.

When a list is presented, unless stated otherwise, it is to be understood that each individual element of that list and every combination of that list is to be interpreted as a separate embodiment. For example, a list of embodiments presented as "A, B, or C" is to be interpreted as including the embodiments, "A," "B," "C," "A or B," "A or C," "B or C," or "A, B, or C."

It is to be appreciated that certain features of the invention which are, for clarity, described herein in the context of separate embodiments, may also be provided in combination in a single embodiment. That is, unless obviously incompatible or excluded, each individual embodiment is deemed to be combinable with any other embodiment(s) and such a combination is considered to be another embodiment. Conversely, various features of the invention that are, for brevity, described in the context of a single embodiment, may also be provided separately or in any sub-combination. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Finally, while an embodiment may be described as part of a series of steps or part of a more general structure, each said step may also be considered an independent embodiment in itself.

I. THE COMPOUNDS

As discussed above, the compounds herein are radiolabeled with a radiotracer ligand. The radiotracer ligand is one that is sufficiently stable to permit binding to TMP and subsequent administration to a patient. In one embodiment, the compound is a radiolabeled TMP. In another embodiment, the compound has the structure of formula (I) or a pharmaceutically acceptable salt or prodrug thereof:

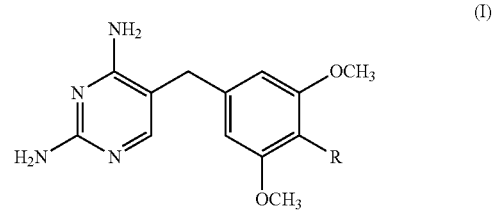

In this structure, R is $—O—C^{11}—(C_1$ to $C_6$ alkyl), an $O—C^{11}$-glycol, $O—(C_1$ to $C_6$ alkyl)$-^{18}F$, $—OCH_2—(^{18}F$ substituted phenyl), $—OCH_2CH_2—(^{18}F$-substituted triazole), $—OCH_2CH_2—(^{18}F$-substituted tetrazole), $^{18}F$-substituted boron-dipyrromethene, $—O(CH_2CH_2O)_nCH_2CH_2—$ $^{18}F$, $—OCH_2CH_2CH_2NHC(O)(CH_2CH_2O)_n—CH_2CH_2—$ $^{18}F$, $-L^1-^{68}Ga$, $-L^1-^{64}Cu$, $-L^1-^{99m}Tc$, radioactive halogen, $^{211}At$, $-L^1-^{10}B$, $-L^1-^{32}P$, $-L^1-^{90}Y$, $-L^1-^{103}Pd$, $-L^1-^{131}Cs$, $-L^1-^{153}Sm$, $-L^1-^{177}Lu$, $-L^1-^{211}At$, $-L^1-^{212}Bi$, $-L^1-^{212}Po$, $-L^1-^{212}Pb$, $-L^1-^{223}Ra$, or $-L^1-^{225}Ac$; n is 1-3; and $L^1$ is a linker; or a pharmaceutically acceptable salt or prodrug thereof.

In one embodiment, the radioactive halogen is $^{18}F$, $^{123}I$, $^{125}I$, $^{124}I$, $^{131}I$, $^{32}Cl$, $^{33}Cl$, $^{34}Cl$, $^{74}Br$, $^{75}Br$, $^{76}Br$, $^{77}Br$, or 78Br.

In another embodiment, R is $O^{11}CH_3$.

In a further embodiment, R is $^{18}F$.

In yet other embodiments, $L^1$ is DTPA, HEHA, NOTA, DOTA, CHX-A, or TCMC.

In yet another embodiment, the compound has the following structure:

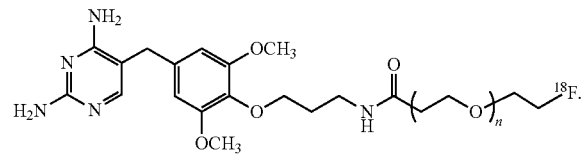

In still a further embodiment, the compound has the following structure:

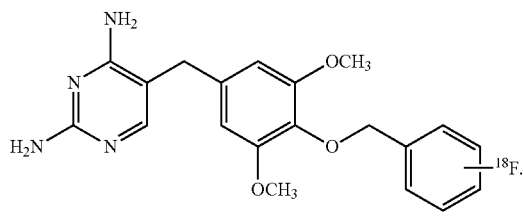

In another embodiment the compound has the following structure:

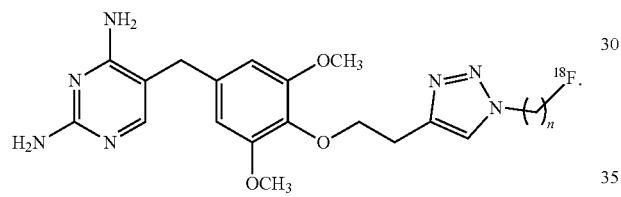

In a further embodiment, the compound has the following structure:

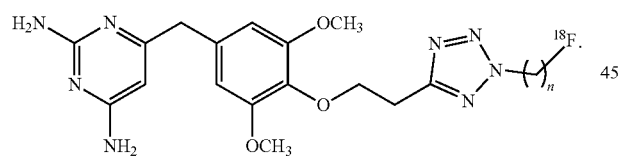

In another embodiment, the compound has the following structure:

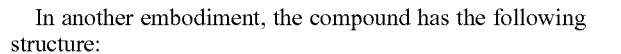

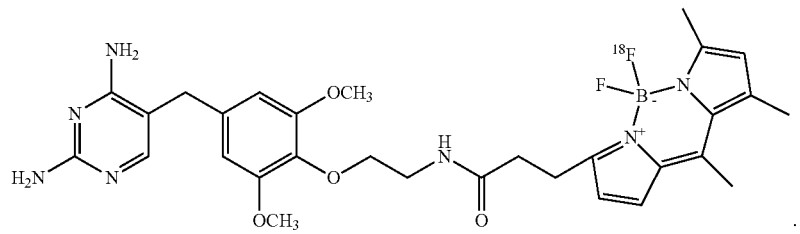

In yet a further embodiment, the compound has the following structure:

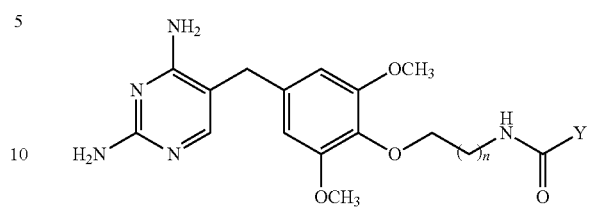

wherein, n is 1 to 6; and Y is

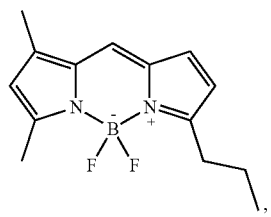

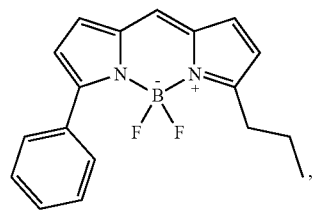

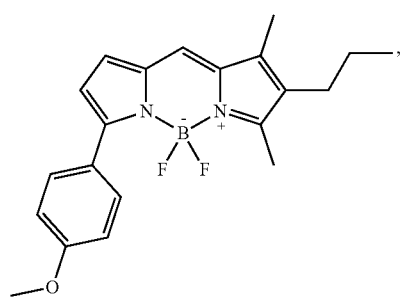

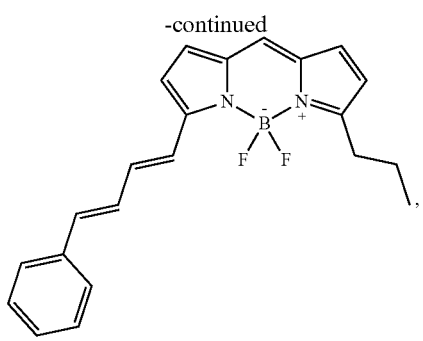

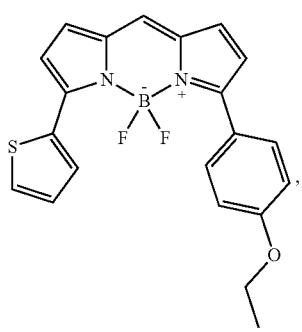

, or

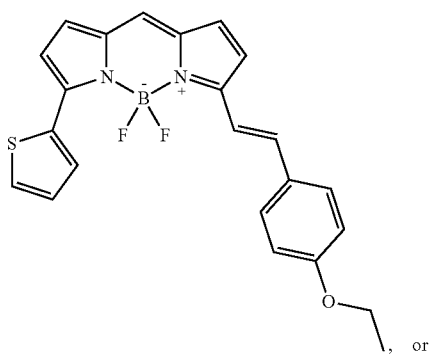

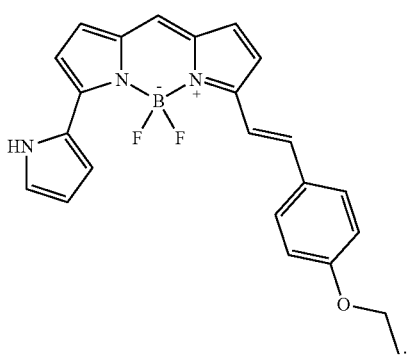

.

In still another embodiment, $^{64}$Cu, $^{68}$Ga, $^{10}$B, $^{32}$P, $^{90}$Y, $^{103}$Pd, $^{131}$Cs, $^{153}$Sm, $^{177}$Lu, $^{211}$At, $^{212}$Bi, $^{212}$Po, $^{223}$Pb, $^{223}$Ra, or $^{225}$Ac is chelated.

In a further embodiment, wherein the chelation is performed using:

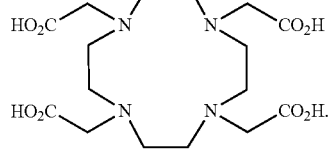

(DOTA)

In another embodiment, the chelation is performed using:

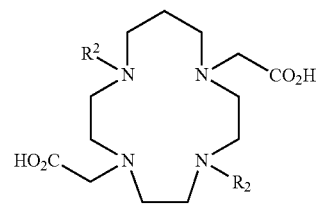

wherein, $R^2$ is, independently, H or $CH_2CO_2H$.

In a further embodiment, the chelation is performed using:

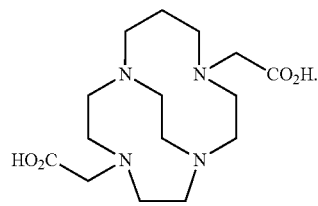 [SMILES: O=C(O)CN1CCCN2CCN(CC1)CCN(CC(=O)O)CC2]

In another embodiment, the chelation is performed using:

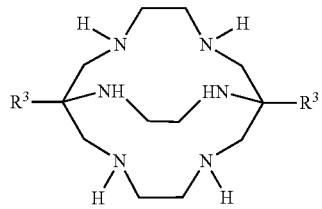

wherein, $R^3$ is, independently, H or $NH_2$.

In yet a further embodiment, the chelation is performed using:

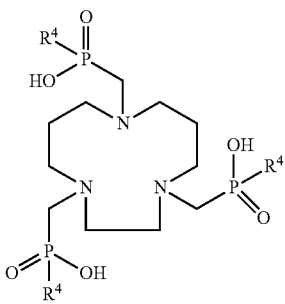

wherein, $R^4$ is, independently, H, —$(CH_2)_2CO_2H$, $CH_2OH$, or phenyl.

In still another embodiment, the chelation is performed using:

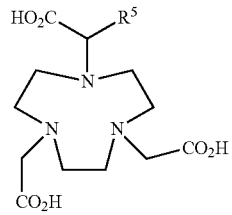

wherein, $R^5$ is H or —$(CH_2)_2CO_2H$.

In a further embodiment, the chelation is performed using:

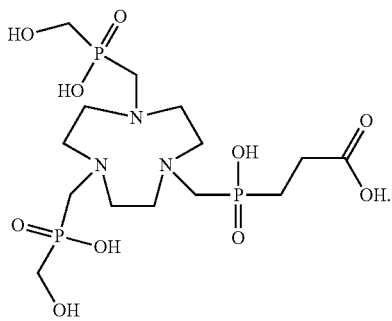 [SMILES: O=C(O)CCP(=O)(O)CN1CCN(CP(=O)(O)CO)CCN(CP(=O)(O)CO)CC1]

In yet a further embodiment, the chelation is performed using:

(NOTA)

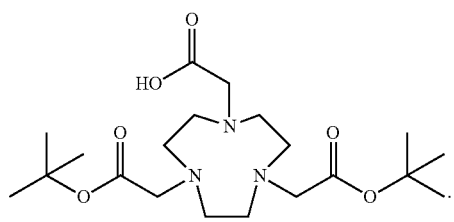

In still another embodiment, the chelation is performed using:

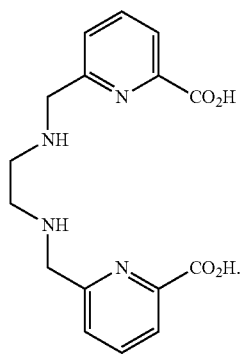 [SMILES: O=C(O)c1cccc(CNCCNCc2cccc(C(=O)O)n2)n1]

In a further embodiment, R is:

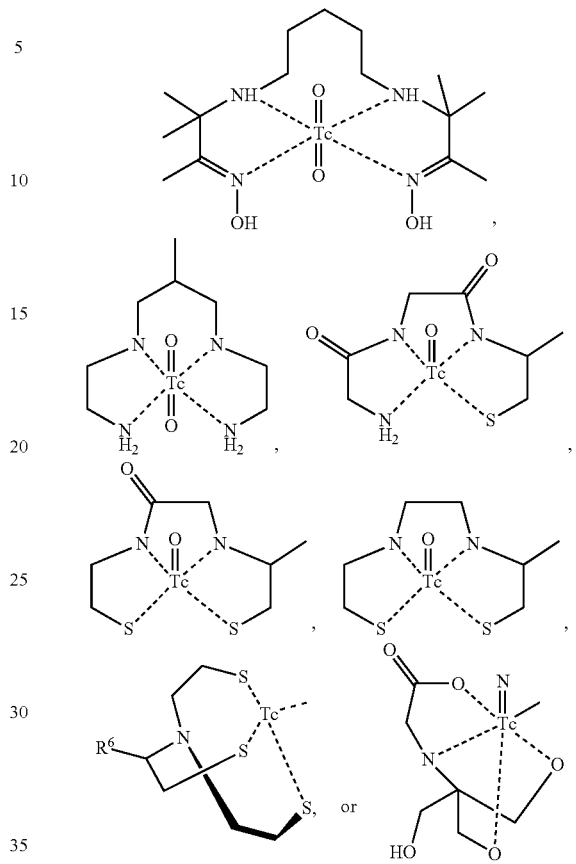

wherein, $R^6$ is alkyl or alkoxy.

In this structure, R contains a radioactive isotope. In one embodiment, the radioactive isotope is bound directly to the TMP base molecule. In another embodiment, the radioactive isotope is bound to the base molecule through another chemical moiety. In a further embodiment, the radioactive isotope is a radiolabeled halogen, radiolabeled alkoxy, radiolabeled, glycol, or radiolabeled alkyl group. In yet another embodiment, the radiolabel is —$O^{11}$—($C_1$ to $C_6$ alkyl), a -glycol-$^{11}CH_3$, —($C_1$ to $C_6$ alkyl)-$^{18}F$, $^{18}F$, $^{123}I$, $^{125}I$, $^{124}I$, $^{131}I$, $^{32}Cl$, $^{33}Cl$, $^{34}Cl$, $^{74}Br$, $^{75}Br$, $^{76}Br$, $^{77}Br$, $^{78}Br$, $^{64}Cu$ and $^{68}Ga$, or radiotherapeutic radioisotopes including $^{10}B$, $^{32}P$, $^{90}Y$, $^{103}Pd$, $^{131}Cs$, $^{153}Sm$, $^{177}Lu$, $^{211}At$, $^{212}Bi$, $^{212}Po$, $^{212}Pb$, $^{223}Ra$, or $^{225}Ac$. In still a further embodiment, the radiolabel is O—$^{11}CH_3$ or $CH_2CH_2CH_2^{18}F$. In yet another embodiment, the radiolabel is —($C_1$ to $C_6$ alkoxy amido)-chelated $^{64}Cu$ or —($C_1$ to $C_6$ alkoxy amido)-chelated $^{68}Ga$. In still a further embodiment, the radiolabel is -DOTA-$^{64}Cu$ or -NOTA-$^{68}Ga$. In other embodiments, the radiotherapeutic radioisotope is chelated.

The term "glycol" as used herein refers to an organic compound have two hydroxyl groups, each hydroxyl being attached to different carbon atoms. In one embodiment, the glycol is ethylene glycol, propylene glycol, 1,3-butanediol, 1,4-butanediol, 2-ethyl-1,3-hexanediol, 2-methyl-2-propyl-1,3-propanediol, polyglycols, among others. One or more hydrogen bound to the carbon atom may be substituted with a radioactive isotope described herein.

The term "alkyl" is used herein to refer to both straight- and branched-chain saturated aliphatic hydrocarbon groups.

In one embodiment, an alkyl group has 1 to about 10 carbon atoms. In another embodiment, an alkyl group has 1 to about 6 carbon atoms. In a further embodiment, an alkyl group has 1 to about 4 carbon atoms. The alkyl group may be optionally substituted with one or more radiolabel as provided above.

The term "alkoxy" as used herein refers to the O-(alkyl) group, where the point of attachment is through the oxygen-atom and the alkyl group is defined above. The alkoxy group may be optionally substituted with one or more radiolabel as provided above.

The term "halogen" as used herein refers to Cl, Br, F, or I groups.

II. METHODS OF PRODUCTION

The compounds described above may be prepared by known chemical synthesis techniques. Among such preferred techniques known to one of skill in the art are included the synthetic methods described in conventional textbooks relating to the construction of synthetic compounds. [$^{11}$C]Trimethoprim ([$^{11}$C]TMP) and [$^{18}$F]Fluoropropyltrimethoprim ([$^{18}$F]FP-TMP) may be prepared as described in the examples and according to the following.

A. [$^{11}$C]TMP

[$^{11}$C]TMP was prepared using skill in the art and the steps outlined in Scheme 1 and Example 1.

Scheme 1

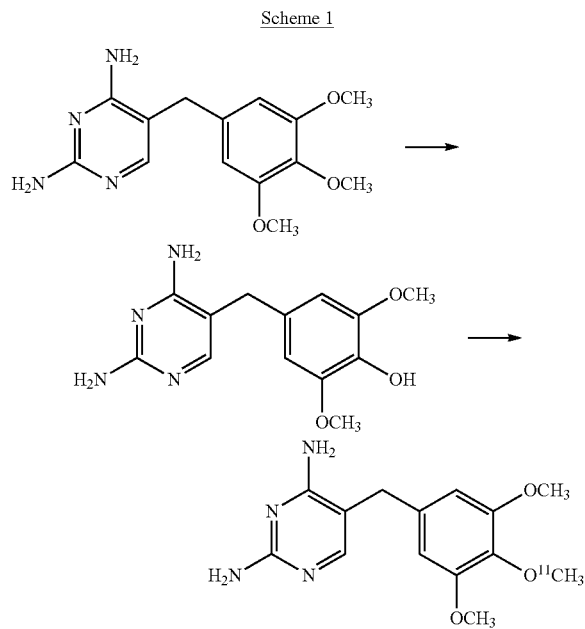

[$^{11}$C]TMP was prepared using intermediate 5-(3,5-dimethoxy-4-hydroxy-benzyl)pyrimidine-2,4-diamine using the procedure in *Chem. Bio. Chem.*, 2007, 8:767-774. See, Scheme 1. In one embodiment, trimethoprim (3 g, 10.03 mmol, purchased from Sigma-Aldrich) is selectively demethylated by HBr (48% in water) for 20 min at 95° C. After the reaction, the reaction mixture was cooled down and NaOH (8.92 mL, 50% w/w) added. After precipitation, the precipitate was filtered and collected, and re-dissolved in boiling water. NH$_4$OH was added to the mixture solution until pH 7, recrystallized at 4° C., filtered, and collected. 5-(3,5-dimethoxy-4-hydroxy-benzyl)pyrimidine-2,4-diamine was obtained as a pink solid (1.51 g) in 52.9% yield;

$^1$H NMR (DMSO-d$_6$) δ 8.06 (s, —OH), 7.45 (s, 1H), 6.48 (s, 2H), 5.99 (s, —NH$_2$), 5.63 (s, —NH$_2$), 3.71 (s, 6H), 3.47 (s, 2H). Followed by next step, 5-(3,5-dimethoxy-4-hydroxy-benzyl)pyrimidine-2,4-diamine was reacted with [$^{11}$C]CH$_3$I for 5 min at 70° C. in the present of 5 N NaOH (4 μL) as a base. After the reaction, the reaction mixture was purified by HPLC with 12% EtOH in 0.01 M Phosphate buffer (pH=3). The flow rate of HPLC was 3 mL/min and the product ([$^{11}$C]TMP) was eluted at 12 min retention time. The radiochemical yield was 40-50% from [$^{11}$C]CH$_3$I, radiochemical purity was over 99%, and the specific activity was 37-56 GBq/μmol.

[$^{11}$C]TMP has a half-life of about 20.4 minutes. In one embodiment, [$^{11}$C]TMP is synthesized at a facility having a cyclotron.

There are also key advantages to using [$^{11}$C]TMP as a radiotracer. First, the synthetic route to [$^{11}$C]TMP is only two-steps and facile. The precursor is inexpensive and widely available. TMP as an antibiotic is often used clinically in combination with sulfamethoxazole and thus the toxicity profile is well known. Since [$^{11}$C]TMP is the same chemical structure as the unlabeled antibiotic, this tracer may be rapidly applied into patients. TMP radiotracer imaging may have a much lower background as the target (bacterial DHFR) is not native to human cells. This leads to high sensitivity imaging, for example 3×10$^5$ cells implanted were detected, which is a clinically relevant concentration based on current therapies which typically implant greater than 10$^7$ cells.

Other advantages of [$^{11}$C]TMP include the ability to possibly cross the blood brain barrier. By doing so, [$^{11}$C] TMP may be utilized for visualizing cells in areas of high background for reporter proteins derived from nervous system tissue (e.g. hNET and D2R) or in cases where alternative small molecule probes do not adequately cross the blood brain barrier.

Other radiolabeled alkyl groups may be incorporated into the para position in place of $^{11}$CH$_3$. In one embodiment, one or more carbon atoms of the alkyl group contains a $^{11}$C atom.

B. [$^{18}$F]FP-TMP

The inventors also found the synthesis route of $^{18}$F-radiolabeled derivatives of TMP. Of importance, the inventors finally found that substituting the O-atom at the para position of the benzene ring with a longer chain permitted $^{18}$F labeling. In one embodiment, the para-position O-atom is substituted with an alkoxylated silate. In another embodiment, the para-position O-atom was substituted with 3-bromopropoxy-tert-butyldimethyl silate. This step is important to attach alkoxy linker of 4-hydroxyl group in benzene ring for TMP compound, can be purified by flash column and selectively deprotected for TBDMS group without any effect of Boc protecting group. Accordingly, one method of preparing the following $^{18}$F-radiolabeled derivative was performed as described herein.

The inventors found that [$^{18}$F]Fluoropropyl trimethoprim has a 110 min half-life. This longer shelf life advantageously permits increased incubation time of the compound with the target bacteria with less loss of signal due to isotope decay. Further, this also permits metabolic clearance of the compound.

III. COMPOSITIONS CONTAINING THE COMPOUND

Pharmaceutical compositions useful herein, in one embodiment, contain a compound discussed above in a pharmaceutically acceptable carrier or diluent with other optional suitable pharmaceutically inert or inactive ingredients. In another embodiment, a compound described above is present in a single composition. In a further embodiment, a compound described above is combined with one or more excipients and/or other therapeutic agents as described below.

(i) Salts

The compounds discussed above may encompass tautomeric forms of the structures provided herein characterized by the bioactivity of the drawn structures. Further, the compounds may also be used in the form of salts derived from pharmaceutically or physiologically acceptable acids, bases, alkali metals and alkaline earth metals.

In one embodiment, pharmaceutically acceptable salts can be formed from organic and inorganic acids including, e.g., acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable acids.

In another embodiment, pharmaceutically acceptable salts may also be formed from inorganic bases, desirably alkali metal salts including, e.g., sodium, lithium, or potassium, such as alkali metal hydroxides. Examples of inorganic bases include, without limitation, sodium hydroxide, potassium hydroxide, calcium hydroxide, and magnesium hydroxide. Pharmaceutically acceptable salts may also be formed from organic bases, such as ammonium salts, mono-, di-, and trimethylammonium, mono-, di- and triethylammonium, mono-, di- and tripropylammonium, ethyldimethylammonium, benzyldimethylammonium, cyclohexylammonium, benzyl-ammonium, dibenzylammonium, piperidinium, morpholinium, pyrrolidinium, piperazinium, 1-methylpiperidinium, 4-ethylmorpholinium, 1-isopropylpyrrolidinium, 1,4-dimethylpiperazinium, 1-n-butyl piperidinium, 2-methylpiperidinium, 1-ethyl-2-methylpiperidinium, mono-, di- and triethanolammonium, ethyl diethanolammonium, n-butylmonoethanolammonium, tris (hydroxymethyl)methylammonium, phenylmono-ethanolammonium, diethanolamine, ethylenediamine, and the like. In one example, the base is selected from among sodium hydroxide, lithium hydroxide, potassium hydroxide, and mixtures thereof.

(ii) Prodrugs

The salts, as well as other compounds, can be in the form of esters, carbamates and other conventional "pro-drug" forms, which, when administered in such form, convert to the active moiety in vivo. In one embodiment, the prodrugs are esters. In another embodiment, the prodrugs are carbamates. See, e.g., B. Testa and J. Caldwell, "Prodrugs Revisited: The "Ad Hoc" Approach as a Complement to Ligand Design", Medicinal Research Reviews, 16(3):233-241, ed., John Wiley & Sons (1996), which is incorporated by reference.

(iii) Carriers and Diluents

The pharmaceutical compositions include a compound described herein formulated neat or with one or more pharmaceutical carriers for administration, the proportion of which is determined by the solubility and chemical nature of the compound, chosen route of administration and standard pharmacological practice. The pharmaceutical carrier may be solid or liquid.

The compound may be administered by any desirable route, taking into consideration the specific condition for which it has been selected. The compound may, therefore, be delivered orally, by injection, i.e., transdermal, intravenous, subcutaneous, intramuscular, intravenous, intra-arterial, intraperitoneal, intrathecal, intracavitary, or epidural, among others.

Although the compound may be administered alone, it may also be administered in the presence of one or more pharmaceutical carriers that are physiologically compatible. The carriers may be in dry or liquid form and must be pharmaceutically acceptable. Liquid pharmaceutical compositions are typically sterile solutions or suspensions.

When liquid carriers are utilized, they are desirably sterile liquids. Liquid carriers are typically utilized in preparing solutions, suspensions, emulsions, syrups and elixirs. In one embodiment, the compound is dissolved a liquid carrier. In another embodiment, the compound is suspended in a liquid carrier. One of skill in the art of formulations would be able to select a suitable liquid carrier, depending on the route of administration. In one embodiment, the liquid carrier includes, without limitation, water, organic solvents, oils, fats, or mixtures thereof. In another embodiment, the liquid carrier is water containing cellulose derivatives such as sodium carboxymethyl cellulose. In a further embodiment, the liquid carrier is water and/or dimethylsulfoxide. Examples of organic solvents include, without limitation, alcohols such as monohydric alcohols and polyhydric alcohols, e.g., glycols and their derivatives, among others. Examples of oils include, without limitation, fractionated coconut oil, arachis oil, corn oil, peanut oil, and sesame oil and oily esters such as ethyl oleate and isopropyl myristate.

Alternatively, the compound may be formulated in a solid carrier. In one embodiment, the composition may be compacted into a unit dose form, i.e., tablet or caplet. In another embodiment, the composition may be added to unit dose form, i.e., a capsule. In a further embodiment, the composition may be formulated for administration as a powder. The solid carrier may perform a variety of functions, i.e., may perform the functions of two or more of the excipients described below. For example, the solid carrier may also act as a flavoring agent, lubricant, solubilizer, suspending agent, filler, glidant, compression aid, binder, disintegrant, or encapsulating material. Suitable solid carriers include, without limitation, calcium phosphate, dicalcium phosphate, magnesium stearate, talc, starch, sugars (including, e.g., lactose and sucrose), cellulose (including, e.g., microcrystalline cellulose, methyl cellulose, sodium carboxymethyl cellulose), polyvinylpyrrolidine, low melting waxes, ion exchange resins, and kaolin. The solid carrier can contain other suitable excipients, including those described below.

Examples of excipients which may be combined with the compound include, without limitation, adjuvants, antioxidants, binders, buffers, coatings, coloring agents, compression aids, diluents, disintegrants, emulsifiers, emollients, encapsulating materials, fillers, flavoring agents, glidants, granulating agents, lubricants, metal chelators, osmo-regulators, pH adjustors, preservatives, solubilizers, sorbents, stabilizers, sweeteners, surfactants, suspending agents, syrups, thickening agents, or viscosity regulators. See, the excipients described in the "Handbook of Pharmaceutical Excipients", 5$^{th}$ Edition, Eds.: Rowe, Sheskey, and Owen, APhA Publications (Washington, D.C.), Dec. 14, 2005, which is incorporated herein by reference.

IV. METHODS OF USING THE COMPOUND

As discussed above, the radiolabeled compound have potential in a wide scope of applications including, without limitation, imaging a bacterial infection, tracking or monitoring bacteria, distinguishing a bacterial infection from inflammation, treating a bacterial infection, immunotherapy, and treating cancer. As described herein, a therapeutically or prophylactically effective amount of a compound is that amount of a compound which provides a sufficient amount of radiation. The effective amount of may be determined by the attending physician, formulation and route of delivery, condition treated, compound, route of delivery, age, weight, severity of the patient's symptoms, and response pattern of the patient. In one embodiment, effective amount does not exceed normal organ dose limits. In one embodiment, the effective amount is about 0.01 mg/kg to 10 mg/kg body weight. In another embodiment, the effective amount is less than about 5 g/kg, about 500 mg/kg, about 400 mg/kg, about 300 mg/kg, about 200 mg/kg, about 100 mg/kg, about 50 mg/kg, about 25 mg/kg, about 10 mg/kg, about 1 mg/kg, about 0.5 mg/kg, about 0.25 mg/kg, about 0.1 mg/kg, about 100 µg/kg, about 75 µg/kg, about 50 g/kg, about 25 µg/kg, about 10 µg/kg, or about 1 µg/kg.

A therapeutically or prophylactically effective amount of a compound may also be that amount of a compound which provides a sufficient amount of radiation. The sufficient amount of radiation may vary depending upon the formulation and route of delivery. In one embodiment, the amount (i.e., per unit) of the compound is that which does not exceed normal organ dose limits. In one embodiment, the compound delivers about 1 µCi to about 100 mCi of radiation. In other embodiments, the compound delivers about 1 µCi to about 50 mCi, or about 1 µCi to about 10 mCi, of radiation. However, the effective amount to be used is subjectively determined by the attending physician and variables such as the size, age and response pattern of the patient.

As used herein, "treatment" encompasses treatment of a subject clinically diagnosed as having a disease or medical condition. In one embodiment, the subject is treated and the disease or medical condition is eradicated, i.e., the subject is cured. As used herein, "prevention" encompasses prevention of symptoms in a subject who has been identified as at risk for the condition, but has not yet been diagnosed with the same and/or who has not yet presented any symptoms thereof.

These effective amounts may be provided on regular schedule, i.e., daily, weekly, monthly, or yearly basis or on an irregular schedule with varying administration days, weeks, months, etc. Alternatively, the effective amount to be administered may vary. In one embodiment, the effective amount for the first dose is higher than the effective amount for one or more of the subsequent doses. In another embodiment, the effective amount for the first dose is lower than the effective amount for one or more of the subsequent doses.

A. Imaging Methods

There is an unmet clinical need for improved detection and monitoring of bacteria in humans and animals. More specifically, better imaging agents are needed for distinguishing infection from inflammation or tumor. The compounds discussed herein may be utilized as imaging agents that permit visualization of bacteria in the body. Advantageously, the compounds do not image areas of inflammation or tumor. Accordingly, the methods herein are capable of distinguishing bacterial infection from inflammation or tumor. This is particularly useful in distinguishing chemical and/or aspiration pneumonitis or tumor versus bacterial pneumonia.

The compounds discussed herein show robust uptake in vitro and in vivo and, and favorable distribution and sensitivity. In some embodiments, the compounds permit non-invasively monitoring of less than 0.5 million engineered cells, which is an advance beyond the current PET report gene technologies.

Accordingly, the present invention provides methods of imaging a bacterial infection in a subject. The method includes administering an effective amount of a compound described herein and (b) tracking the radiolabeled derivative. By doing so, methods of tracking or monitoring bacteria are provided. Advantageously, the methods are first-in-class since they show robust uptake in gram positive and gram negative bacteria (*S. aureus* and *E. coli* respectively), show highly sensitive uptake in vitro, do not bind to heat killed bacteria, and permit distinguishing a bacterial infection from inflammation or tumor since the bacterial infection is displayed in the image whereas inflammation is absent.

The terms "patient" or "subject" as used herein refer to a mammalian animal. In one embodiment, the patient or subject is a human. In another embodiment, the patient or subject is a veterinary or farm animal, a domestic animal or pet, or animal normally used for clinical research. In still a further embodiment, the subject or patient has cancer. The subject or patient has either been recognized as having or at risk of having cancer.

The term "imaging" or "tracking" as used herein refers to any method of scanning the body of a subject using techniques such as positron emission tomography (PET) or single photon emission computed tomography (SPECT), among others. In one embodiment, the imaging displays areas of bacterial accumulation. In another embodiment, the imaging does not display areas of inflammation.

Of significance, the compounds and methods described herein permit distinguishing diseases/conditions which are often misdiagnosed as being due to bacterial infection. In one embodiment, the compounds and methods distinguish chemical or aspiration pneumonitis from bacterial pneumonia.

A number of different genera and species of bacteria may be imaged using the compounds and methods discussed herein. In one embodiment, the bacteria are sensitive to trimethoprim. In another embodiment, the bacterium is *E. coli, S. aureus, P. aureginosa, Enterobacter, Haemophilus, Klebsiella, Morganella, Proteus, Providencia, Salmonella, Serratia, Streptococcus* A, *Streptococcus* B, *Streptococcus* C, *Streptococcus* G, *Mycobacterium* TB, or any combination thereof. The bacteria may be commensal or infections. In one embodiment, the bacterial are gastrointestinal tract bacteria.

Not only are the compounds and methods useful in tracking bacteria, but they may be used in methods of monitoring treatment of a bacterial infection in a subject. In doing so, an antibiotic is administered to the subject using antibiotics known in the art. In one embodiment, the antibiotic is trimethoprim. An effective amount of a compound described may then be administered to the subject and the compound tracked to determine an approximate location of the infection. Alternatively, the compound is administered to the subject prior to administration of the antibiotic.

B. Immunotherapy Methods

Molecular biology tools are now capable of precise genome surgery, leading to a resurgence of targeted gene therapies for cancer and monogenic diseases. Current PET reporter genes are suboptimal and limited by its size, immunogenicity or genetic portability and off-target effects. Furthermore, many of the current PET or SPECT reporter proteins rely on either cell-surface (receptor) or enzymatic trapping of substrate which do not allow assessment of therapeutic protein expression levels. Accordingly, there is an unmet clinical need for improved methods to track engineered cells, including immune cells used for cell-based therapy and adoptive immunotherapy. To date, there is no single agent that provides a facile and repeatable imaging tool for long term tracking of engineered cells, an increasingly important mode of therapy for cancer and other diseases.

The compounds discussed herein fill this unmet need and may be used for imaging therapeutic cells and in methods of immunotherapy. The methods include genetically engineering cells from the patient to express dihydrofolate reductase. The engineered cells may then be tagged with a compound described herein. In one embodiment, the cells are transgenic cells carrying Ec DHFR. The genetically engineered and tagged cells may then be administered to the patient and tracked using techniques such as imaging.

Such genetic engineering may be performed using skill in the art. In one embodiment, the genetically engineering cells are T-cells, NK-cells, macrophages, B-cells, stem cells, hematopoietic stem cells, mesenchymal stem cells, neuroprogenitor cells, induced pluripotent cells, or any combinations thereof.

In one embodiment, the compounds may be used for tracking or treating cancer or gene editing for monogenic diseases such as sickle cell disease.

C. Additional Uses

The compounds discussed herein also have use in other applications. Accordingly, the compounds may be used in "problem-solving", i.e., when physician have difficulties determining a medical condition in a patient and traditional laboratory and imaging diagnostics have failed. For example, such conditions include, without limitation, cases of osteomyelitis or fever of unknown origin.

A significant "problem" which may be addressed by the compounds discussed herein include cancer. Accordingly, methods of treating cancer in a subject are provided and include initiating treatment of the cancer. In one embodiment, the subject is treated using a chemotherapeutic, radiation, or immunotherapy. The subject is then administered an effective amount of a compound described herein and the compound is tracked using imaging as previously described.

The term "cancer" as used herein, refers to neoplastic cells in a patient which have abnormal cell group and invade or have the potential to invade one or more body parts of the patient. In one embodiment, the cancer is a neuroendocrine cancer. In another embodiment, the cancer is of the adrenal gland, appendix, bladder, blood, brain, bone, breast, bronchus, central nervous system, cervix, chest, colon, esophagus, eye, gallbladder, head, intestines, kidney, larynx, liver, lung, lymph nodes, mouth, neck, ovaries, pancreas, pharynx, pituitary, prostate, rectum, skin, stomach, testicles, throat, thymus, thyroid, uterus, urinary tract, or vagina, or is a leukemia.

As noted above, the methods described herein may include administering a compound described herein via a combination therapy in prior to, concurrently with, or subsequent to another medication such as a chemotherapeutic. Accordingly, encompassed is a method of administration of chemotherapeutics, radiation, and/or immunotherapy in conjunction with a compound described herein. In one embodiment, the compound and chemotherapeutic, radiation, and/or immunotherapy are administered to the patient by one or more selected routes of administration sequentially. In another embodiment, a chemotherapeutic agent, radiation, and/or immunotherapy is administered before treatment with a compound described herein. In another embodiment, a chemotherapeutic agent, radiation, and/or immunotherapy is administered after treatment with a compound described herein. In still another embodiment, a chemotherapeutic agent, radiation, and/or immunotherapy is administered during treatment with a compound described herein.

The chemotherapeutic, radiation, and/or immunotherapy used to treat the cancer may be selected by one skill in the art.

In another embodiment, the compounds may be utilized in when the bacterial DHFR DNA is genetically attached to any gene of interest. Specifically, after standard transcription and translation, the protein target of the compound, bacterial DHFR, may be attached to the protein of interest. Imaging the compound provides the cellular concentration of the protein of interest. Advantageously, the genetic fusion of DHFR to a protein of interest does not affect protein of interest function. Examples of proteins include, without limitation, RAS, RAC, BAX, BRCA1, BRCA2, P53, RB, RHO, MTOR, or CAS9. See, Iwamoto, Chem. Biol., 17:981-988, 2010.

In a further embodiment, the compounds may be used as probes. In one embodiment, the probe is a PET reporter probe. In another embodiment, the compounds may be used prior to or after surgeries in an effort to determine if there is an existing bacterial infection and/or inflammation. The use of the compounds may be for a number of different types of surgeries including, without limitation, orthopedic surgery, abdominal, biliary, pancreatic, breast, prostate, GI, GU, endocrine, oncologic, neurologic, vascular, and podiatric surgery

V. KITS CONTAINING THE COMPOUND

Also provided herein are kits or packages of pharmaceutical formulations containing a compound or composition described herein. The kits may be organized to indicate a single formulation or combination of formulations to be taken at each desired time. The composition may also be sub-divided to contain appropriate quantities of the compound. For example, the unit dosage can be packaged compositions, e.g., packeted powders, vials, ampoules, prefilled syringes or sachets containing liquids.

Suitably, the kit contains packaging or a container with the compound formulated for the desired delivery route. Suitably, the kit contains instructions on dosing and an insert regarding the compound. Optionally, the kit may further contain instructions for monitoring circulating levels of product and materials for performing such assays including, e.g., reagents, well plates, containers, markers or labels, and the like. Such kits are readily packaged in a manner suitable for treatment of a desired indication. For example, the kit may also contain instructions for use of the delivery device. Other suitable components to include in such kits will be readily apparent to one of skill in the art, taking into consideration the desired indication and the delivery route. The doses are repeated daily, weekly, or monthly, for a predetermined length of time or as prescribed.

The compound or composition described herein can be a single dose or for continuous or periodic discontinuous administration. For continuous administration, a package or kit can include the compound in each dosage unit, e.g., solution, lotion, tablet, pill, or other unit described above or utilized in drug delivery. When the compound is to be delivered with periodic discontinuation, a package or kit can include placebos during periods when the compound is not delivered. When varying concentrations of a composition, of the components of the composition, or of relative ratios of the compound or other agents within a composition over time is desired, a package or kit may contain a sequence of dosage units, so varying.

A number of packages or kits are known in the art for the use in dispensing pharmaceutical agents for oral use. In one embodiment, the package has indicators for each period. In another embodiment, the package is a labeled blister package, dial dispenser package, or bottle.

The packaging means of a kit may itself be geared for administration, such as an inhalant, syringe, pipette, eye dropper, or other such like apparatus, from which the formulation may be applied to an infected area of the body, such as the lungs, injected into a subject, or even applied to and mixed with the other components of the kit.

The compound or composition of these kits also may be provided in dried or lyophilized forms. When reagents or components are provided as a dried form, reconstitution generally is by the addition of a suitable solvent. It is envisioned that the solvent also may be provided in another packaging means.

The kits may include a means for containing the vials in close confinement for commercial sale such as, e.g., injection or blow-molded plastic containers into which the desired vials are retained.

Irrespective of the number or type of packages, the kits also may include, or be packaged with a separate instrument for assisting with the injection/administration or placement of the ultimate complex composition within the body of an animal. Such an instrument may be an inhalant, syringe, pipette, forceps, measuring spoon, eye dropper or any such medically approved delivery means. Other instrumentation includes devices that permit the reading or monitoring of reactions in vitro.

In one embodiment, a pharmaceutical kit is provided and contains a compound of formula (I). The compound may be in the presence or absence of one or more of the carriers or excipients described above. The kit may optionally contain a chemotherapeutic and/or instructions for administering the chemotherapeutic and the compound to a subject having cancer.

In a further embodiment, a pharmaceutical kit is provided and contains a chemotherapeutic in a first dosage unit, one or more of a compound selected from those described herein in a second dosage unit, and one or more of the carriers or excipients described above in a third dosage unit. The kit may optionally contain instructions for administering the chemotherapeutic and/or compound to a subject having cancer.

The following Examples are provided to illustrate some of the concepts described within this disclosure. While each Example is considered to provide specific individual embodiments of composition, methods of preparation and use, none of the Examples should be considered to limit the more general embodiments described herein.

In the following examples, efforts have been made to ensure accuracy with respect to numbers used (e.g. amounts, temperature, etc.) but some experimental error and deviation should be accounted for. Unless indicated otherwise, temperature is in degrees C., pressure is at or near atmospheric.

VI. EMBODIMENTS

Embodiment 1

A compound having the structure of formula (I), or a pharmaceutically acceptable salt or prodrug thereof, wherein, R is —O$^{11}$—(C$_1$ to C$_6$ alkyl), an O$^{11}$-glycol, —(C$_1$ to C$_6$ alkyl)-$^{18}$F, $^{18}$F, $^{123}$I, $^{125}$I, $^{124}$I, $^{131}$I, $^{32}$Cl, $^{33}$Cl, $^{34}$Cl, $^{74}$Br, $^{75}$Br, $^{76}$Br, $^{77}$Br, $^{78}$Br, $^{64}$Cu, $^{68}$Ga, $^{10}$B, $^{32}$P, $^{90}$Y, $^{103}$Pd, $^{131}$Cs, $^{153}$Sm, $^{177}$Lu, $^{211}$At, $^{212}$Bi, $^{212}$Po, $^{212}$Pb, $^{223}$Ra, or $^{225}$Ac:

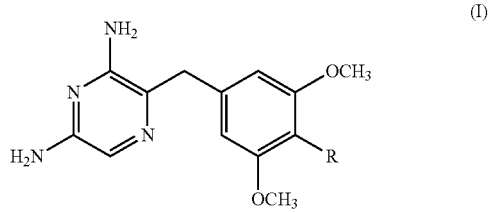

wherein, R is —O—C$^{11}$—(C$_1$ to C$_6$ alkyl), an O—C$^{11}$-glycol, —O—(C$_1$ to C$_6$ alkyl)-$^{18}$F, —OCH$_2$—($^{18}$F substituted phenyl), —OCH$_2$CH$_2$—($^{18}$F-substituted triazole), —OCH$_2$CH$_2$—($^{18}$F-substituted tetrazole), $^{18}$F-substituted boron-dipyrromethene, —O(CH$_2$CH$_2$O)$_n$CH$_2$CH$_2$—$^{18}$F, —OCH$_2$CH$_2$CH$_2$NHC(O)(CH$_2$CH$_2$O)$_n$—CH$_2$CH$_2$—$^{18}$F, -L$^1$-$^{68}$Ga, -L$^1$-$^{64}$Cu, -L$^1$-$^{99m}$Tc, radioactive halogen, $^{211}$At, -L$^1$-$^{10}$B, -L$^1$-$^{32}$P, -L$^1$-$^{90}$Y, -L$^1$-$^{103}$Pd, -L$^1$-$^{131}$Cs, -L$^1$-$^{153}$Sm, -L$^1$-$^{177}$Lu, -L$^1$-$^{211}$At, -L$^1$-$^{212}$Bi, -L$^1$-$^{212}$Po, -L$^1$-$^{212}$Pb, -L$^1$-$^{223}$Ra, or -L$^1$-$^{225}$Ac; n is 1-3; L$^1$ is a linker; or a pharmaceutically acceptable salt or prodrug thereof.

Embodiment 2

The compound of Embodiment 1, wherein said radioactive halogen is $^{18}$F, $^{123}$I, $^{125}$I, $^{124}$I, $^{131}$I, $^{32}$Cl, $^{33}$Cl, $^{34}$Cl, $^{74}$Br, $^{75}$Br, $^{76}$Br, $^{77}$Br, or 78Br.

Embodiment 3

The compound of Embodiment 1, wherein R is O$^{11}$CH$_3$.

Embodiment 4

The compound of Embodiment 1, wherein R is $^{18}$F.

Embodiment 5

The compound of Embodiment 1, which has the following structure:

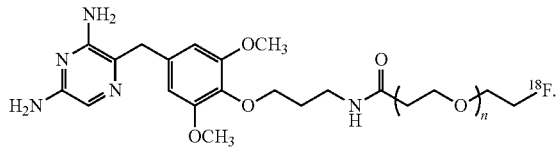

Embodiment 6

The compound of Embodiment 1, which has the following structure:

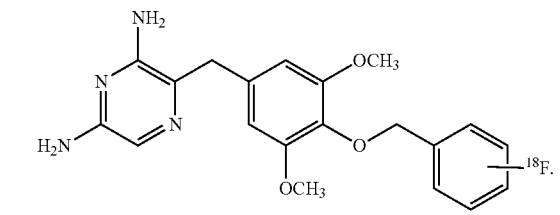

Embodiment 7
The compound of Embodiment 1, which has the following structure:
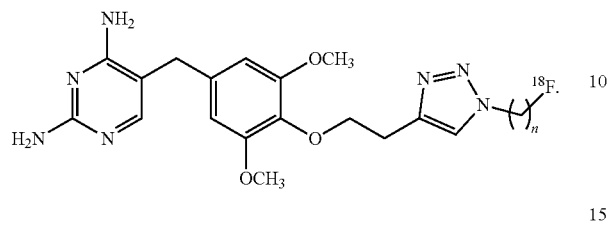
Embodiment 8
The compound of Embodiment 1, which has the following structure:
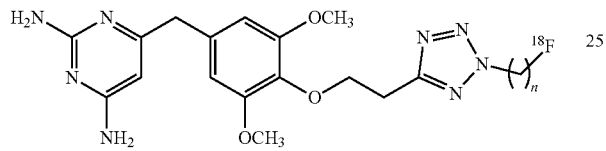
Embodiment 9
The compound of Embodiment 1 which has the following structure:
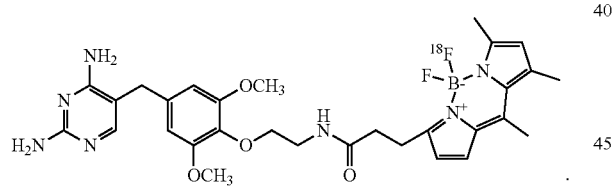
Embodiment 10
The compound of Embodiment 1, which has the following structure:
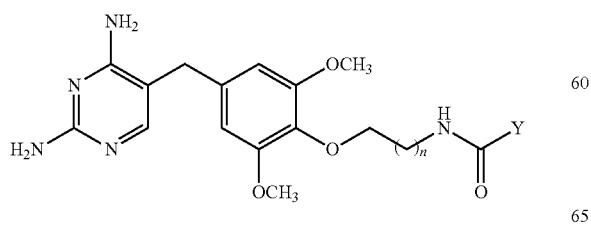
wherein: n is 1 to 6; and
Y is
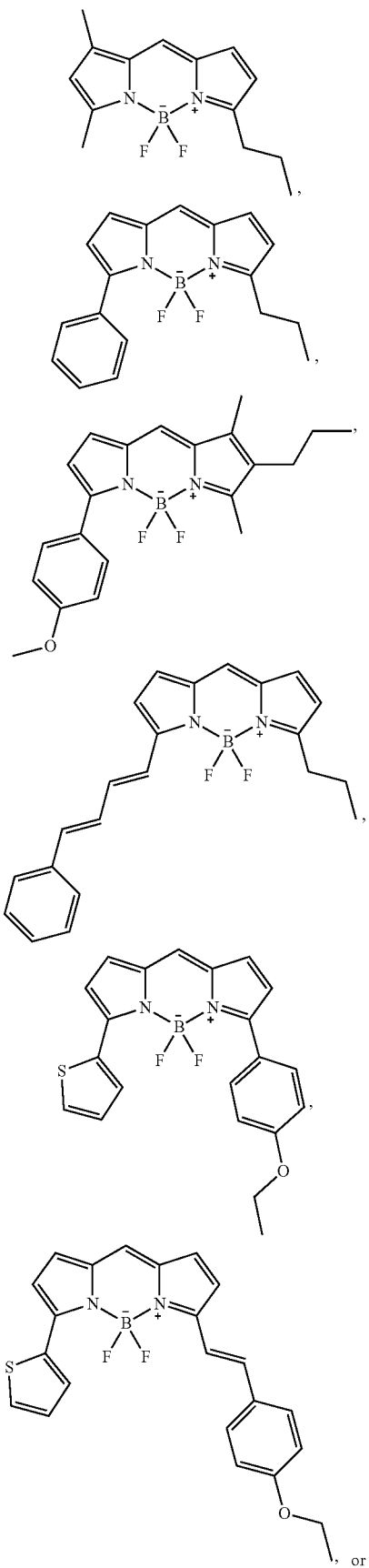
, or -continued

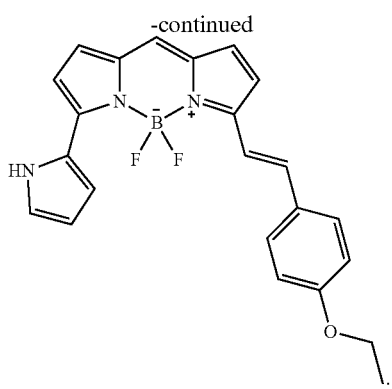

Embodiment 11

The compound of Embodiment 1, wherein $^{64}$Cu, $^{68}$Ga, $^{10}$B, $^{32}$P, $^{90}$Y, $^{103}$Pd, $^{131}$Cs, $^{153}$Sm, $^{177}$Lu, $^{211}$At, $^{212}$Bi, $^{212}$Po, $^{212}$Pb, $^{223}$Ra, or $^{225}$Ac is chelated.

Embodiment 12

The compound of Embodiment 11, wherein the chelation is performed using:

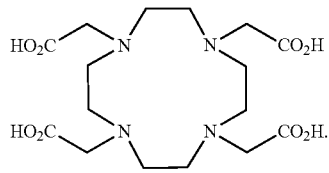 [SMILES: O=C(O)CN1CCN(CC(=O)O)CCN(CC(=O)O)CCN(CC(=O)O)CC1]

Embodiment 13

The compound of Embodiment 11, wherein the chelation is performed using:

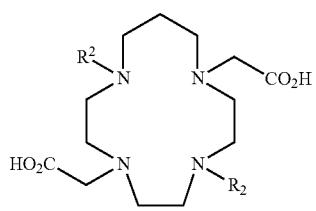

wherein, $R^2$ is, independently, H or $CH_2CO_2H$.

Embodiment 14

The compound of Embodiment 11, wherein the chelation is performed using:

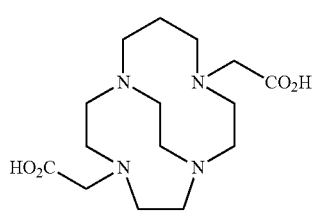 [SMILES: O=C(O)CN1CCCN2CCN(CC1)CCN(CC(=O)O)CC2]

Embodiment 15

The compound of Embodiment 11, wherein the chelation is performed using:

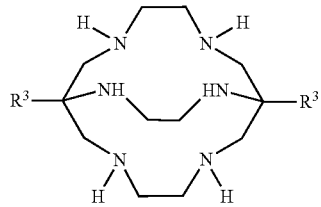

wherein, $R^3$ is, independently, H or $NH_2$.

Embodiment 16

The compound of Embodiment 11, wherein the chelation is performed using:

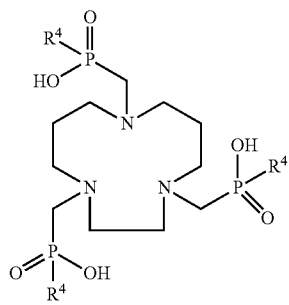

wherein, $R^4$ is, independently, H, —$(CH_2)_2CO_2H$, $CH_2OH$, or phenyl.

Embodiment 17

The compound of Embodiment 11, wherein the chelation is performed using:

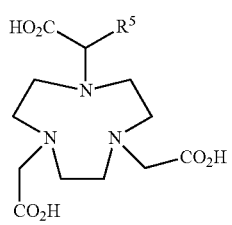

wherein, $R^5$ is H or —$(CH_2)_2CO_2H$.

Embodiment 18

The compound of Embodiment 11, wherein the chelation is performed using:

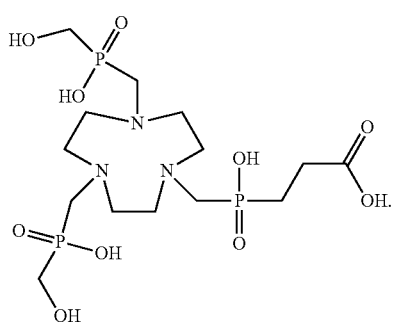 [SMILES: O=C(O)CCP(=O)(O)CN1CCN(CP(=O)(O)CO)CCN(CP(=O)(O)CO)CC1]

Embodiment 19

The compound of Embodiment 11, wherein the chelation is performed using:

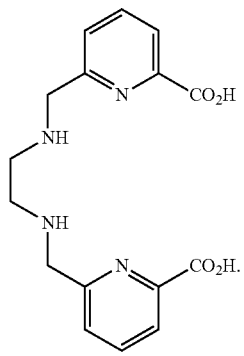 [SMILES: O=C(O)c1cccc(CNCCNCc2cccc(C(=O)O)n2)n1]

Embodiment 20

The compound of Embodiment 1, wherein R is:

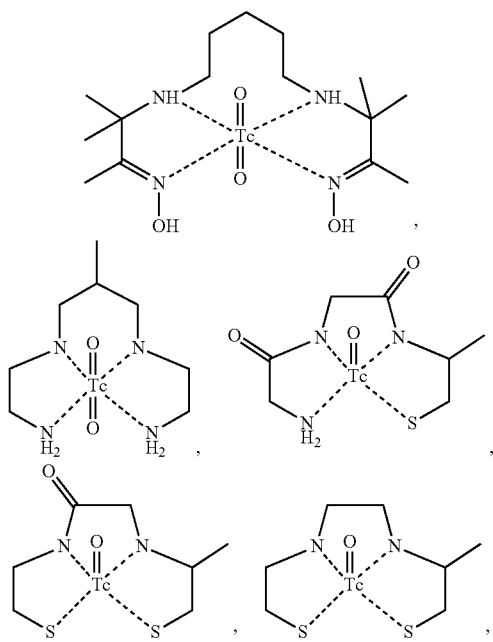

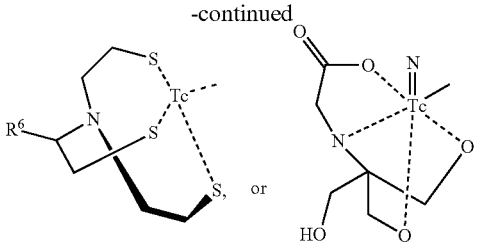

wherein, $R^6$ is alkyl or alkoxy.

Embodiment 21

A composition comprising a compound of any one of Embodiments 1 to 20 and a pharmaceutically acceptable carrier or diluent.

Embodiment 22

A method of imaging a bacterial infection in a subject, said method comprising (a) administering an effective amount of a compound of any one of Embodiments 1 to 20 to said subject; and (b) tracking said compound.

Embodiment 23

A method of tracking or monitoring bacteria in a subject, said method comprising (a) administering an effective amount of a compound of any one of Embodiments 1 to 20 to said subject; and (b) tracking said compound.

Embodiment 24

A method of distinguishing a bacterial infection from inflammation, said method comprising (a) administering an effective amount of a compound of any one of Embodiments 1 to 20 to said subject; and (b) tracking said compound using imaging; wherein said infection is displayed in the image and said inflammation is absent in said image.

Embodiment 25

The method of Embodiment 24, which distinguishes chemical or aspiration pneumonitis from bacterial pneumonia.

Embodiment 26

The method of Embodiment 23 or 24, wherein said bacteria are commensal or infectious.

Embodiment 27

A method of treating a bacterial infection in a subject, said method comprising (a) administering an antibiotic to said subject; (b) administering an effective amount of a compound of any one of Embodiments 1 to 20 to said subject; and (c) tracking said compound.

Embodiment 28

A method of monitoring cancer treatment in a subject, said method comprising (a) administering a chemotherapeutic, radiation, or immunotherapy to said subject; (b) administering an effective amount of a compound of any one of Embodiments 1 to 20 to said subject; and (c) tracking said compound.

Embodiment 29

A method of monitoring immunotherapy in a subject, said method comprising (a) genetically engineering cells from said patient to express dihydrofolate reductase; (b) tagging said engineered cells with a compound of any one of Embodiments 1 to 20; (c) administering said genetically engineered and tagged cells to said patient; and (d) tracking said genetically engineering cells and tagged cells by imaging.

Embodiment 30

The method of Embodiment 29, wherein said cells are T-cells, NK-cells, macrophages, B-cells, stem cells, hematopoietic stem cells, mesenchymal stem cells, neuro-progenitor cells, or induced pluripotent cells.

Embodiment 31

The method of any one of Embodiments 22 to 30, wherein said tracking is performed using positron emission tomography or single photon emission computed tomography.

Embodiment 32

The method of Embodiment 31, wherein the positron emission tomography which does not display areas of inflammation.

Embodiment 33

The method of any one of Embodiments 22 to 32, wherein said radiolabeled derivative of trimethoprim is administered through oral, intravenous, intra-arterial, intraperitoneal, intrathecal, or intracavitary injection

Embodiment 34

The method of any one of Embodiments 22 to 27, wherein said bacteria is *E. coli, S. aureus, P. aureginosa, Enterobacter, Haemophilus, Klebsiella, Morganella, Proteus, Providencia, Salmonella, Serratia, Streptococcus* A, *Streptococcus* B, *Streptococcus* C, *Streptococcus* G, *Mycobacterium* TB, or any combination thereof.

Embodiment 35

The method of any one of Embodiments 22 to 34, wherein said effective amount is about 1 to about 50 mCi.

Embodiment 36

The method of any one of Embodiments 22 to 27, wherein said bacteria comprises gastrointestinal tract bacteria.

Embodiment 37

The method of any one of Embodiments 22 to 36, wherein said subject is an animal or human.

Embodiment 38

A positron emission tomography reporter probe comprising a compound of any one of Embodiments 1 to 20.

Embodiment 39

A method of preparing the following compound:

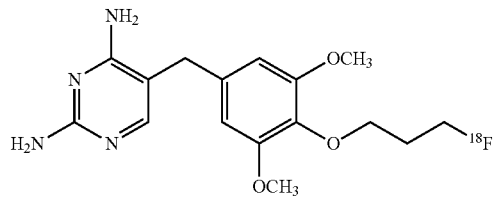 [SMILES: COc1cc(Cc2cnc(N)nc2N)cc(OC)c1OCCC[18F]]

said method comprising (i) reducing trimethoprim to provide

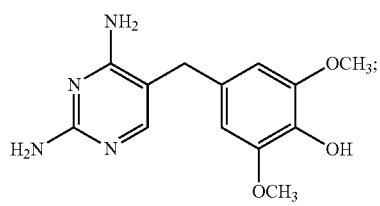 [SMILES: COc1cc(Cc2cnc(N)nc2N)cc(OC)c1O]

(ii) with 3-bromopropoxy-tert-butyldimethyl silate to provide

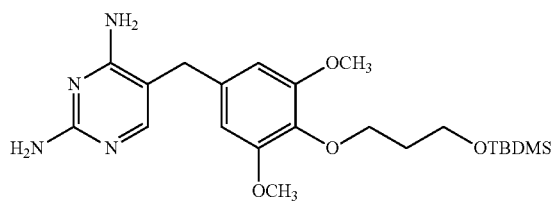 [SMILES: COc1cc(Cc2cnc(N)nc2N)cc(OC)c1OCCCO[Si](C)(C)C(C)(C)C]

iii) protecting with bis-Boc groups each NH$_2$ group

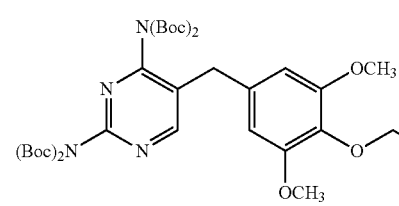

(iii) reacting the product of step (iii) deprotecting the product of step (iv) to provide

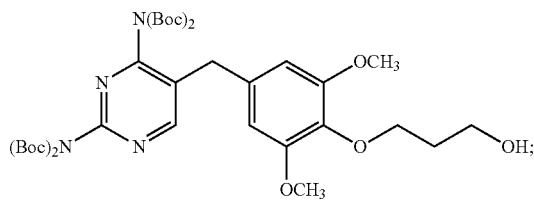

(v) mesylating the OH group of step (vi);

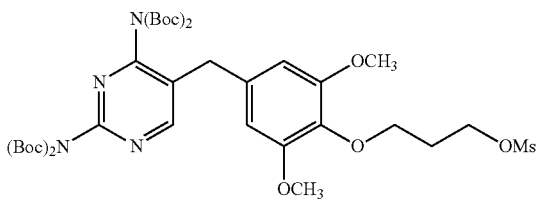

and (vii) replacing the mesylate group with $^{18}$F; and (viii) removing the BOC groups by deprotection.

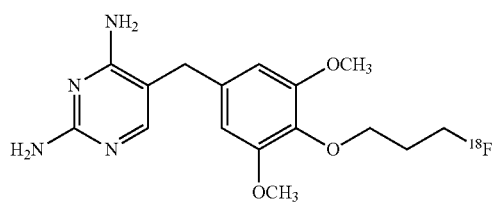 [SMILES: COc1cc(Cc2cnc(N)nc2N)cc(OC)c1OCCC[18F]]

VII. EXAMPLES

HEK293 and HCT116 cells (American Type Cell Culture) were cultured in complete media: DMEM with 10% fetal bovine serum (Invitrogen), 2 mM glutamine, 100 U/mL penicillin and 100 mg/mL streptomycin (all from Gibco). Cells were maintained in a humidified incubator at 37° C. Yellow fluorescent protein-DHFR cells ("DHFR" cells) were made by introducing a YFP-DHFR fusion gene cloned into pBMN YFP-DHFR (addgene, plasmid #29326) used to generate amphotrophic retrovirus (Clonetech, #631505). HEK293 and HCT116 cells were incubated with retrovirus and polybrene (6 μg/mL) for 4 hrs at 37° C., passaged and selected with YFP fluorescence activated cell sorting (BD).

YFP-DHFR cells plated in a 6-well plate (1×10$^5$ cells/well) were incubated overnight at 37° C. Live cell imaging was performed with fluorescence microscope using a GFP/YFP filter and phase contrast (Zeiss).

Example 1: Synthesis of [$^{11}$C]TMP

Scheme 1

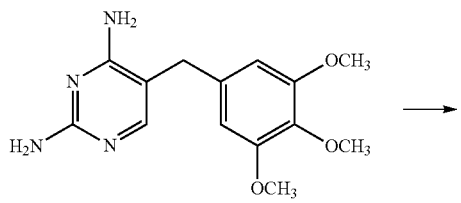

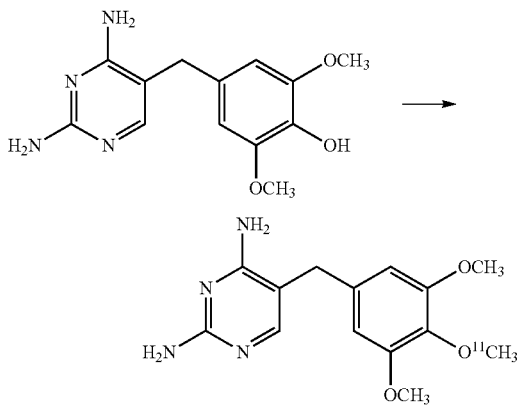

[$^{11}$C]TMP was prepared according to the procedure in ChemBioChem 2007, 8, 767-774. See, Scheme 1. Specifically, Trimethoprim (3 g, 10.03 mmol, purchased from Sigma-Aldrich) is selectively demethylated by HBr (37.4 mL, 48% in water) for 20 min at 95° C. After the reaction, the reaction mixture was cooled down and NaOH (8.92 mL, 50% w/w) added. After precipitation, the precipitate was filtered and collected, and re-dissolved in boiling water. NH$_4$OH was added to the mixture solution until pH 7, recrystallized at 4° C., filtered, and collected. 5-(3,5-Dimethoxy-4-hydroxy-benzyl)pyrimidine-2,4-diamine was obtained as a pink solid (1.51 g) in 52.9% yield; $^1$H NMR (DMSO-d$_6$) δ 8.06 (s, —OH), 7.45 (s, 1H), 6.48 (s, 2H), 5.99 (s, —NH$_2$), 5.63 (s, —NH$_2$), 3.71 (s, 6H), 3.47 (s, 2H).

5-(3,5-Dimethoxy-4-hydroxy-benzyl)pyrimidine-2,4-diamine was reacted with $^{11}$CH$_3$I for 5 min at 70° C. in the present of 5 N NaOH (4 μL) as a base. After the reaction, the reaction mixture was purified by HPLC with 12% EtOH in 0.01 M Phosphate buffer (pH=3). The flow rate of HPLC was 3 mL/min and the product ([$^{11}$C]TMP) was eluted at 12 min retention time. The radiochemical yield was 40-50% from [$^{11}$C]CH$_3$I, radiochemical purity was over 99%, and the specific activity was 37-56 GBq/μmol.

Example 2: Synthesis of Cold Fluoropropyl-TMP (FP-TMP)

Scheme 2

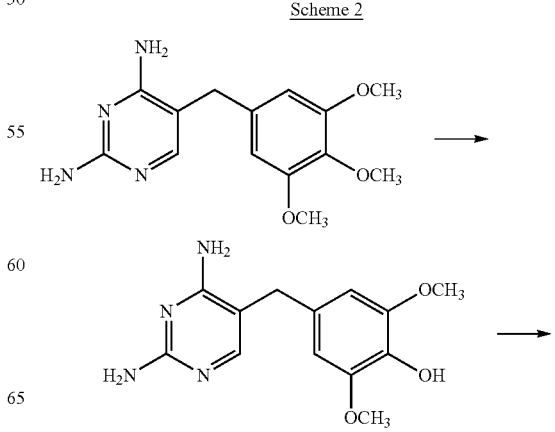

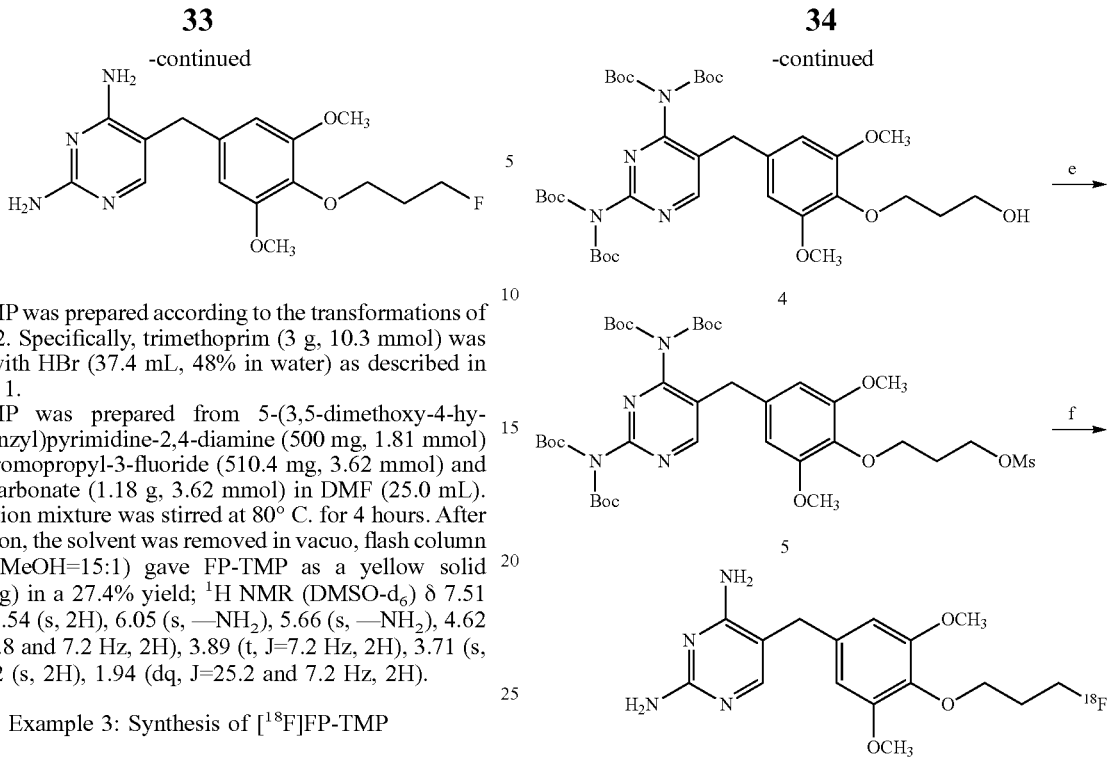

FP-TMP was prepared according to the transformations of Scheme 2. Specifically, trimethoprim (3 g, 10.3 mmol) was reacted with HBr (37.4 mL, 48% in water) as described in Example 1.

FP-TMP was prepared from 5-(3,5-dimethoxy-4-hydroxy-benzyl)pyrimidine-2,4-diamine (500 mg, 1.81 mmol) with 1-bromopropyl-3-fluoride (510.4 mg, 3.62 mmol) and cesium carbonate (1.18 g, 3.62 mmol) in DMF (25.0 mL). The reaction mixture was stirred at 80° C. for 4 hours. After the reaction, the solvent was removed in vacuo, flash column (CH$_2$Cl$_2$:MeOH=15:1) gave FP-TMP as a yellow solid (166.9 mg) in a 27.4% yield; $^1$H NMR (DMSO-d$_6$) δ 7.51 (s, 1H), 6.54 (s, 2H), 6.05 (s, —NH$_2$), 5.66 (s, —NH$_2$), 4.62 (dt, J=46.8 and 7.2 Hz, 2H), 3.89 (t, J=7.2 Hz, 2H), 3.71 (s, 6H), 3.52 (s, 2H), 1.94 (dq, J=25.2 and 7.2 Hz, 2H).

Example 3: Synthesis of [$^{18}$F]FP-TMP

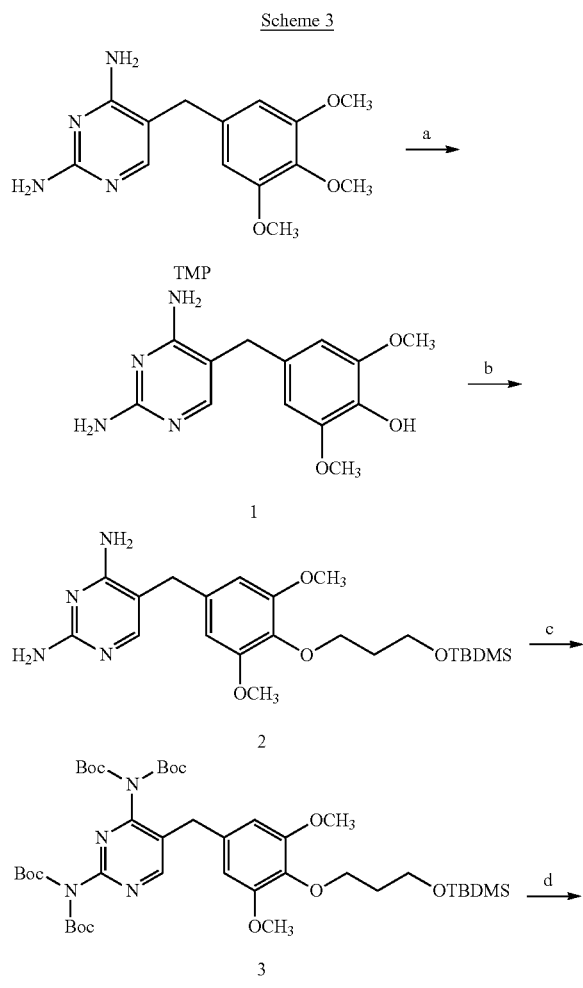

Reagents and conditions: a) 48% HBr, 95° C., 20 min; b) 3-bromopropoxy-tert-butyldimethyl silate, Cs$_2$CO$_3$, DMF, 80° C., 7 h; c) Boc$_2$O, Et$_3$N, DMAP, THF, rt, 20 h; d) 1M TBAF in THF, rt, 3 h; e) TsCl, Et$_3$N, CH$_2$Cl$_2$, 3 h; f) (i) K$^{18}$F, CH$_3$CN, 100° C., 10 min; (ii) 1N HCl, 100° C., 10 min

[$^{18}$F]Fluoroethyl-TMP was prepared according to the transformations of Scheme 3. Specifically, trimethoprim (3 g, 10.3 mmol) was reacted with HBr (37.4 mL, 48% in water) as described in Example 1.

The hydroxyl moiety of 4-((2,4-diaminopyrimidin-5-yl)methyl)-2,6-dimethoxyphenol (1, 43 mg, 0.15 mmol) was substituted using 3-bromopropoxy-tert-butyldimethyl silate (78.8 mg, 0.31 mmol), cesium carbonate (101.3 mg, 0.31 mmol) in DMF (2.14 mL) at 80° C. for 7 h. DMF was removed in vacuo, flash column gave 5-(4-(3-((tert-butyldimethylsilyl)oxy)propoxy)-3,5-dimethoxybenzyl)pyrimidine-2,4-diamine (2) as a light yellow solid (20 mg) in a 28.7% yield; $^1$H NMR (CDCl$_3$) δ 7.78 (s, 2H), 6.38 (s, 2H), 4.73 (—NH$_2$, 2H), 4.55 (—NH$_2$, 2H), 4.05 (t, J=7.2 Hz, 2H), 3.83-3.79 (m, 2H), 3.78 (s, 6H), 3.65 (s, 2H), 1.94 (t, J=7.2 Hz, 2H), 0.88 (s, 9H), 0.06 (s, 6H).

The amine groups of 5-(4-(3-((tert-butyldimethylsilyl)oxy)propoxy)-3,5-dimethoxybenzyl)pyrimidine-2,4-diamine (400 mg, 0.89 mmol) were then bis-BOC protected using Boc$_2$O (655.9 μL, 2.67 mmol), triethylamine (496.6 μL, 2.67 mmol), dimethylaminopyridine (75.6 mg, 0.26 mmol) in tetrahydrofuran (12 mL) at room temperature for 20 hours. The reaction mixture was diluted with water (50 mL), extracted with CH$_2$Cl$_2$ (50 mL) twice, washed with brine (50 mL), and then dried over with anhydrous sodium sulfate, concentrated. Flash column gave di-tert-butyl (5-(4-(3-((tert-butyldimethylsilyl)oxy)propoxy)-3,5-dimethoxybenzyl)pyrimidine-2,4-diyl)bis((tert-butoxycarbonyl)carbamate) (3) as a white solid (195.9 mg) in a 25.8% yield; $^1$H NMR (CDCl$_3$) δ 8.56 (s, 1H), 6.37 (s, 2H), 4.04 (t, J=7.2 Hz, 2H), 3.83-3.82 (m, 4H), 3.78 (s, 6H), 1.95 (q, J=7.2 Hz, 2H), 1.45 (s, 18H), 1.39 (s, 18H), 0.89 (s, 9H), 0.58 (s, 6H).

The silate moiety of di-tert-butyl (5-(4-(3-((tert-butyldimethylsilyl)oxy)propoxy)-3,5-dimethoxybenzyl)pyrimidine-2,4-diyl)bis((tert-butoxycarbonyl)carbamate) (3) (195.5 mg, 0.23 mmol) was then removed using 1 M tetrabutylammonium fluoride in tetrahydrofuran (0.69 mL, 0.69 mmol) and tetrahydrofuran (6.9 mL) at room temperature for 2 hours. The reaction mixture was diluted with water (50 mL), extracted with ethyl acetate (50 mL) twice, washed with brine (50 mL), and then dried over with anhydrous sodium sulfate, concentrated. Flash column (hexane:ethyl acetate=2:3) gave di-tert-butyl (5-(4-(3-hydroxypropoxy)-3,5-dimethoxybenzyl)pyrimidine-2,4-diyl)bis((tert-butoxycarbonyl)carbamate) (4) as a colorless oil (146.6 mg) in an 86.7% yield; $^1$H NMR (CDCl$_3$) δ 8.56 (s, 1H), 6.39 (s, 2H), 4.13 (t, J=7.2 Hz, 2H), 3.90 (t, J=7.2 Hz, 2H), 3.82 (s, 2H), 3.81 (s, 6H), 3.68 (t, J=3.6 Hz, 2H), 1.96 (q, J=7.2 Hz, 2H), 1.54 (s, 18H), 1.45 (s, 9H), 1.39 (s, 9H).

The propoxy moiety of di-tert-butyl (5-(4-(3-hydroxypropoxy)-3,5-dimethoxybenzyl)pyrimidine-2,4-diyl)bis((tert-butoxycarbonyl)carbamate) (4) (137.6 mg, 0.18 mmol) was mesylated using mesyl chloride (43.5 μL, 0.56 mmol), triethyl amine (78.3 μL, 0.56 mmol) in CH$_2$Cl$_2$ (4 mL) for 2 hours at room temperature. The reaction mixture was diluted with water (20 mL), extracted with CH$_2$Cl$_2$ (20 mL) twice, washed with brine (20 mL), and then dried over with anhydrous sodium sulfate, concentrated. Flash column (hexane:ethyl acetate=1:2) gave 3-(4-((2,4-bis(bis(tert-butoxycarbonyl)amino)pyrimidin-5-yl)methyl)-2,6-dimethoxyphenoxy)propyl methanesulfonate (5) as a white solid (133.5 mg) in an 87.8% yield; $^1$H NMR (CDCl$_3$) δ 8.55 (s, 1H), 6.38 (s, 2H), 4.54 (t, J=7.2 Hz, 2H), 4.05 (t, J=3.6 Hz, 2H), 3.81 (s, 2H), 3.79 (s, 6H), 3.03 (s, 3H), 1.45 (s, 18H), 1.39 (s, 18H).

Finally, the mesylate group of 3-(4-((2,4-bis(bis(tert-butoxycarbonyl)amino)pyrimidin-5-yl)methyl)-2,6-dimethoxyphenoxy)propyl methanesulfonate (5) (2 mg) was replaced with the $^{18}$F moiety using $^{18}$F-potassium fluoride and acetonitrile (200 μL) at 95° C. for 10 minutes. After the first reaction, 1 N HCl (1 mL) was added to a reaction mixture, and heated at 100° C. for 5 minutes. Followed by adding the HPLC eluent (1 mL), purified by HPLC (0.1% TFA in water:0.1% TFA in CH$_3$CN=80:20, flow rate=5 mL/min). The product ([$^{18}$F]FP-TMP) was eluted from 23 to 25 min.

Example 4: Synthesis of Halogen Radiolabeled Compounds

Compounds where R is a radioactive halogen may be prepared by replacing the "X" moiety in the following precursor compound which the appropriate halogen using reagents and skill in the art.

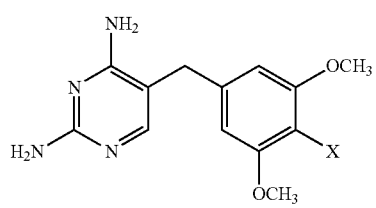

X = SnBu$_3$, SiMe$_3$, BF$_3$K

Similarly, the $^{211}$-At compounds may be prepared using the above-noted precursor compound where X is SnBu$_3$.

Example 5: Synthesis of Glycol Compounds

Compounds where R is a glycol may be prepared by replacing the "X" moiety in the following precursor compounds which the appropriate glycol moiety using reagents and skill in the art.

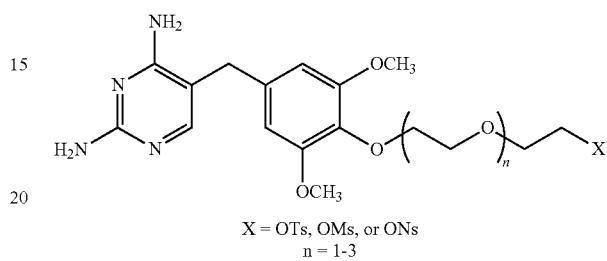

X = OTs, OMs, or ONs
n = 1-3

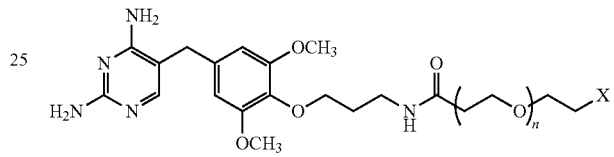

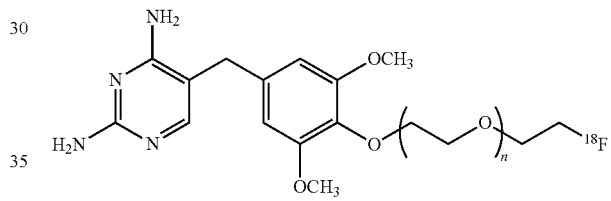

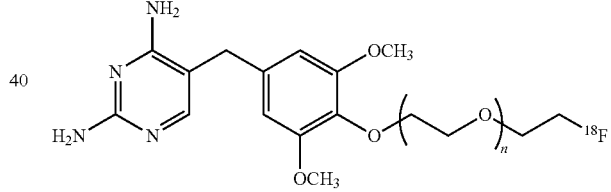

Example 6: Synthesis of $^{18}$F-Phenyl Compounds

Compounds where R is a $^{18}$F-phenyl group may be prepared by replacing the "X" moiety in the following precursor compound with the appropriate phenyl moiety using reagents and skill in the art.

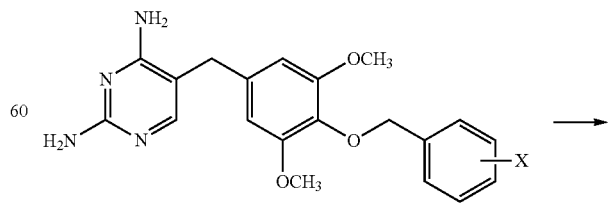

X = trimethylamine triflate salt or iodonium salt

-continued

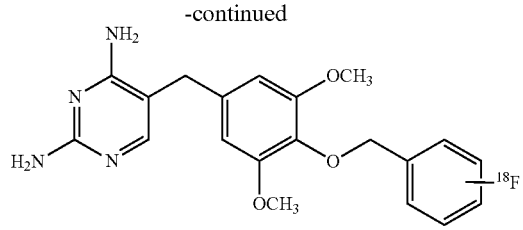

Example 7: Synthesis of $^{18}$F-Triazole or Tetrazole Compounds

Compounds where R is a $^{18}$F-phenyl group may be prepared by replacing the "X" moiety in the following precursor compound with the appropriate triazole or tetrazole moiety using reagents and skill in the art.

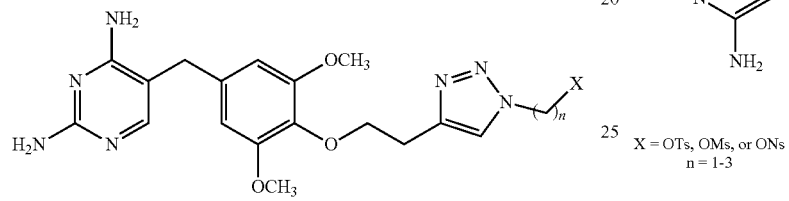

↓

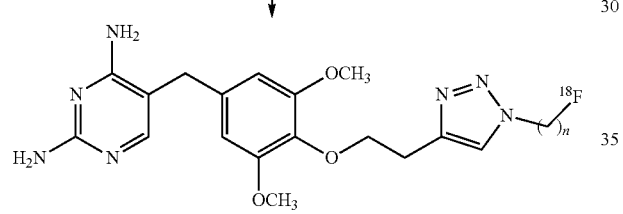

-continued

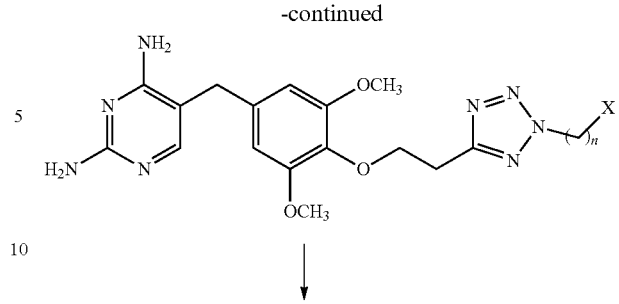

↓

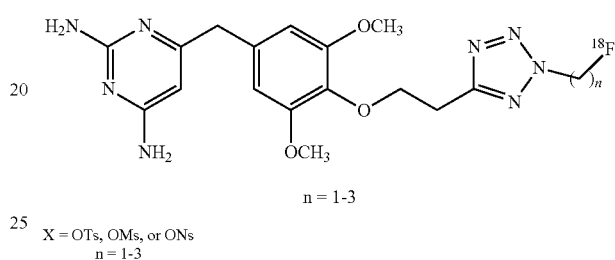

n = 1-3
X = OTs, OMs, or ONs
n = 1-3

Example 8: Synthesis of a $^{18}$F-BODIPY Compound

The following $^{18}$F-BODIPY compounds may be prepared by replacing the OTf moiety in the following precursor compound with E using reagents and skill in the art

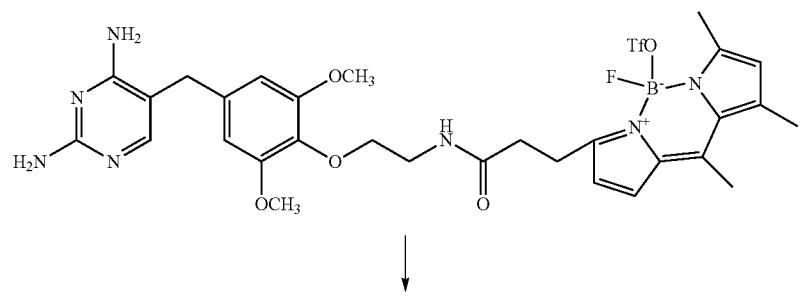

↓

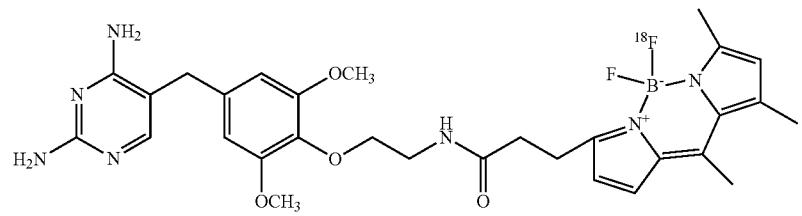

Accordingly, the following compounds having BODIPY structurally similar moieties may be prepared:

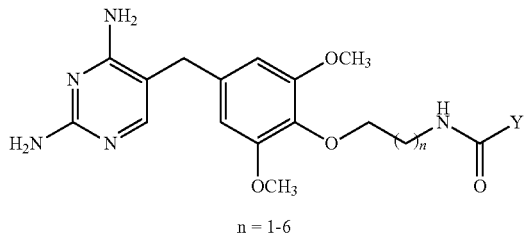

n = 1-6

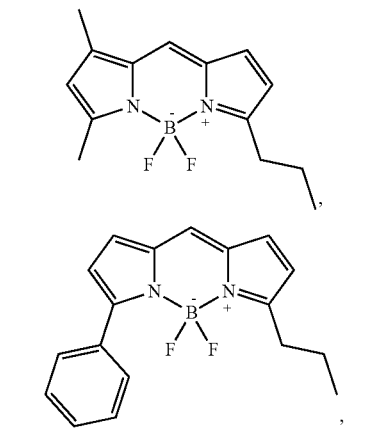

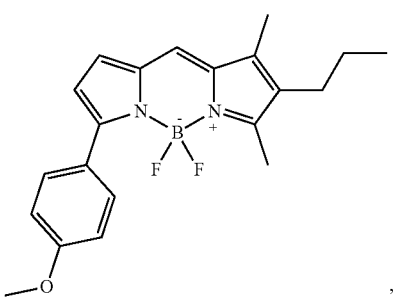

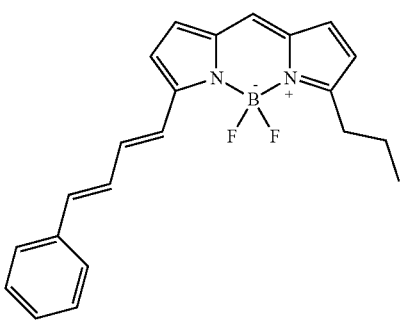

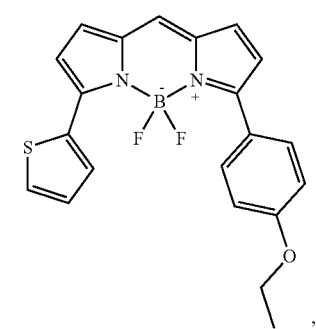

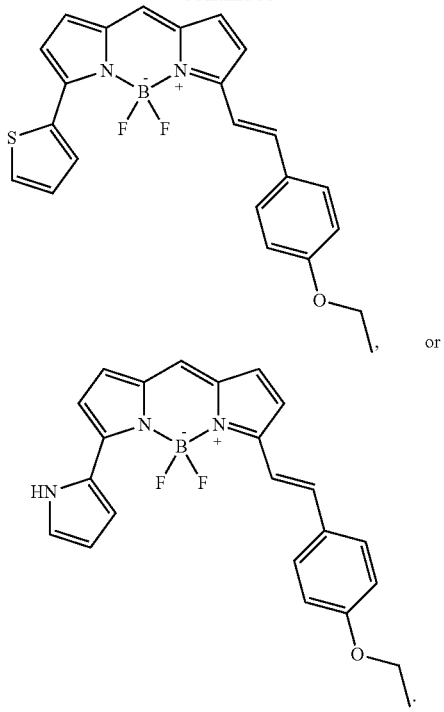

wherein Y is

Example 9: [¹¹C]TMP Binding

To assess [¹¹C]TMP binding to recombinant Ec DHFR protein (addgene, plasmid #29326) expressed in *E. coli* (Invitrogen) and purified as detailed in Iwamoto, *Chem. Biol.*, 17:981-988, and a dot blot assay was performed. Two µL of Ec DHFR protein (as above) at varying concentrations of 100-4 µM were dotted onto a nitrocellulose membrane (Abcam) dried for 1 h, blocked, and then incubated in 5% milk in TBS-T (20 mM Tris HCl, 150 mM NaCl, pH 7.5, 0.05% Tween 20), and incubated with [¹¹C]TMP (2 million CPM) for 30 minutes with or without cold TMP (10 µM) for 30 minutes. The blot was then washed with TBS×2 and exposed to a phosphor plate (GE) and imaged on a Typhoon laser scanner (GE).

Figure 2:
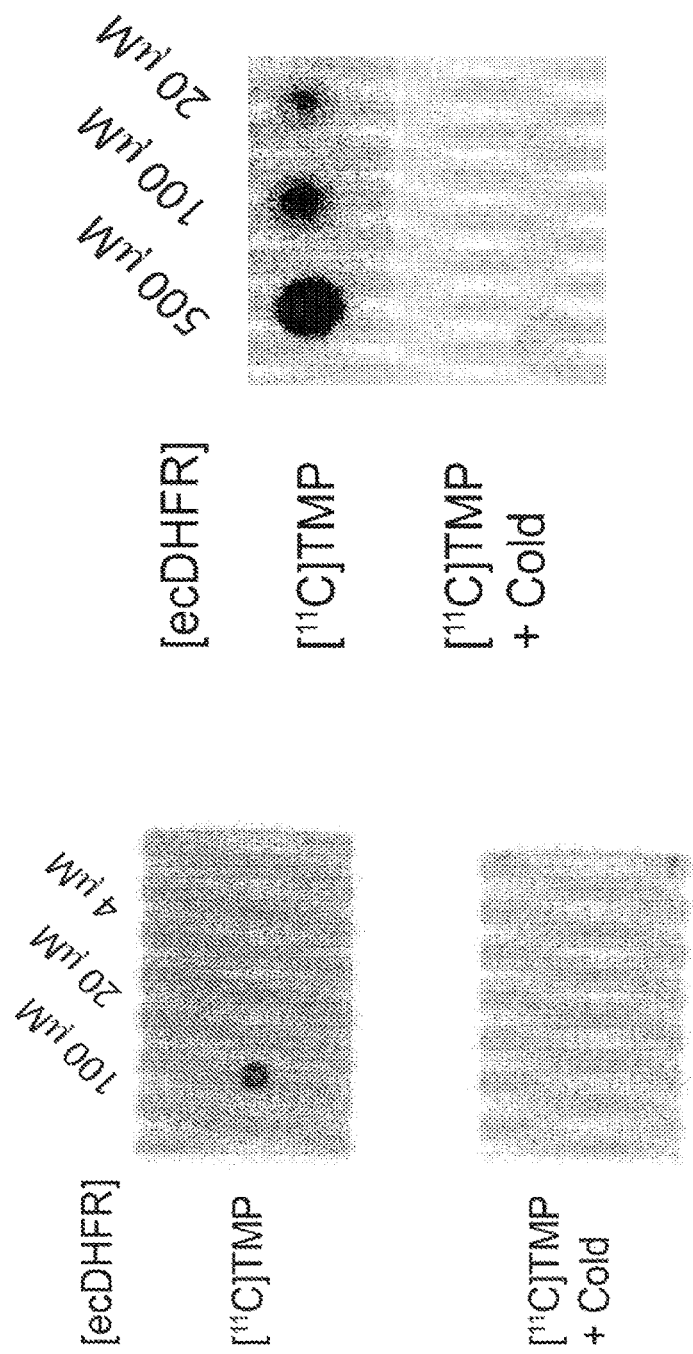
FIG. 2 is a dose-response and competition dot blot showing various concentrations of recombinant Ec DHFR spotted on to a nitrocellulose membrane.

The dot blot of FIG. 2 shows [¹¹C]TMP concentration-dependent specific cell uptake using an in vitro dot blot assay with recombinant protein. Separately, robust uptake in cells carrying YFP-Ec DHFR fusions was seen.

Example 10: Transgenic Cell Lines

Figure 3:
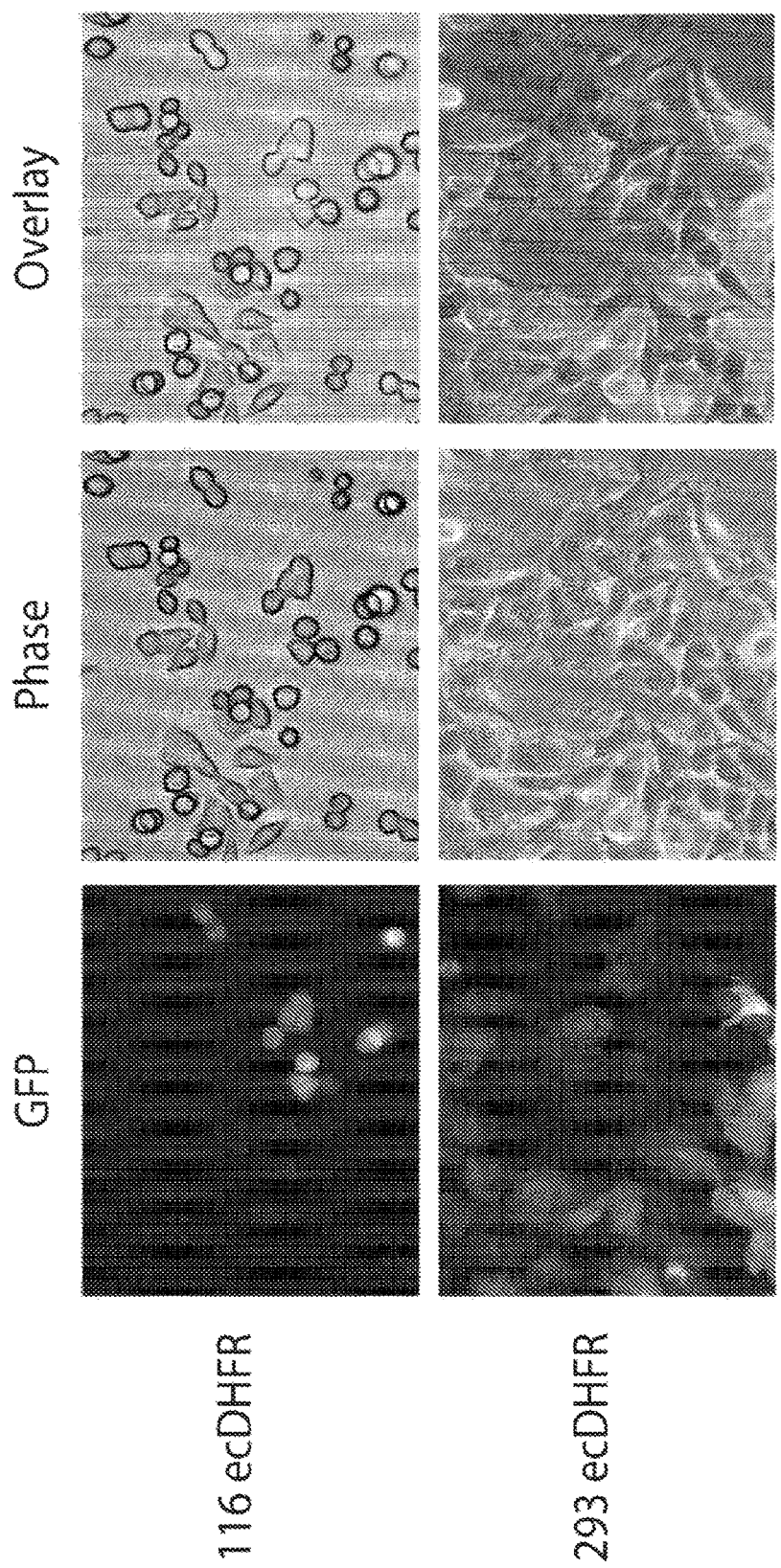
FIG. 3 are fluorescent microscopy images of HEK293 and HCT 116 cells and virally transduced YFP-DHFR cells assessed for yellow fluorescent protein transgene expression.

Transgenic mammalian cell lines carrying Ec DHFR were made using the Phoenix Amphotropic retroviral transduction. Specifically, these cell lines were prepared by retroviral transduction by transfecting Phoenix Amphotrophic cell lines (ATCC, # CRL-3213) with plasmid vector pBMN YFP-Ec-DHFR ires HcRed and used for YFP-Ec-DHFR expression using FACS (BD). Bright field and fluorescent microscopy was utilized to analyze the same and confirmed presence of the transgene in human embryonic kidney, HEK 293 cells (ATCC, # CCL-1573) and human colon carcinoma HCT 116 cells (ATCC, # CCL-247). See, FIG. 3.

The cells were lysed in radioimmunoprecipitation assay buffer (50 mM Tris, 150 mM sodium chloride, 1.0 mM EDTA, 1% Nonidet P40, and 0.25% SDS (pH 7.0)), supplemented with complete protease inhibitor cocktail (Roche) and phosphatase inhibitor cocktail 1 (Sigma Chemical Co). The cells were sonicated briefly, centrifuged at 13,000×g for 20 min at 4° C., and the supernatant collected. The protein concentration was determined using a Bio-Rad Dc protein assay kit (Bio-Rad Laboratories). Lysates containing 30 µg of protein were run on a 4-20% acrylamide gel and transferred to a PVDF membrane using the Trans-Blot Turbo Transfer System (Bio-Rad Laboratories). The PVDF membrane was incubated with Odyssey blocking buffer (Licor Biotechnology) for 1 h at room temperature, then overnight with a mouse monoclonal antibody recognizing YFP (catalogue #632381, Clontech) at a 1:1000 dilution at 4° C., and finally with the secondary antibody, IRDye 680RD goat anti-mouse IgG (Licor Biotechnology) at a 1:15,000 dilution. The same blot was incubated overnight with goat anti-GAPDH antibody (Santa Cruz) at a 1:300 dilution at 4° C. and then with IRDye 680RD donkey anti-goat IgG secondary antibody (Licor Biotechnology) at a 1:15,000 dilution. The signals were detected and quantified using the Odyssey® CLx Infrared Imaging System (Licor Biotechnology).

Figure 10:
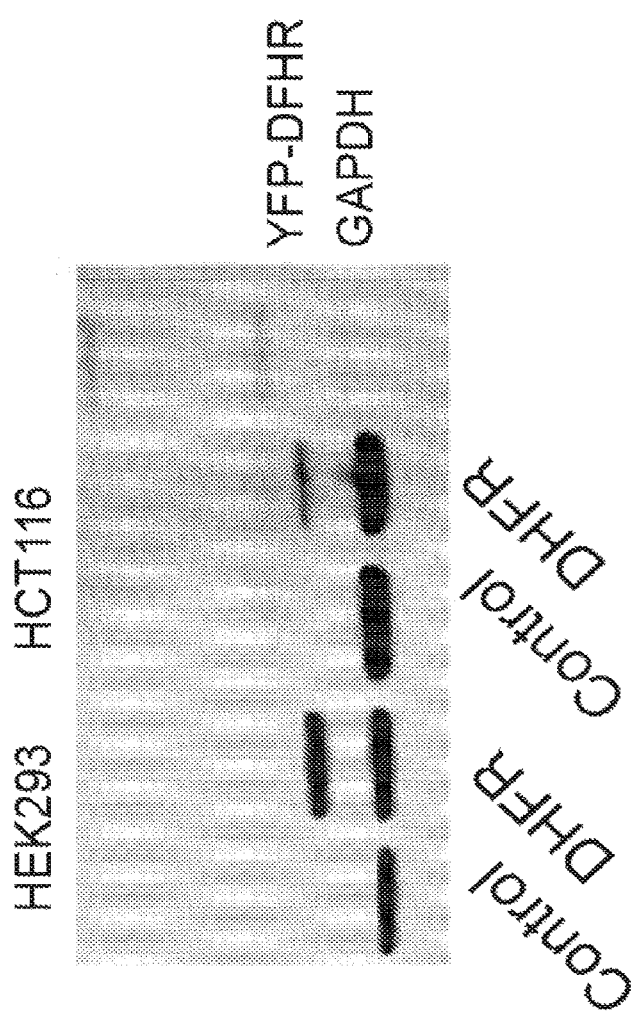
FIG. 10 the immunoblot probing for YFP of YFP-DHFR fusion proteins. The expected fusion protein molecular weight is 45 kDa. GADPH provided a loading control.

Western blotting confirmed the correct molecular weight (FIG. 10, 45 kDa).

Example 11: [$^{11}$C]TMP HEK 293 Cell Uptake Studies

Figure 5:
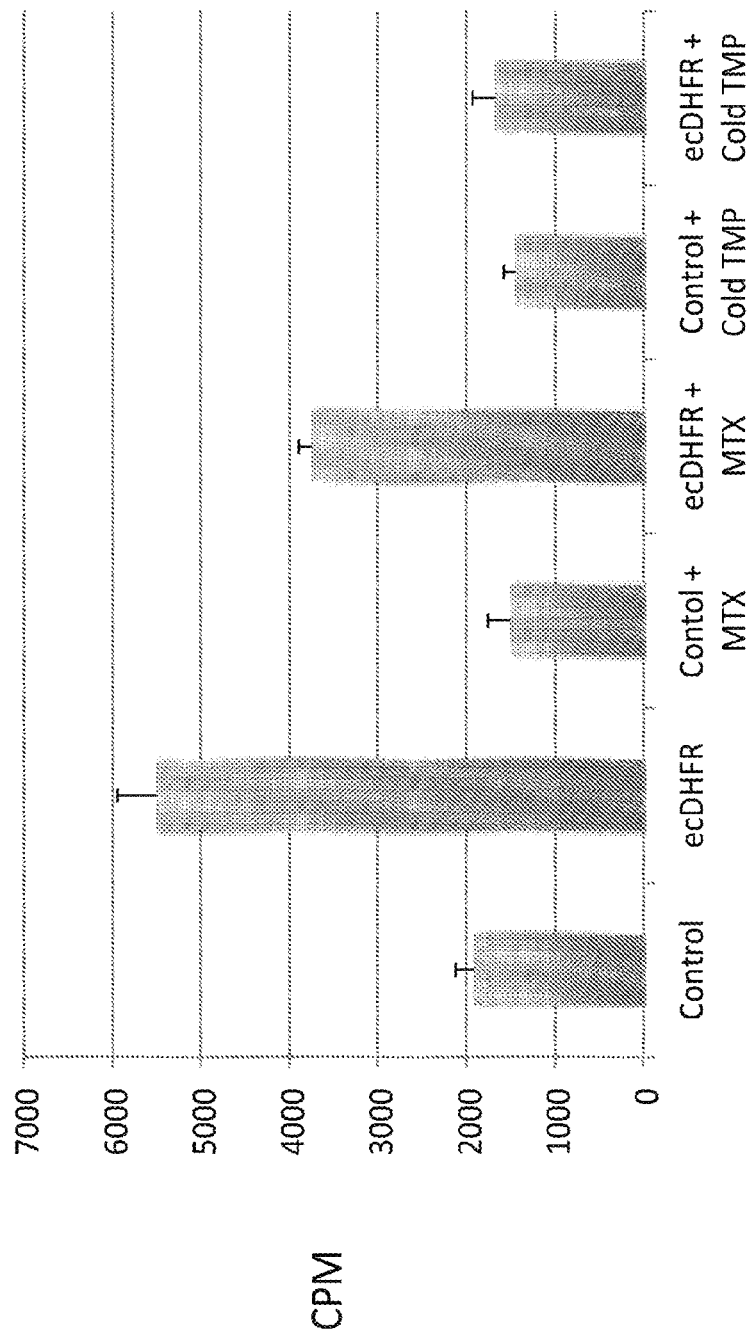
FIG. 5 is a bar graph of counts per minute (cpm) of HCT 116 control cells or DHFR cells incubated with [$^{11}$C]TMP with and without competing cold TMP (10 μM). Error bars represent standard deviation (n=3). Mammalian DHFR inhibitor methotrexate (10 μM) was added and showed little effect on specificity of TMP binding.

In this example, a HEK 293 cell uptake study was performed using TMP radiotracer cell uptake studies. Confluent HEK 293 control (ATCC, # CCL-1573; 8 million) or DHFR cells (high uptake) were trypsinized, incubated with [$^{11}$C]TMP with and without competing 10 µM cold TMP to block radiotracer uptake. Cells were washed twice with cold PBS and then counted with a gamma counter (FIG. 5).

These results show that there was over 10-fold signal induction at the time of assay with HEK293 cells and 3-fold induction with HCT116 cells, which correlated with differences in expression in the western blot.

Figure 4:
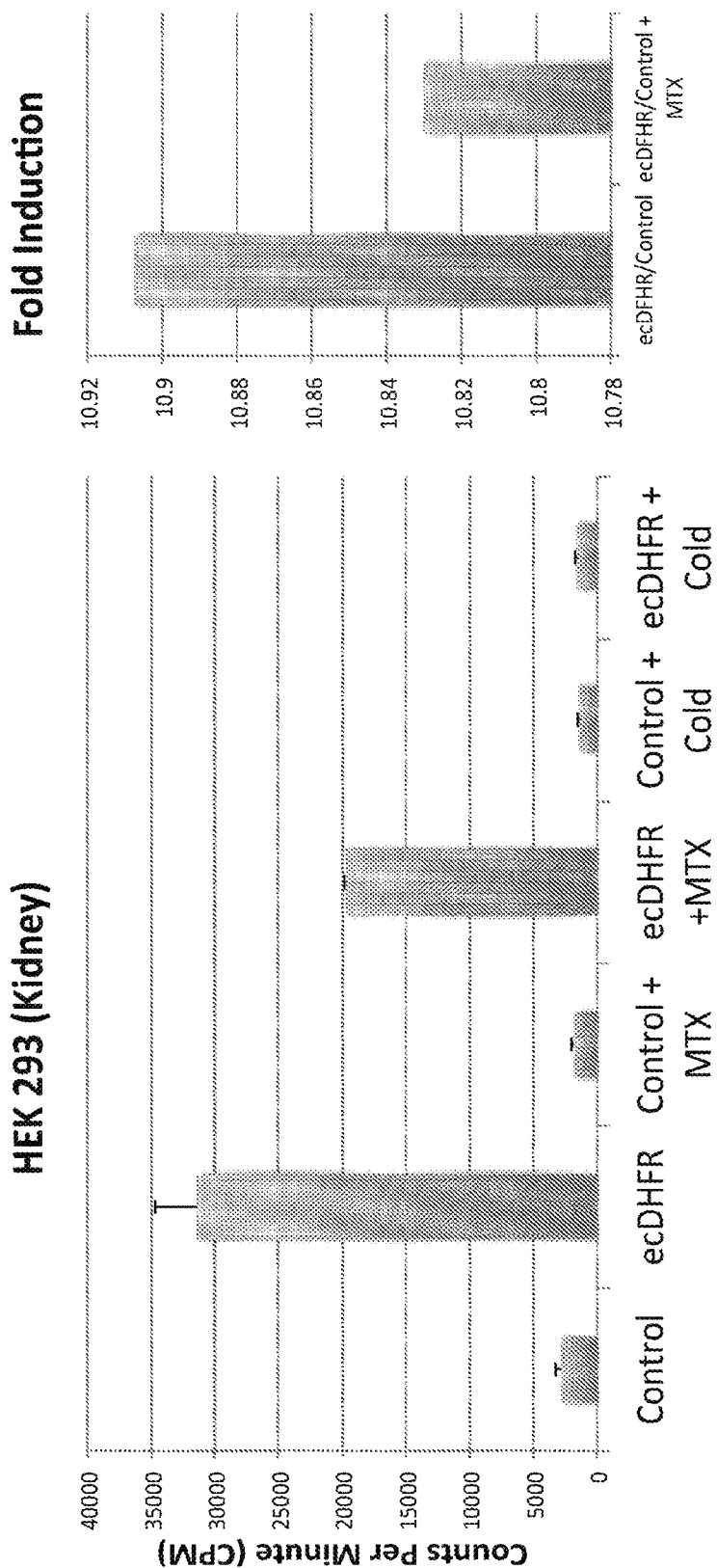
FIG. 4 is a bar graph of counts per minute (cpm) of HEK 293 control cells or DHFR cells incubated with [$^{11}$C]TMP with and without competing cold TMP (10 μM) or methotrexate (MTX) (10 μM). The competing compounds were added at 10 μM. Error bars represent standard deviation (n=3).

Given that 5 half-lives had occurred at the time of assay, less than 10% of the tracer bound to Ec DFHR remained detectable. This large percentage of decayed TMP competition suggests that TMP radiotracers labeled with longer-lived isotopes may demonstrate over 2 orders of magnitude of specific signal. Methotrexate co-treatment during uptake experiments did not change dynamic range of uptake and only marginally affected the absolute uptake numbers in HEK293 cells (FIG. 4).

Example 12: [$^{11}$C]TMP Bacterial Cell Uptake Studies

Figure 6:
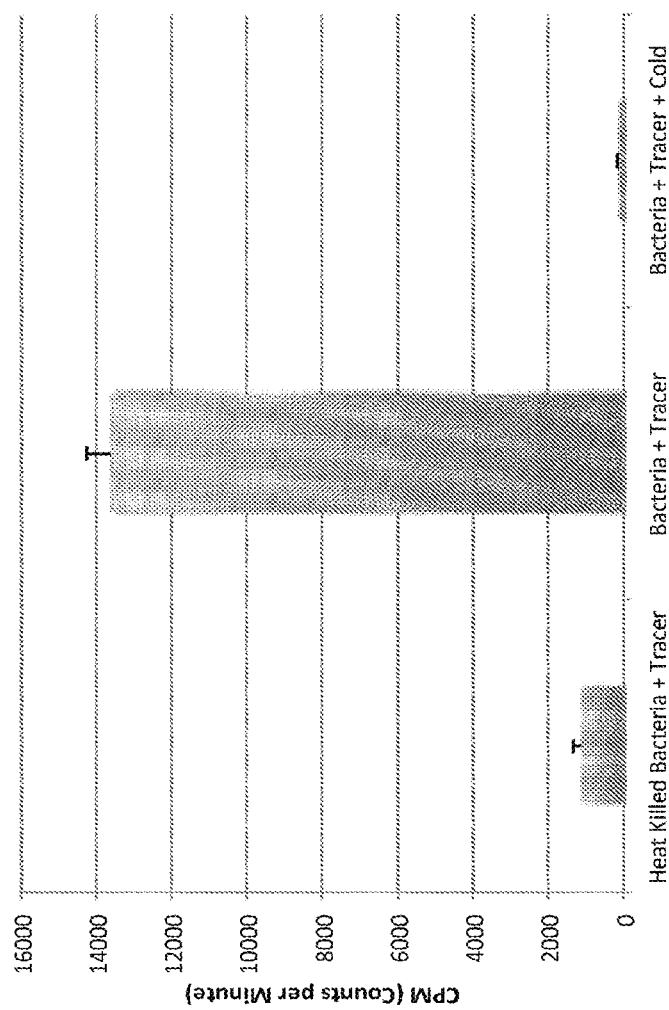
FIG. 6 is a bar graph of counts per minute (cpm) of bacteria (*E. coli*) incubated with [$^{11}$C]TMP after being assayed for uptake with a gamma counter. Error bars represent standard deviation (n=3).
Figure 7:
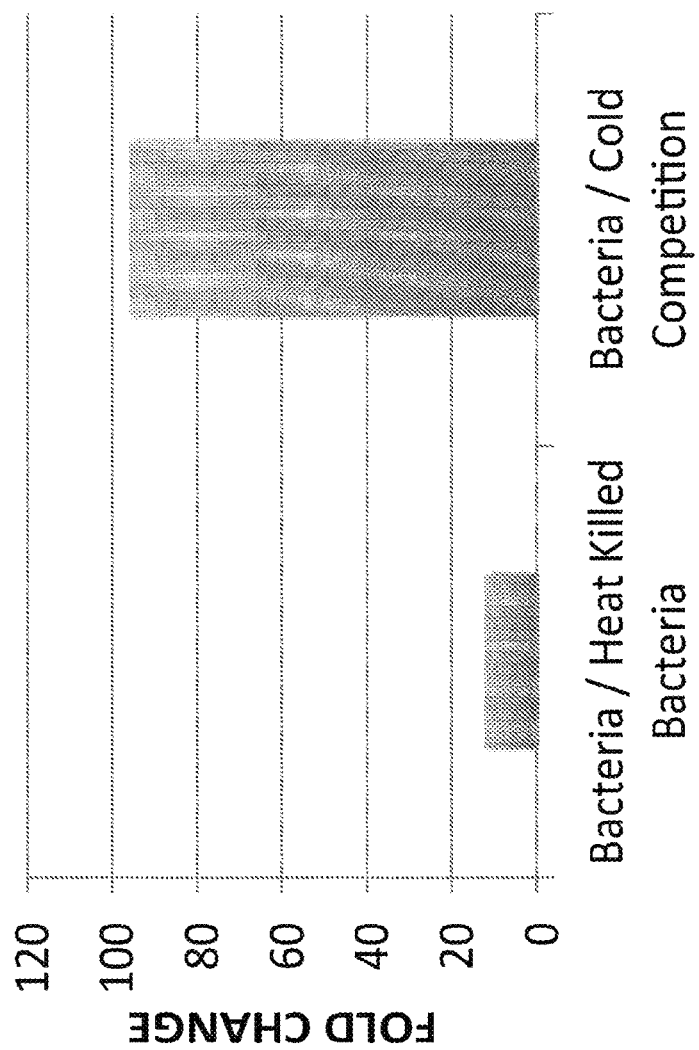
FIG. 7 is a bar graph illustrating the fold induction from of the data of FIG. 7. It is the signal in live bacterial group over heat killed or live bacterial with cold TMP competition.

This example was performed to illustrate that TMP radiotracer derivatives may be used to specifically image bacteria. To this end, radiotracer bacterial cell uptake studies were completed using E. coli (Invitrogen; HB101). E. coli were grown overnight to saturation in standard LB media and then diluted 1:5 in fresh media 1 hour before incubation with radiotracer to ensure log phase growth. The experimental groups incubated with [$^{11}$C]TMP were Heat-killed Bacteria (low uptake), Bacteria (high uptake), and Bacteria+ Cold (low uptake) indicating incubation with 10 µM of cold TMP to block radiotracer uptake (FIGS. 6 and 7).

These bacterial uptake studies show over 10-fold specific uptake of [$^{11}$C]TMP in live bacteria compared with heat killed bacteria and that the uptake can be completely blocked with cold compound.

Example 13: [$^{11}$C]TMP In Vivo Studies

Figure 11:
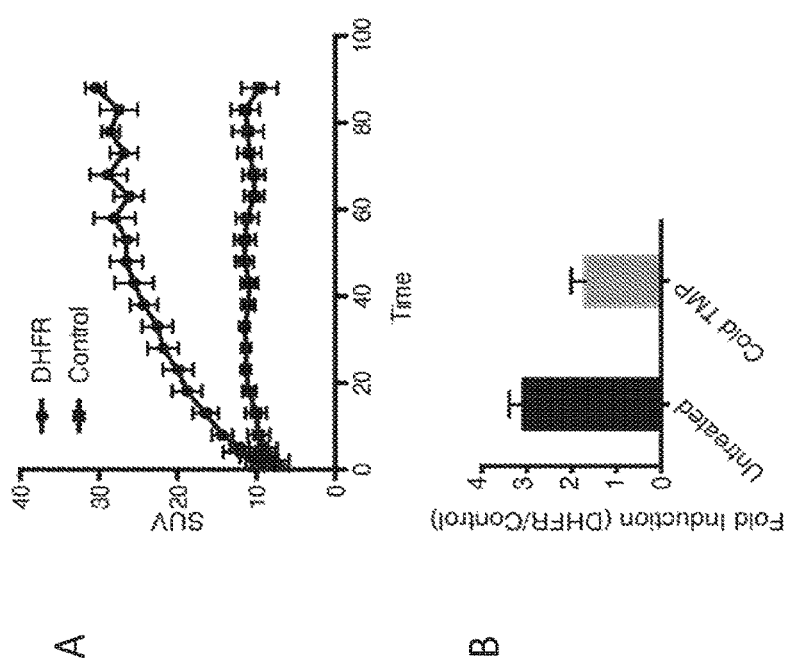
FIGS. 11A and 11B are line and bar graphs, respectively, showing the quantification of SUV (signal/dose/g) from small animal micro PET/CT scans of DHFR or control tumors with [$^{11}$C]TMP where HCT116 tumors were xenografted subcutaneously (10 million cells) to the shoulders of nude mice. The tumors were grown for 10 days and imaged using small animal PET followed by CT. Error bars represent standard deviation (n=3). B) Fold change of SUV (DHFR signal divided by control signal) with and without oral TMP block.

After successful in vitro uptake experiments, HCT116 tumor cells were xenografted into the posterior back/shoulder subcutaneous tissues of nude mice to assess in vivo tracer distribution and uptake. Tumors were grown over 10 days and animals were maintained on a low folate diet. Mice were anesthetized and imaged with small animal PET/CT. A representative image is shown at 90 minutes (5 min bin) after [$^{11}$C]TMP injection which shows strong signal coming from the DHFR carrying tumor cells. A time activity curve shows rapid and dynamic identification of DHFR carrying cells and over 3-fold signal induction with HCT116 cells compared to control cells, which correlated with in vitro uptake data (FIG. 11A). Other tissues with rapid uptake included the kidneys and bladder. There is decreased fold-induction (DHFR to control tumor signal) from the DHFR tumors after pre-treatment with cold oral TMP competition (0.2 mg/mL via the drinking water, FIG. 11B).

Figure 12:
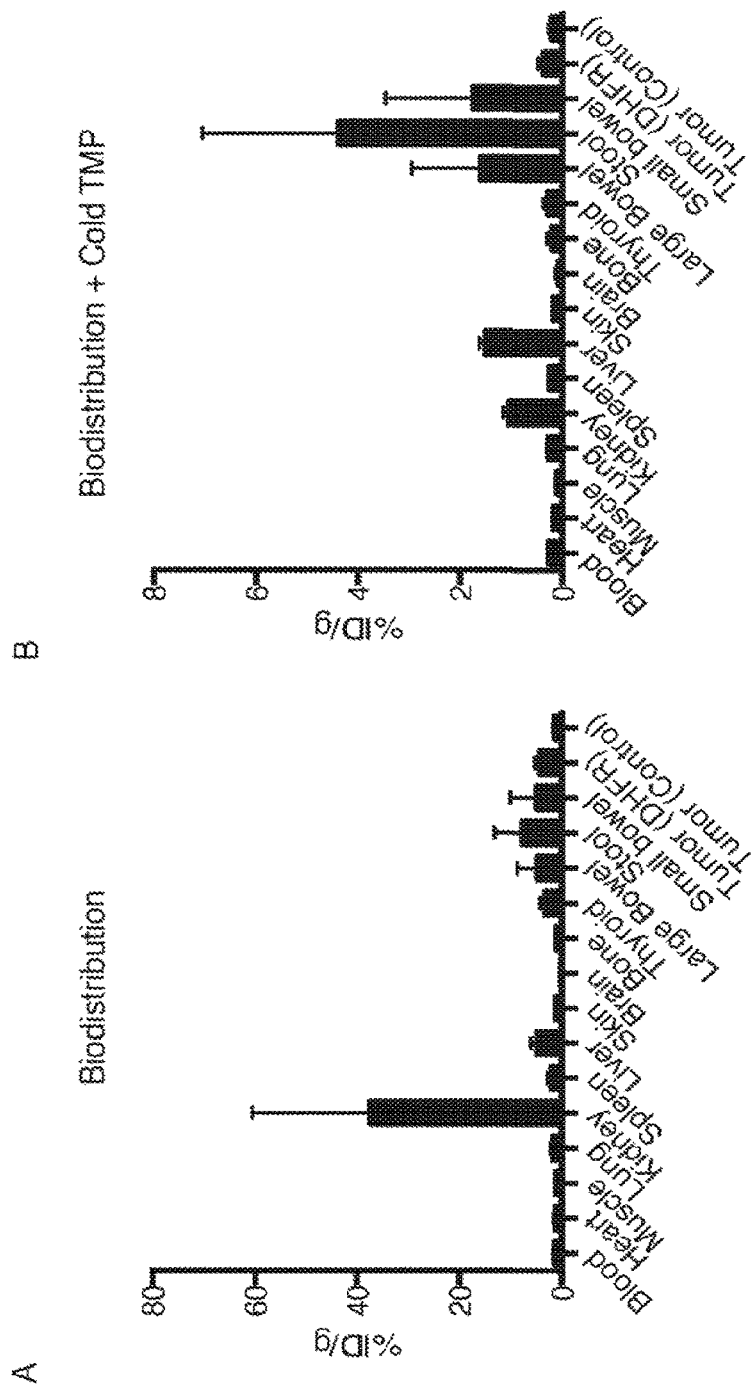
FIGS. 12A and 12B are bar graphs showing the in vivo biodistribution of [$^{11}$C]TMP in the absence and presence of an oral TMP block. The Biodistribution studies were completed 90 minutes after injection of [$^{11}$C]TMP. Dissected tissues were analyzed with a gamma counter. Error bars represent standard deviation (n=3).
Figure 14:
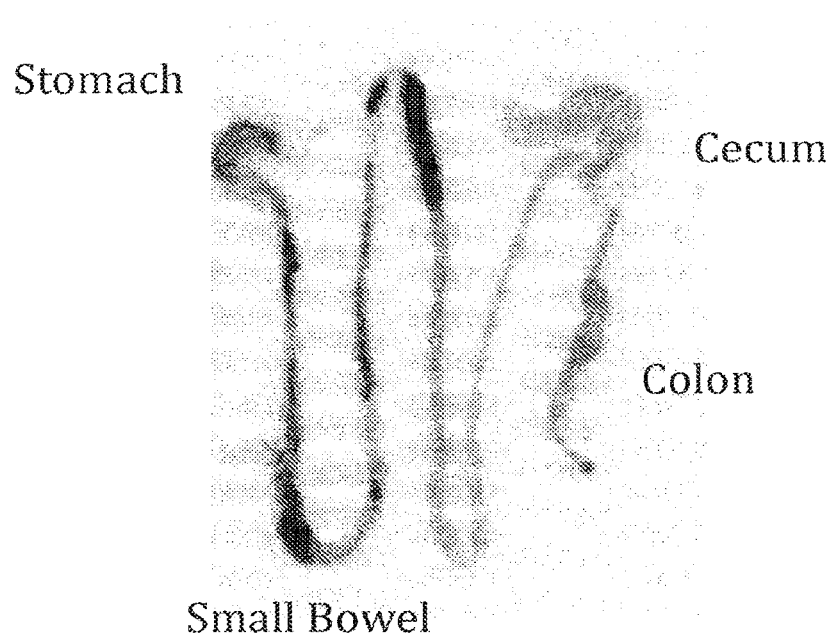
FIG. 14 is an autoradiograph of an explanted GI tract from the stomach to the rectum of a mouse.

Biodistribution analysis was performed at 90 minutes after injection. Here again, DHFR to control signal induction showed over 3-fold signal induction in DHFR tumors versus control (FIG. 12A). There was significant uptake from the kidneys, but also modest liver uptake. Nonuniform increased signal in the small bowel after GI tract explant supports hepatobiliary excretion of the radiotracer (FIG. 14).

Notably, the signal in the small bowel appeared more concentrated than in the cecum/colon, the site of highest commensal bacterial colonization.

Figure 15:
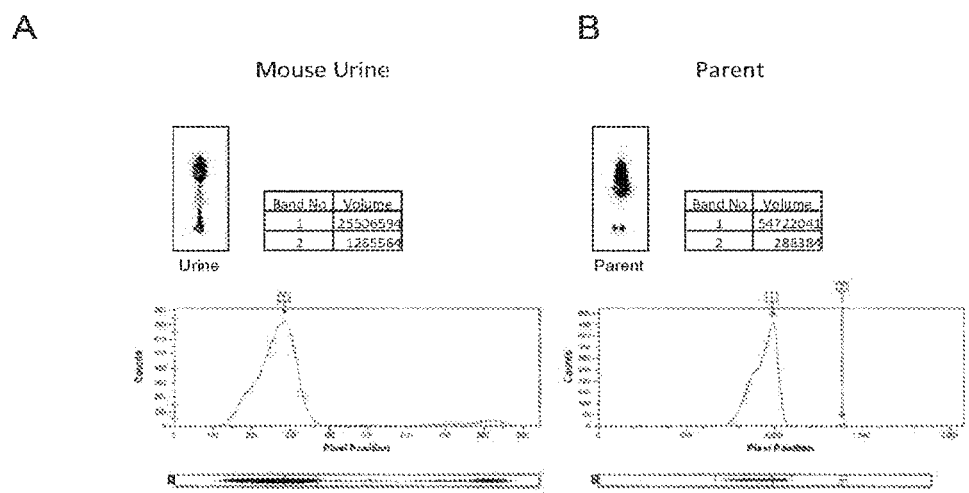
FIGS. 15A and 15B are thin layer films and radiochromatographs showing the spot size and relative counts from mouse urine compared to parent [$^{11}$C]TMP.
Figure 16:
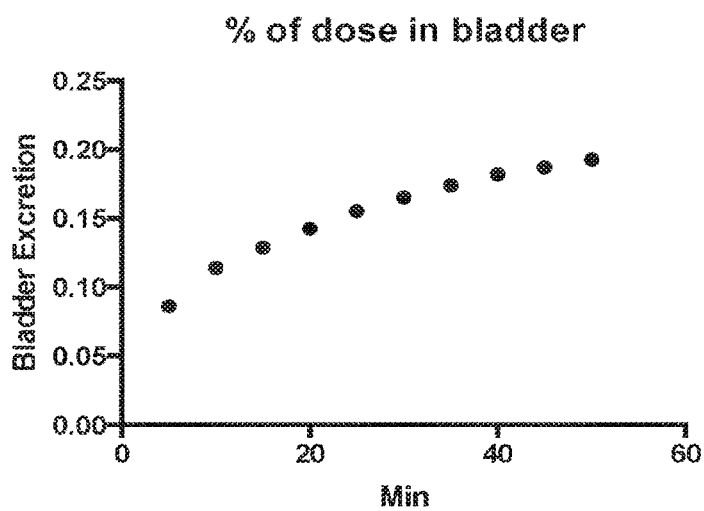
FIG. 16 is a graph illustrating the percent of radiosignal in the bladder while under anesthesia (no micturition) as assessed by measuring the signal in the bladder divided by the total counts in the animal over time (n=1).

[$^{11}$C]TMP is excreted in the urine predominantly as the parent compound as measured by radio-thin layer chromatography (FIGS. 15A and 15B) and there is rapid accumulation in the bladder (FIG. 16). The rate of urine filtration is rapid with approximately 20% of the dose rapidly accumulating in the bladder. Some of this prompt excretion may be related to the fact that mice have 8-10-fold circulating folate levels compared to humans. This excess of competing substrate may mildly affect DHFR active site occupancy, which could affect the overall signal to noise, thus mice are maintained on low folate, antibiotic free diets for 2 weeks prior to experimentation.

Additionally, there was biodistribution signal from the brain corroborating earlier studies that used TMP as a ligand to cross the blood brain barrier in rodents. In mice that had been pretreated with oral TMP there was a marked decreased in uptake in the kidneys without significant changes in other tissues (FIG. 12B).

In summary, the results with [$^{11}$C]TMP illustrate that there is little uptake in control cells in vitro. Additionally, co-treatment with cold TMP blocked specific uptake and co-treatment with inhibitory concentration of MTX showed no change in the dynamic range of uptake, and only minimal change in overall uptake in DHFR cells.

Figure 13:
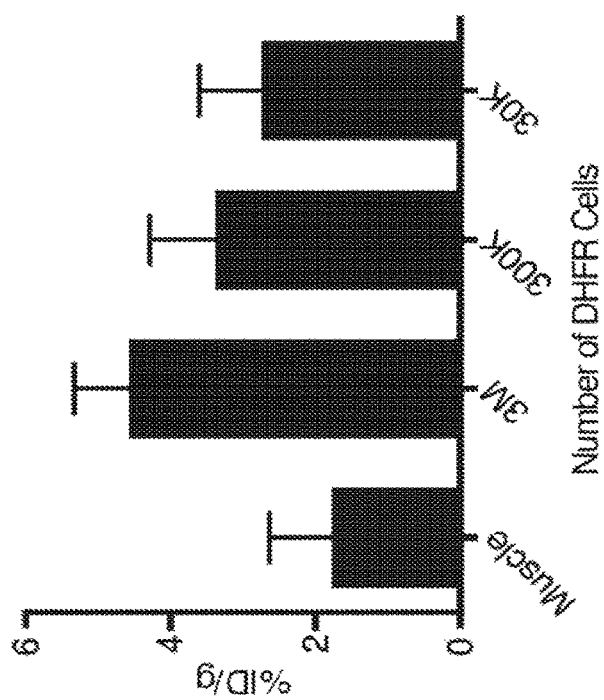
FIG. 13 is a bar graph showing the sensitivity of detection of transduced DHFR reporter cells. HEK293 DFHR cells were injected subcutaneously in matrigel (150 μL) at concentrations of $3 \times 10^6$, $3 \times 10^5$, and $3 \times 10^4$ cells 24 h prior to radiotracer administration and PET imaging. The matrigel was harvested and measured on a gamma counter. Error bars represent the SEM (n=3) and there was statistical significance of $3 \times 10^6$ and $3 \times 10^5$ cells (P<0.05 Student T, two tailed).

The number of cells detectable by imaging in a particular tissue/volume is crucial information, especially for investigators interested whether adoptive cell therapies are reaching the target solid tumor. Thus, cell sensitivity experiments were performed to assess the minimum number of cells necessary for detection of radiotracer signal. Given the strong in vitro signal uptake, HEK293 cells carrying DHFR transgene were diluted (3M, 300K, and 30K) and injected in 150 µL of matrigel matrix and imaged the next day. A representative mouse image is shown of the 300K cell shoulder area (FIG. 13), and ex vivo analysis by gamma counting corroborated detection of 300K cells (P<0.05).

Example 14: [$^{11}$C]TMP Bacteria Comparison Studies

This example was performed to show the uptake of [$^{11}$C]TMP, initial dose of 2 million counts per minute CPM/mL on live bacteria over heat killed bacteria after a 30 minute incubation. The bacteria were then pelleted and washed in PBS twice before uptake was assessed on a gamma counter (Perkin Elmer). Several bacterial stains were tested including *S. aureus* (Xen 29, Perkin Elmer #119240) *Pseudomonas* (Xen 05 Perkin Elmer #119228) and *E. coli* (Xen 14 Perkin Elmer 119223).

Figure 9:
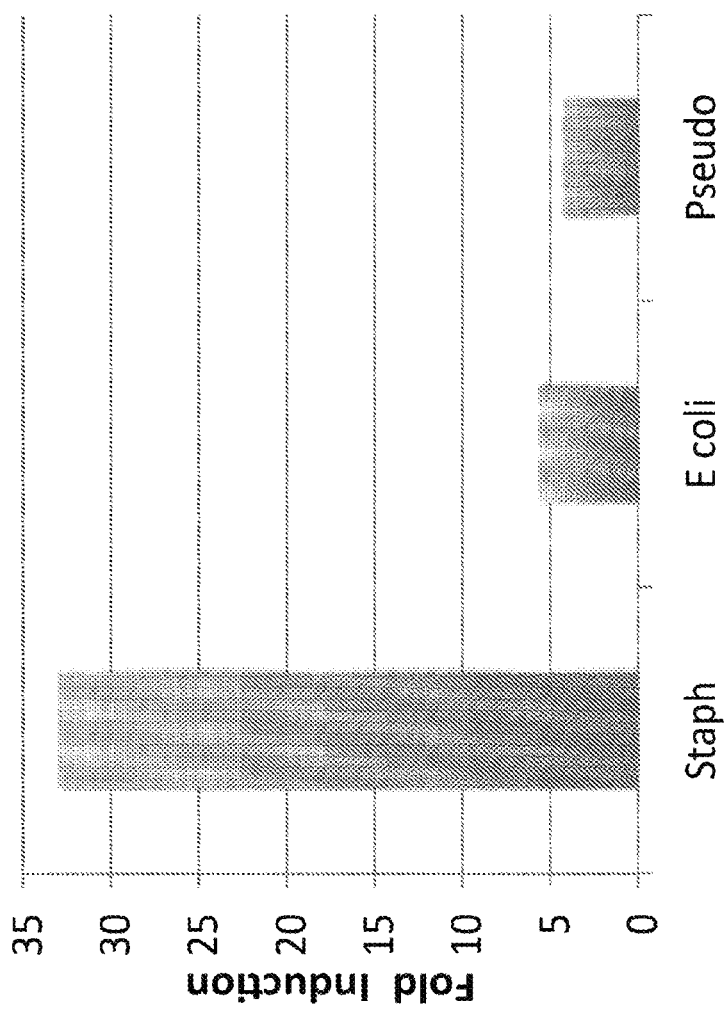
FIG. 9 is a bar graph illustrating the fold induction of live bacteria (Staph, *Pseudomonas*, and *E. coli*) over heat killed bacteria.

The results (FIG. 9) illustrate that a high fold-induction in all strains of bacteria tested and over 40 fold induction in *Staphylococcus*.

Example 15: [1C]TMP Bacteria Concentrations Study

This example was performed to study the effect of [$^{11}$C] TMP in the presence of varying *E. coli* (Invitrogen; HB101) bacterial concentrations from <1×10$^5$ to 1×10$^7$ colony forming units per mL. The [$^{11}$C]TMP initial dose was 2 million counts per minute (cpm)/mL, the bacteria were pelleted, washed twice in PBS and uptake was assessed with a gamma counter (Perkin Elmer).

Figure 8:
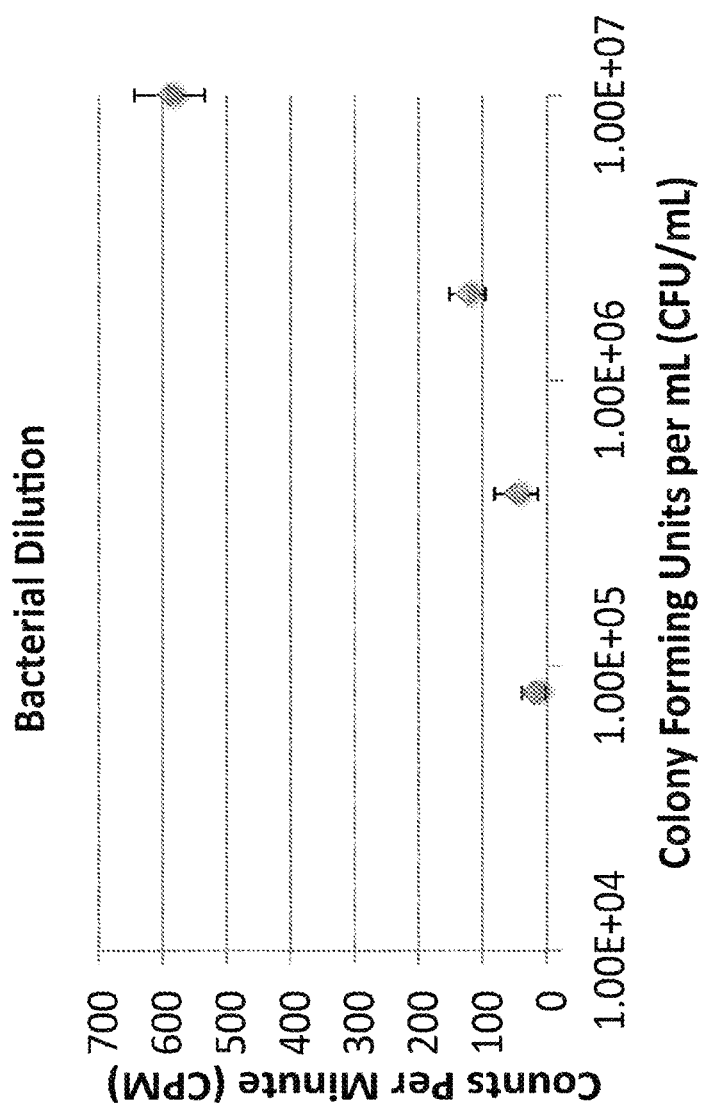
FIG. 8 is a plot of cpm vs. colony forming units (cfu/mL) showing that [$^{11}$C]TMP shows a greater binding/signal ratio in the presence of more live bacteria.

There was greater uptake with higher concentrations of bacteria, suggesting that [$^{11}$C]TMP may quantitatively report the number of bacteria in a given infection. FIG. 8 shows that the more live bacteria that are present the greater the binding/signal of [$^{11}$C]TMP.

Figure 17:
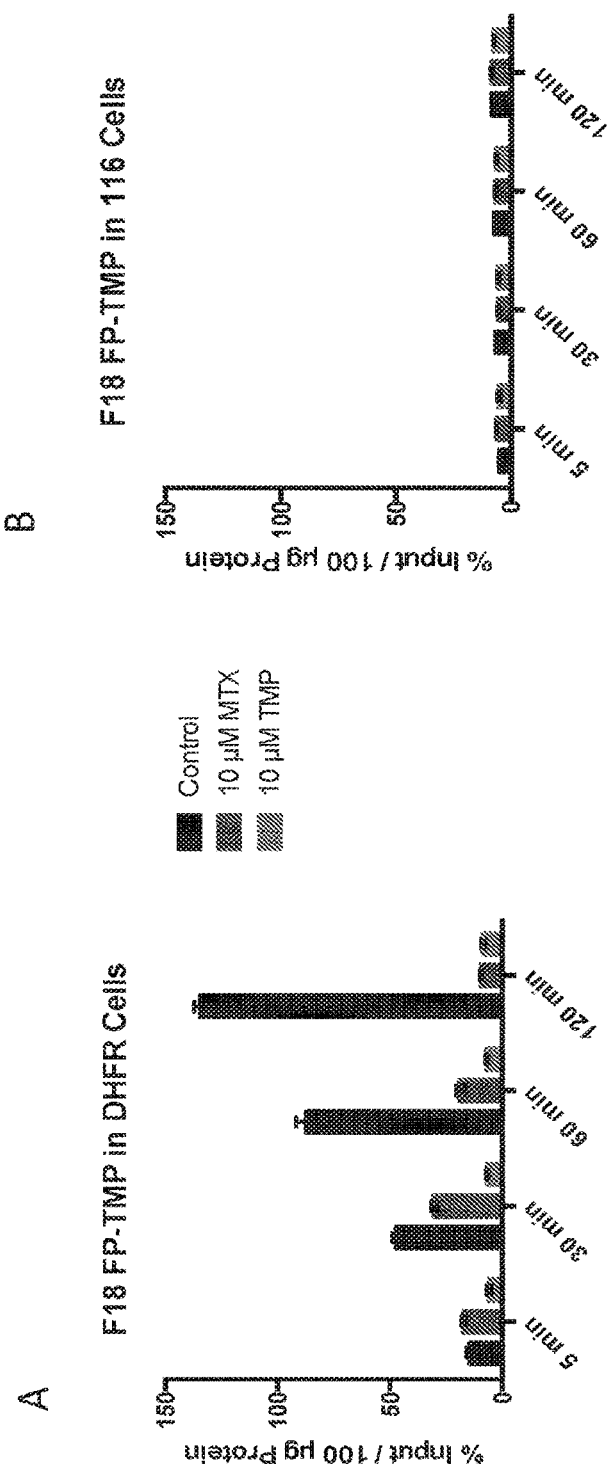
FIGS. 17A and 17B are bar graphs showing the results of [$^{18}$F]FPTMP uptake/specificity studies in HCT116 DHFR cells (FIG. 17A) and HCT116 (FIG. 17B) cells.
Figure 18:
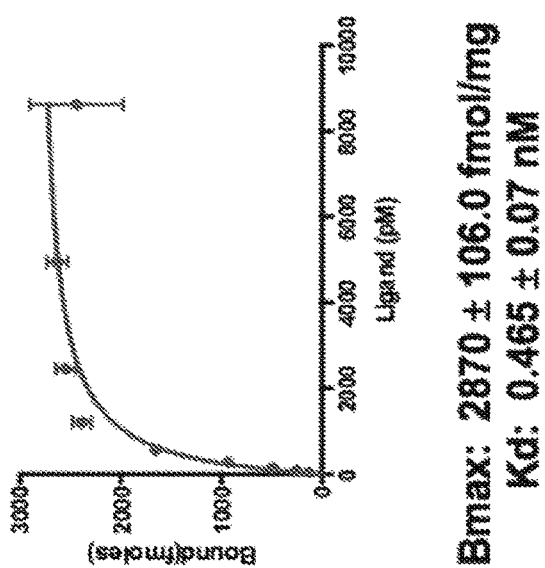
FIG. 18 is a line graph showing a $B_{max}$ of 2870±106 fmol/mg and $K_d$ of 0.465±0.07 nM in HCT and HCT116 DHFR cells.

Example 16: $^{18}$F-FP-TMP Uptake/Specificity Studies $^{18}$F-FP-TMP uptake/specificity studies in HCT116 and HCT116 DHFR cells were conducted. Forty thousand cells/well/100 µL were plated in a 96 well plate 24 hours prior to the experiment. On the day of the experiment, about 70,000 cpm/50 µL/well in DMEM media were added and incubated for about 60 minutes at about 37° C. Fresh MTX and TMP (10 µM) solutions were prepared and then co-incubated with ligand. At the end of each time, media was aspirated and individual wells were counted in a gamma counter. See, Tables 1 and 2 and FIGS. 17 and 18.

TABLE 1

|  | DHFR | | 10 µM MTX | | 10 µM TMP | |
| --- | --- | --- | --- | --- | --- | --- |
| Time (min) | Mean | SD | Mean | SD | Mean | SD |
| 5 | 14.3 | 1.87 | 17.2 | 1.03 | 5.82 | 1.1 |
| 30 | 47.2 | 1.84 | 30.4 | 1.29 | 6.66 | 0.48 |
| 60 | 87.1 | 4.82 | 18.8 | 1.84 | 7.04 | 0.7 |
| 120 | 134.6 | 2.71 | 9.42 | 0.73 | 8.38 | 1.13 |

TABLE 2

|  | Control | | 10 µM MTX | | 10 µM TMP | |
| --- | --- | --- | --- | --- | --- | --- |
| Time (min) | Mean | SD | Mean | SD | Mean | SD |
| 5 | 5.11 | 0.49 | 6.32 | 0.41 | 5.37 | 0.78 |
| 30 | 6.58 | 0.51 | 5.59 | 0.43 | 5.83 | 0.48 |

TABLE 2-continued

|  | Control | | 10 µM MTX | | 10 µM TMP | |
| --- | --- | --- | --- | --- | --- | --- |
| Time (min) | Mean | SD | Mean | SD | Mean | SD |
| 60 | 7.37 | 0.62 | 6.74 | 0.63 | 6.48 | 0.52 |
| 120 | 8.4 | 0.52 | 8.62 | 0.66 | 7.61 | 0.33 |

The Lowry method was then conducted for protein determination (DHFR: 22.3 µg and 116: 24.5 µg).

These results illustrate that there was over 7-fold induction and 15-fold signal induction in DHFR cells compared to control cells at 30 and 120 minutes respectively. This is an improved signal to noise (target to background) compared to [$^{11}$C]TMP The B-Max and kD for [$^{18}$F]FPTMP were 2870 and fmol/mg and 0.465 nM respectively. This indicates a very strong binding affinity of [$^{18}$F]FPTMP for Ec DHFR in mammalian cell. This affinity is on par with unmodified TMP and suggest excellent targeting of the desired protein and little if any off target effects or binding.

Example 17: [$^{18}$F]FPTMP In Vitro Detection

Figure 19:
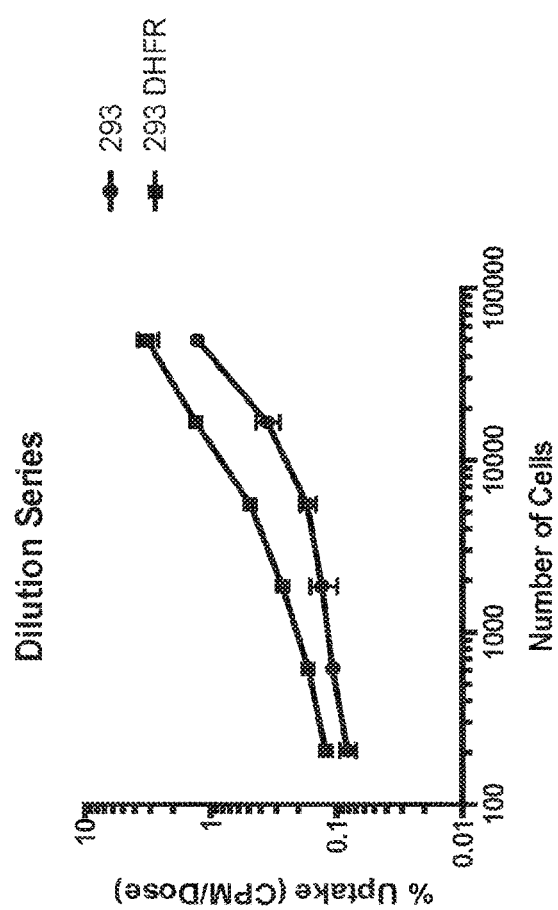
FIG. 19 is a line graph showing [$^{18}$F]FPTMP uptake after serial dilutions of 293 (●) and 293 DHFR (■) cells.

Serial Dilutions of 293 and 293 DHFR cells were incubated with [$^{18}$F]FPTMP for 2 hours and washed twice. Cellular uptake was assessed on a gamma counter (FIG. 19).

These results show that [$^{18}$F]FPTMP in vitro detection is sensitive to a few hundred DHFR cells.

Example 18: [$^{18}$F]FPTMP Validation: Tumor Model

Small animal micro PET/CT of DHFR tumors with [$^{18}$F] FPTMP. HCT116 tumors were xenografted subcutaneously (8 million cells) to the shoulders of nude mice. The tumors were grown for 14 days and imaged using small animal PET followed by CT imaging. A representative animal is shown at imaging time point 4 h after [$^{18}$F]FPTMP ~0.1 mCi IV.

Figure 20:
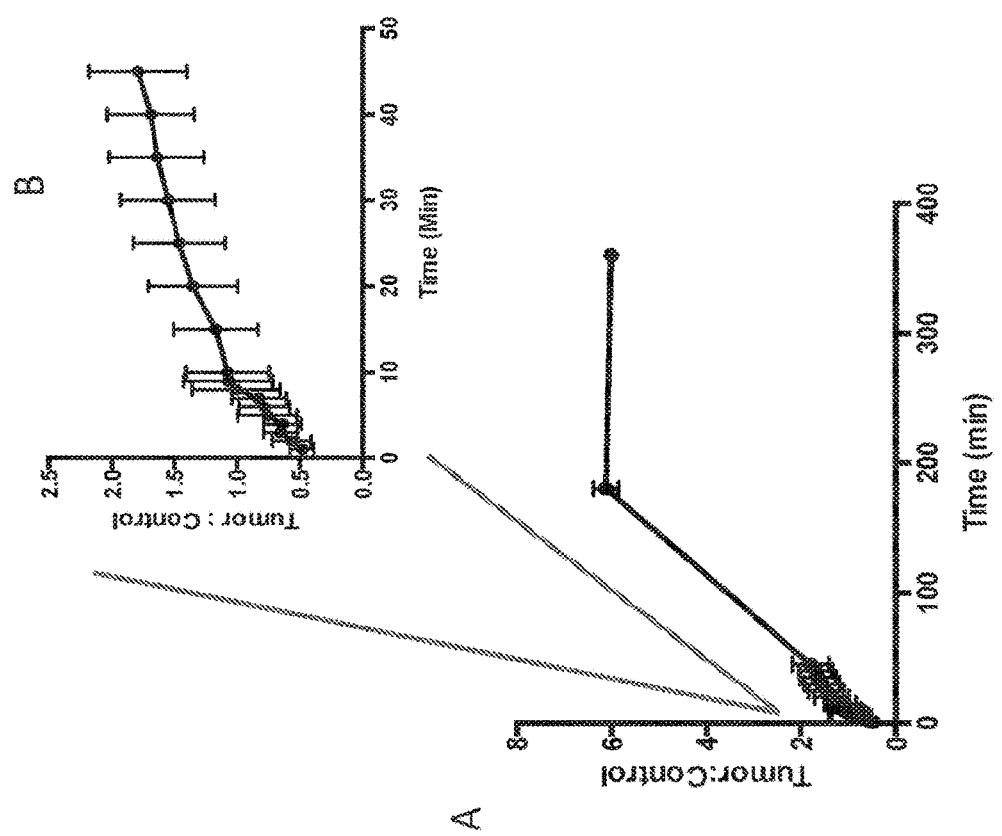
FIG. 20A illustrates the quantification of in vivo uptake data in an experiment performed similarly to FIGS. 11A and 11B but with [$^{18}$F]FPTMP. Error bars represent standard deviation (n=3).
FIG. 20B is an expanded section of the 0 to 2.5 y-axis over 50 minutes.

FIGS. 20A and 20B illustrate the quantification of in vivo uptake data. Error bars represent standard deviation (n=3).

Example 19: [$^{18}$F]FPTMP Bio-Distribution

Bio-distribution studies were performed at 6 h after $^{18}$F FPTMP injection.

Figure 21:
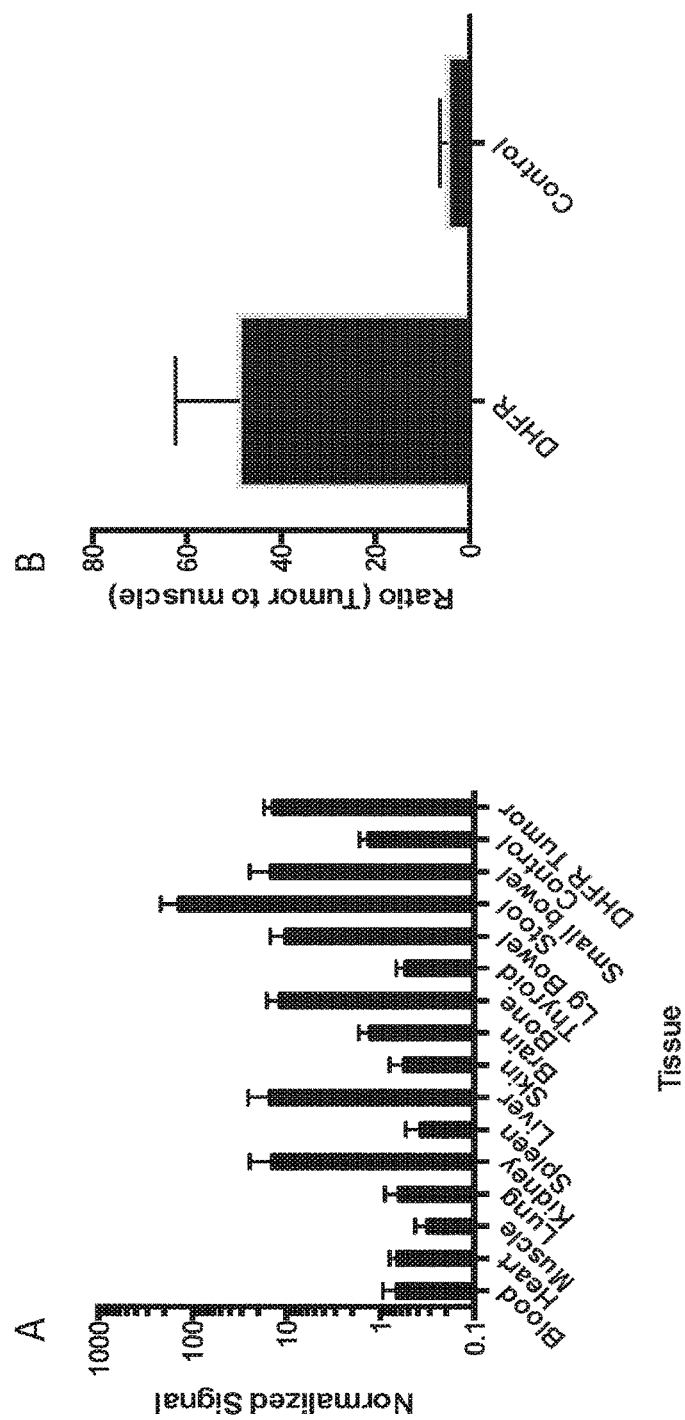
FIGS. 21A and 21B are bar graphs showing the normalized signal in tissue and biodistribution of [$^{18}$F]FPTMP and quantification of tumor to muscle ratios for the control and DHFR. Error bars represent standard deviation (n=3).

FIGS. 21A and 21B provide the quantification of tumor to muscle ratio. Error bars represent standard deviation (n=3).

Example 20: [$^{18}$F]FPTMP Bacterial Uptake In Vitro

Figure 22:
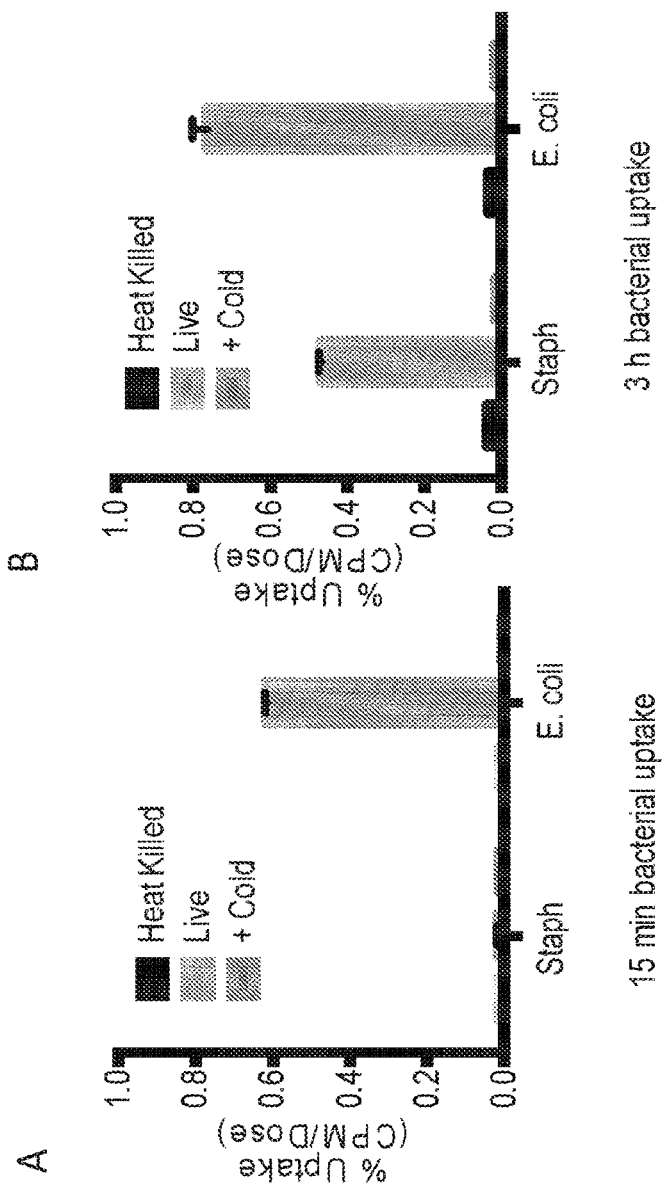
FIGS. 22A and 22B are bar graphs showing the % uptake of [$^{18}$F]FPTMP in the absence and presence of cold TMP for heat-killed *S. aureus* and *E. coli* bacteria after 15 minutes (FIG. 22A) and 3 hours (FIG. 22B).

Heat-killed *S. aureus* and *E. coli* bacteria were boiled at 98° C. for 10 minutes. The bacteria were then pelleted at 6000 g for 5 minutes and incubated with [$^{18}$F]FPTMP in PBS for 15 min and 3 h at 37° C. with and without cold TMP (10 µM). The bacteria were pelleted repeatedly, washed twice with cold PBS, and assayed for uptake with a gamma counter. Error bars represent standard deviation (n=3). See, FIGS. 22A/B.

Example 21: Infection v Inflammation v Tumor Using [$^{18}$F]FPTMP

Figure 23:
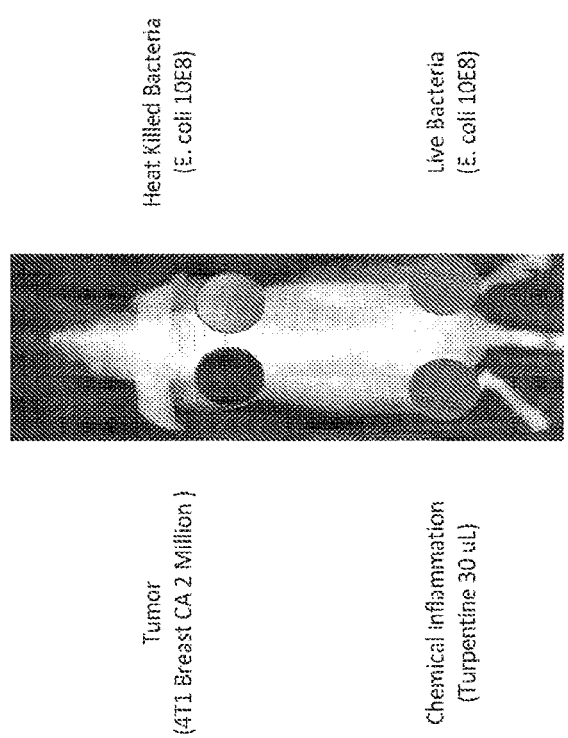
FIG. 23 is a schematic and image of a mouse injected with turpentine (left leg), live bacteria (right leg), heat killed bacteria (right shoulder) and mouse breast cancer cells (left shoulder) prior to imaging.
Figure 24:
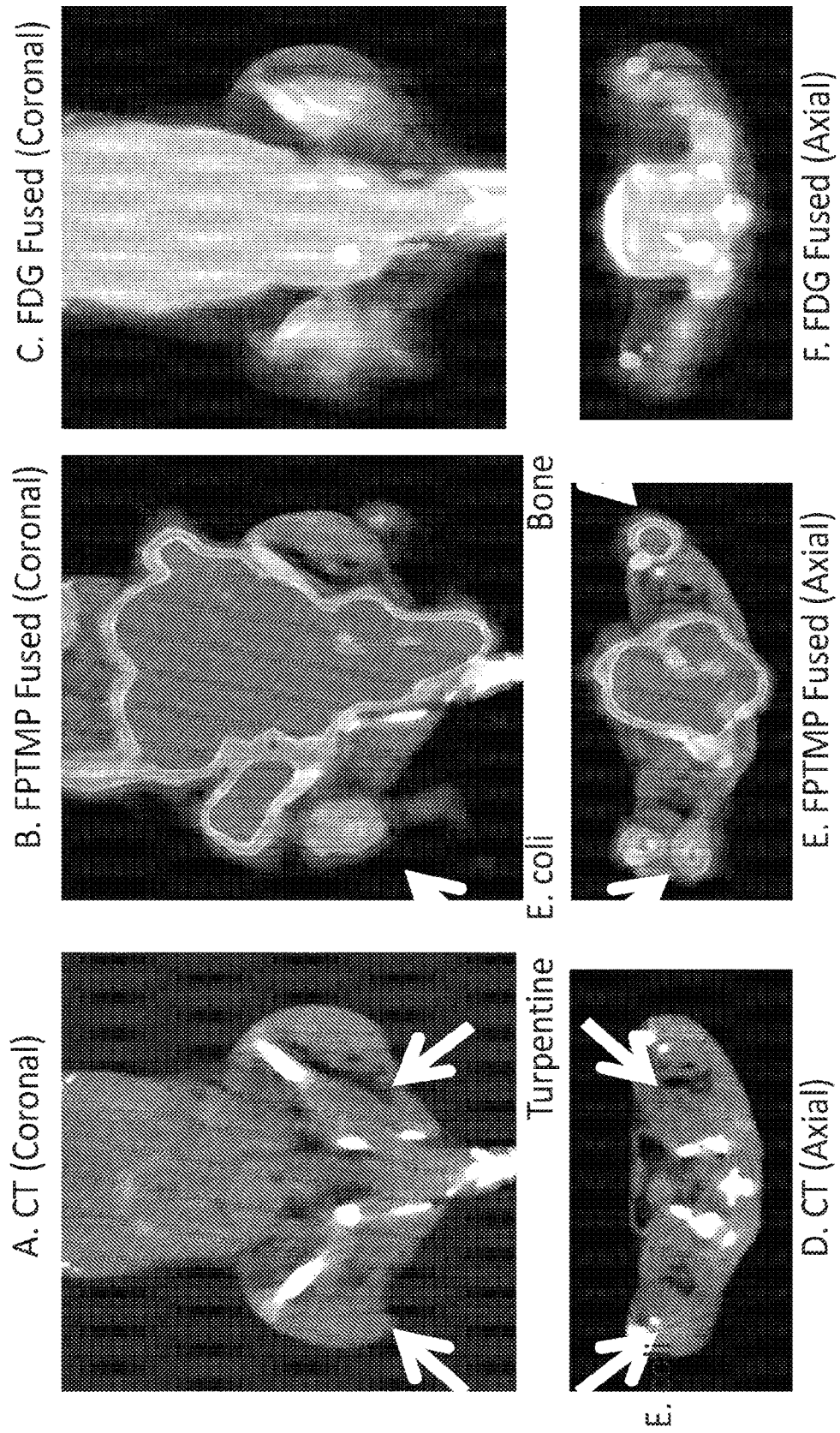
FIGS. 24A-24F are coronal (FIGS. 24A-24C) and axial (FIGS. 24D-24F) images of a live mouse after injection of [$^{18}$F]FPTMP and next day injection and imaging of [$^{18}$F]FDG. The data shows [$^{18}$F]FPTMP uptake only in live bacteria, but in turpentine inflammation. The data shows [$^{18}$F]FDG uptake only in both live bacteria and turpentine inflammation.
Figure 25:
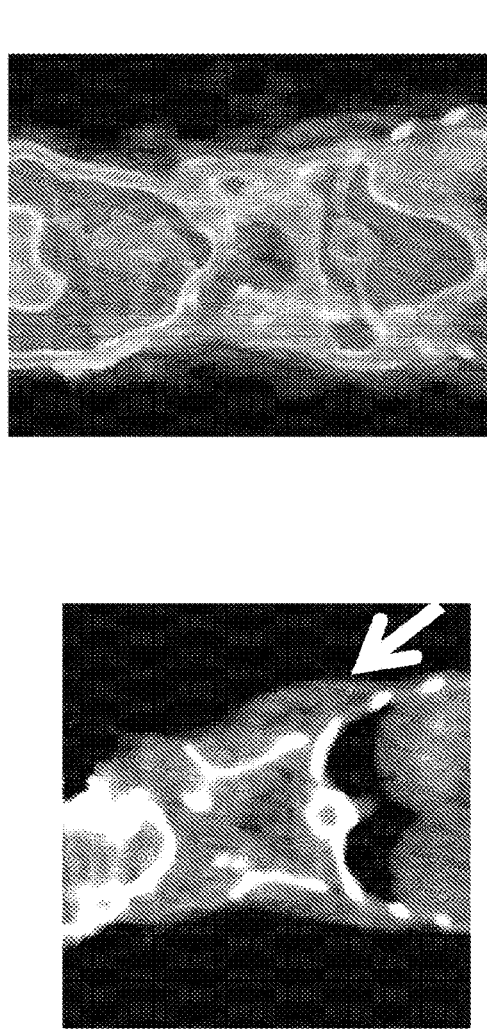
FIGS. 25A-25F are coronal (FIGS. 25A-25C) and axial (FIGS. 25D-25F) images of a live mouse after injection of [$^{18}$F]FPTMP and next day injection and imaging of [$^{18}$F]FDG showing the absence of [$^{18}$F]FPTMP uptake in tumor cells and the presence of [$^{18}$F]FDG in tumor cells.
Figure 25:
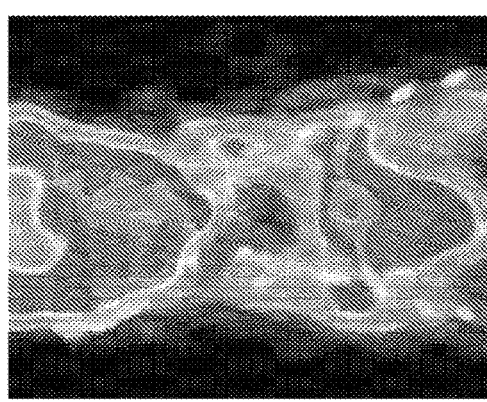
Figure 25:
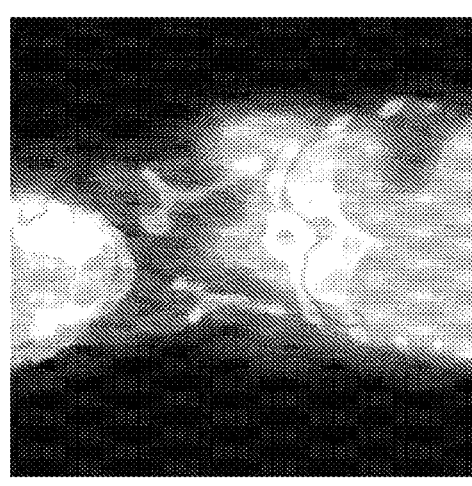
Figure 25:
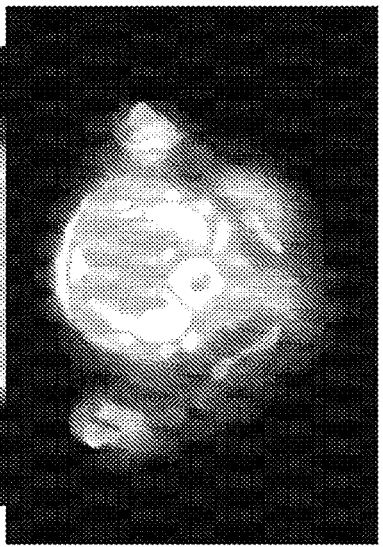
Figure 25:
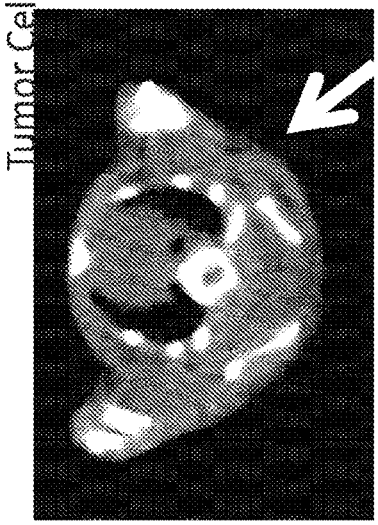
Figure 26:
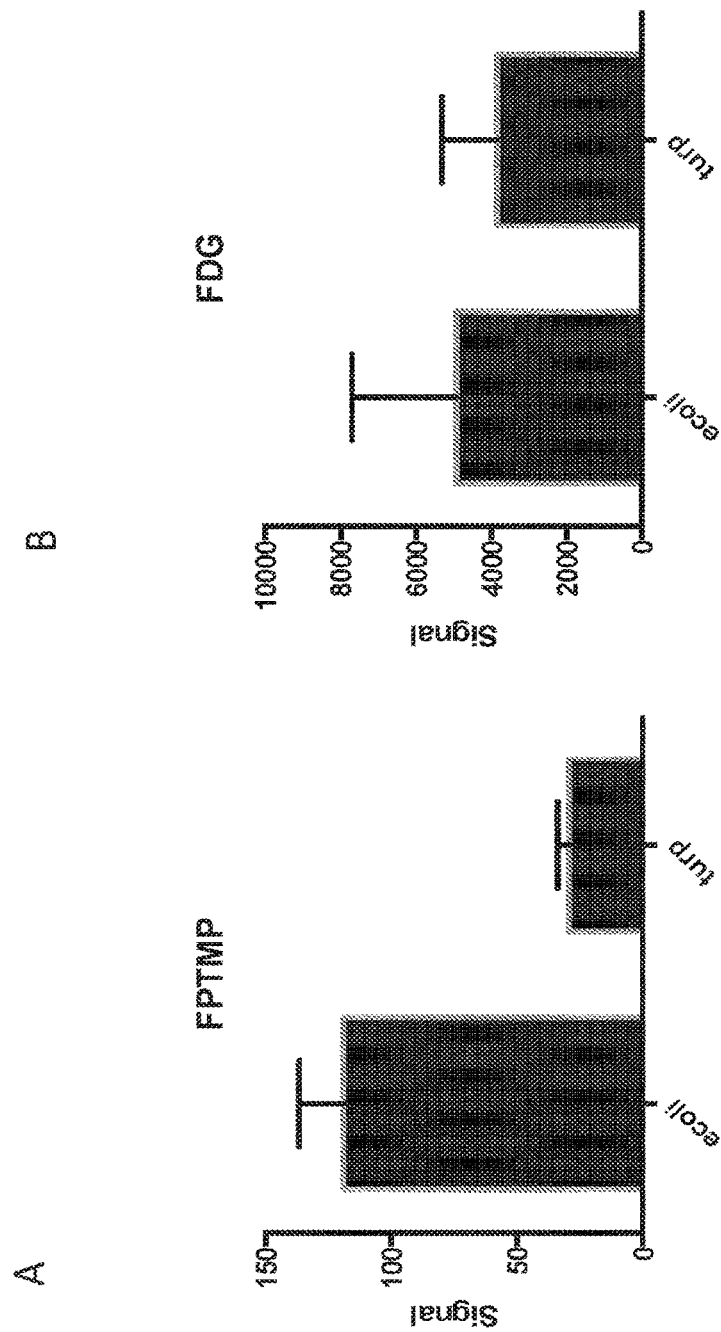
FIGS. 26A and 26B are bar graphs showing quantification of the levels of uptake as seen in 24 FIGS. 24A-24F, in infection versus inflammation for FPTMP (FIG. 26A) and FDG (FIG. 26B).

Balb/c mice were injected with 30 µL of turpentine into their left leg 3 days prior to imaging. This provided a bland (non-infectious) inflammation control. Live bacteria (*E. coli*, 1×10$^8$ CFU) were injected subcutaneously into the right leg and heat killed bacteria were injected into the right shoulder 12 h prior to imaging. Mouse breast cancer cells (4T1, 2 million) were injected subcutaneously into the left shoulder 12 h prior to imaging (FIG. 23).

Balb/c mice were injected with 1 mg of D-luciferin prior bioluminescence imaging. This effectively checked for live 4T1 tumor cells (carrying luciferase gene). The *E. coli* contain the Lux operon (Bioluminescence protein and substrate synthetic pathway) and are bioluminescent without exogenous luciferin. Bioluminescent imaging was performed with 5 minute bin prior to radiotracer injection (FIGS. 24A-24E).

Balb/c mice were injected with about 100 mCi of [$^{18}$F] FPTMP. Time activity curves of the mice were performed over 45 minutes. Subsequent time points at 2, 4, and 6 hours were performed (n=3). The following day animals were injected with about 200 mCi of fludeoxyglucose ([$^{18}$F] FDG). Animals were sacrificed, tissues harvested for Bio-D and lower limbs were OCT flash frozen for future IHC (FIGS. 25A-25F).

These results illustrate that [$^{18}$F]FPTMP uptake was observed in live bacteria, but not in turpentine inflammation and that there was no difference in [$^{18}$F]FDG uptake for bacteria versus turpentine inflammation (FIGS. 24A-24F and 26). These results also illustrate that there is no [$^{18}$F] FPTMP uptake in tumor cells (FIGS. 25A-25F).

It is to be understood that while the invention has been described in conjunction with the preferred specific embodiments thereof, that the foregoing description and the examples that follow are intended to illustrate and not limit the scope of the invention. It will be understood by those skilled in the art that various changes may be made and equivalents may be substituted without departing from the scope of the invention, and further that other aspects, advantages and modifications will be apparent to those skilled in the art to which the invention pertains. In addition to the embodiments described herein, the present invention contemplates and claims those inventions resulting from the combination of features of the invention cited herein and those of the cited prior art references which complement the features of the present invention. Similarly, it will be appreciated that any described material, feature, or article may be used in combination with any other material, feature, or article, and such combinations are considered within the scope of this invention.

The disclosures of each patent, patent application, and publication cited or described in this document are hereby incorporated herein by reference, each in its entirety, for all purposes.

What is claimed is:

1. A method of monitoring immunotherapy in a subject, said method comprising:
    (a) genetically engineering cells from said subject to express dihydrofolate reductase;
    (b) tagging said engineered cells with a compound of formula (I):

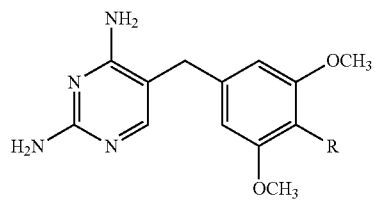

wherein, R is —O—C$^{11}$—(C$_1$ to C$_6$ alkyl), an O—C$^{11}$-glycol, —O—(C$_1$ to C$_6$ alkyl)-$^{18}$F, —OCH$_2$—($^{18}$F substituted phenyl), —OCH$_2$CH$_2$—($^{18}$F-substituted triazole), —OCH$_2$CH$_2$—($^{18}$F-substituted tetrazole), $^{18}$F-substituted boron-dipyrromethene, —O(CH$_2$CH$_2$O)$_n$CH$_2$CH$_2$—$^{18}$F, —OCH$_2$CH$_2$CH$_2$NHC(O)(CH$_2$CH$_2$O)$_n$—CH$_2$CH$_2$—$^{18}$F, -L$^1$-$^{68}$Ga, -L$^1$-$^{64}$Cu, -L$^1$-$^{99m}$Tc, radioactive halogen, $^{211}$At, -L$^1$-$^{10}$B, -L$^1$-$^{32}$P, -L$^1$-$^{90}$Y, -L$^1$-$^{103}$Pd, -L$^1$-$^{131}$Cs, -L$^1$-$^{153}$Sm, -L$^1$-$^{177}$Lu, -L$^1$-$^{211}$At, -L$^1$-$^{212}$Bi, -L$^1$-$^{212}$Po, -L$^1$-$^{212}$Pb, -L$^1$-$^{223}$Ra, or -L$^1$-$^{225}$Ac;

n is 1-3;

L$^1$ is a chelation linker;

or a pharmaceutically acceptable salt or prodrug thereof;

(c) administering said genetically engineered and tagged cells to said subject; and
(d) tracking said genetically engineering cells and tagged cells by imaging.

2. The method of claim 1, wherein said radioactive halogen is $^{18}$F, $^{123}$I, $^{125}$I, $^{124}$I, $^{131}$I, $^{32}$Cl, $^{33}$Cl, $^{34}$Cl, $^{74}$Br, $^{75}$Br, $^{76}$Br, $^{77}$Br, or $^{78}$Br.

3. The method of claim 1, wherein R is O$^{11}$CH$_3$.

4. The method of claim 1, wherein R is $^{18}$F.

5. The method of claim 1, wherein L$^1$ is DTPA, HEHA, NOTA, DOTA, CHX-A, or TCMC.

6. The method of claim 1, wherein the compound is:

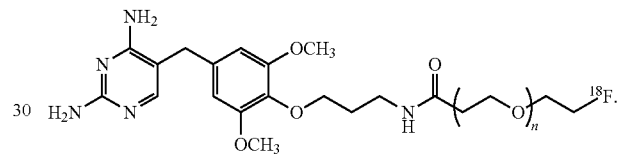

7. The method of claim 1, wherein the compound is:

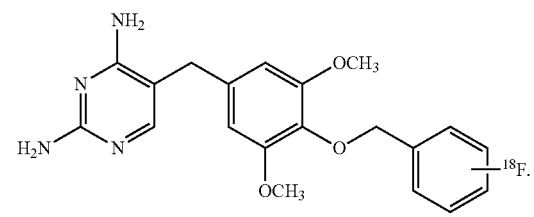

8. The method of claim 1, wherein the compound is:

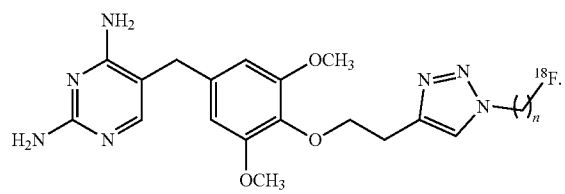

9. The method of claim 1, wherein the compound is:

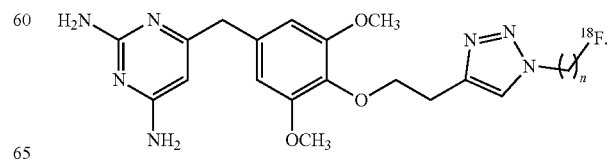

10. The method of claim 1, wherein the compound is:
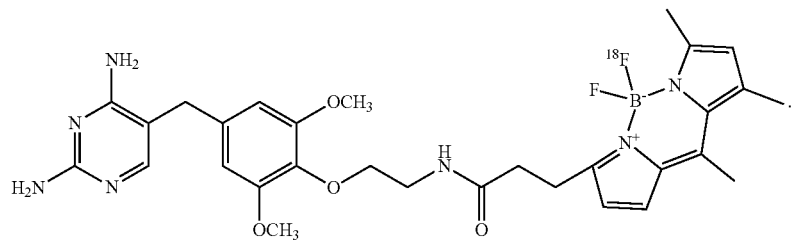 [SMILES: COc1cc(Cc2cnc(N)nc2N)cc(OC)c1OCCNC(=O)CCC1=[N+]2C(=C(C)c3c(C)cc(C)n3[B-]2(F)[18F])C=C1]
11. The method of claim 1, wherein the compound has the following structure:
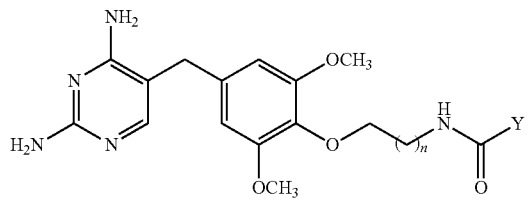
wherein:
n is 1 to 6; and
Y is
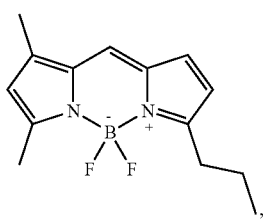
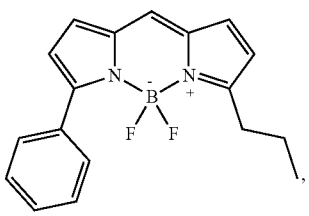
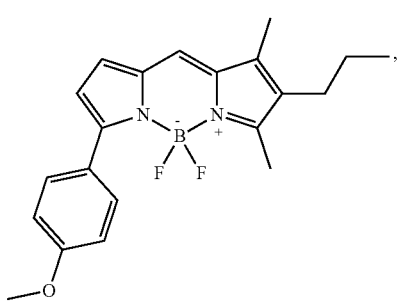
-continued
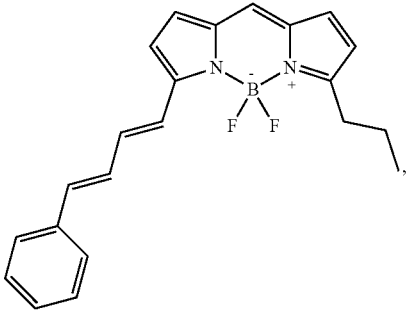
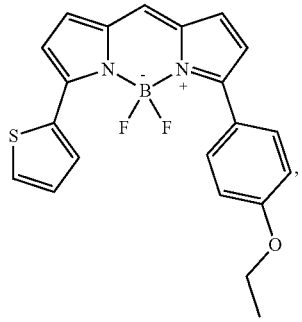
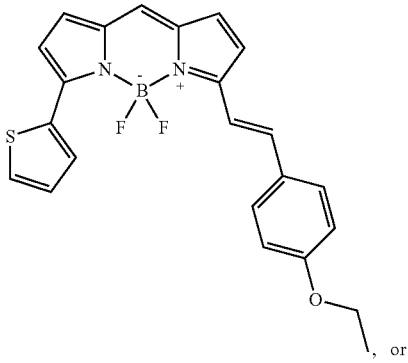, or

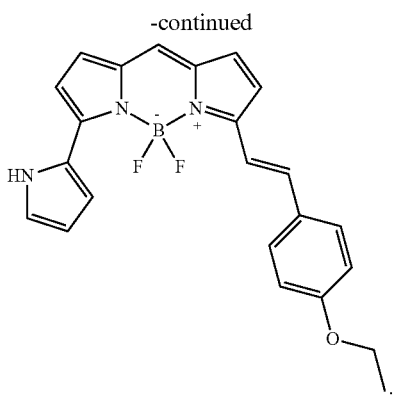

12. The method of claim 1, wherein $^{64}$Cu, $^{68}$Ga, $^{10}$B, $^{32}$P, $^{90}$Y, $^{103}$Pd, $^{131}$Cs, $^{153}$Sm, $^{177}$Lu, $^{211}$At, $^{212}$Bi, $^{212}$Po, $^{212}$Pb, $^{223}$Ra, or $^{225}$Ac is chelated.

13. The method of claim 12, wherein the chelation is performed using:

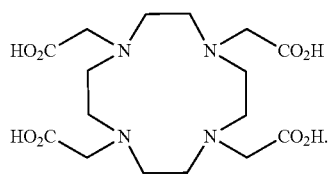 [SMILES: O=C(O)CN1CCN(CC(=O)O)CCN(CC(=O)O)CCN(CC(=O)O)CC1]

14. The method of claim 12, wherein the chelation is performed using:

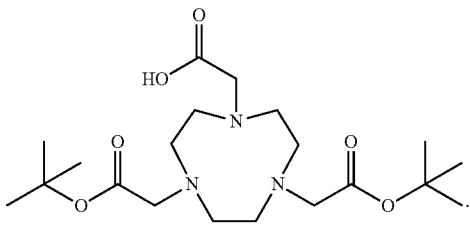 [SMILES: CC(C)(C)OC(=O)CN1CCN(CC(=O)O)CCN(CC(=O)OC(C)(C)C)CC1]

15. The method of claim 12, wherein the chelation is performed using:

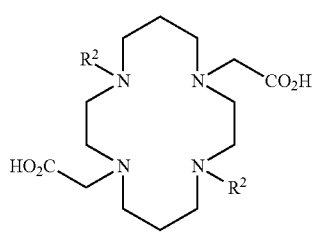

wherein, $R^2$ is, independently, H or CH$_2$CO$_2$H.

16. The method of claim 12, wherein the chelation is performed using:

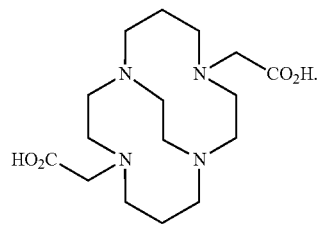 [SMILES: O=C(O)CN1CCCN2CCN(CCCN(CC(=O)O)CC2)CC1]

17. The method of claim 12, wherein the chelation is performed using:

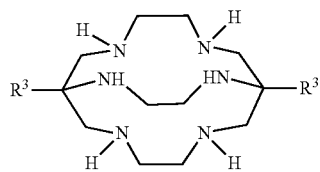

wherein, $R^3$ is, independently, H or NH$_2$.

18. The method of claim 12, wherein the chelation is performed using:

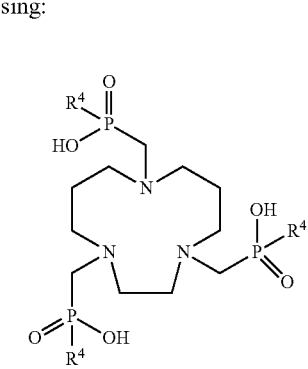

wherein, $R^4$ is, independently, H, —(CH$_2$)$_2$CO$_2$H, CH$_2$OH, or phenyl.

19. The method of claim 12, wherein the chelation is performed using:

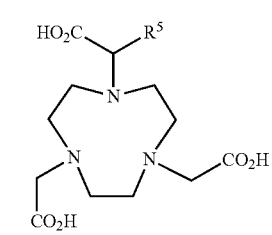

wherein, $R^5$ is H or —(CH$_2$)$_2$CO$_2$H.

20. The method of claim 12, wherein the chelation is performed using:

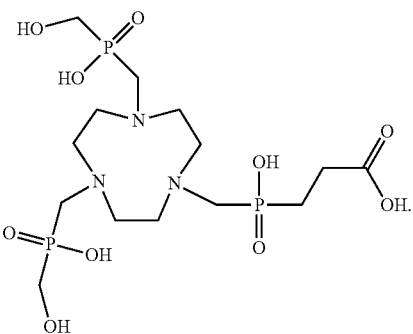 [SMILES: O=C(O)CCP(=O)(O)CN1CCN(CP(=O)(O)CO)CCN(CP(=O)(O)CO)CC1]

21. The method of claim 12, wherein the chelation is performed using:

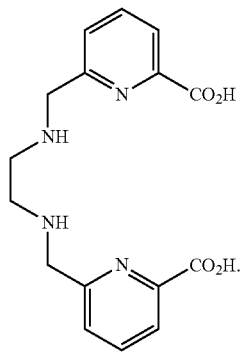 [SMILES: O=C(O)c1cccc(CNCCNCc2cccc(C(=O)O)n2)n1]

22. The method of claim 1, wherein R is:

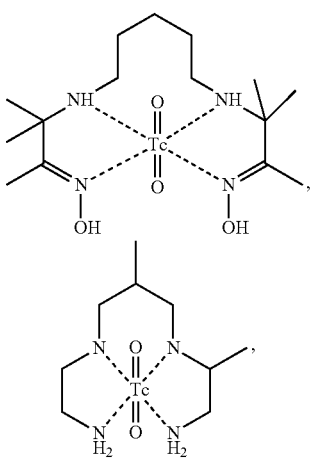

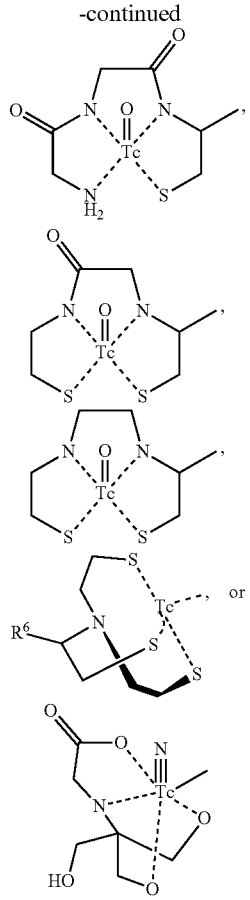

wherein, $R^6$ is alkyl or alkoxy.

23. The method of claim 1, wherein said cells are T-cells, NK-cells, macrophages, B-cells, stem cells, hematopoietic stem cells, mesenchymal stem cells, neuroprogenitor cells, or induced pluripotent cells.

24. The method of claim 1, wherein said tracking is performed using positron emission tomography or single photon emission computed tomography.

25. The method of claim 24, wherein the positron emission tomography does not display areas of inflammation.

26. The method of claim 1, wherein the compound is administered through oral, intravenous, intra-arterial, intra-peritoneal, intrathecal, or intracavitary injection.

* * * * *

UNITED STATES PATENT AND TRADEMARK OFFICE
CERTIFICATE OF CORRECTION

PATENT NO. : 10,835,625 B2
APPLICATION NO. : 16/511052
DATED : November 17, 2020
INVENTOR(S) : Sellmyer et al.

It is certified that error appears in the above-identified patent and that said Letters Patent is hereby corrected as shown below:

In the Claims

Under Column 46, Claim no. 9, Line no. 60, Replace, " 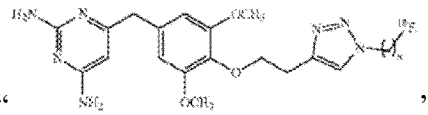 " With

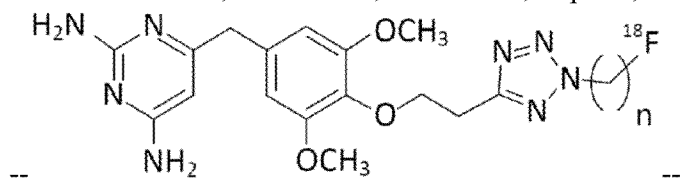

--

Under Column 51, Claim no. 22, Line no. 50, Replace, " 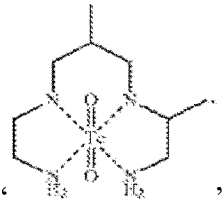 " With

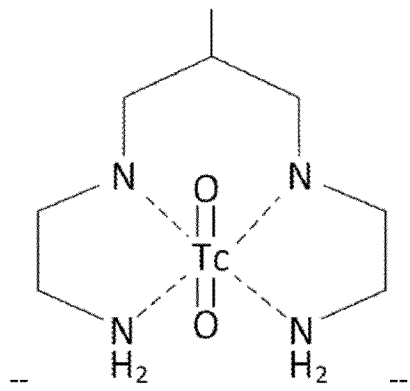

--

Signed and Sealed this
Tenth Day of August, 2021

Drew Hirshfeld
*Performing the Functions and Duties of the
Under Secretary of Commerce for Intellectual Property and
Director of the United States Patent and Trademark Office*